(12) United States Patent
Bakaletz et al.

(10) Patent No.: US 7,501,131 B2
(45) Date of Patent: Mar. 10, 2009

(54) HAEMOPHILUS INFLUENZAE TYPE IV PILI

(75) Inventors: Lauren O. Bakaletz, Hilliard, OH (US);
Robert S. Munson, Jr., Hilliard, OH (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 0 days.

(21) Appl. No.: 11/019,005

(22) Filed: Dec. 21, 2004

(65) Prior Publication Data

US 2005/0158335 A1    Jul. 21, 2005

Related U.S. Application Data

(60) Provisional application No. 60/532,296, filed on Dec. 23, 2003.

(51) Int. Cl.
*A61K 39/02* (2006.01)
*A61K 45/00* (2006.01)

(52) U.S. Cl. .............. 424/242.1; 424/184.1; 424/234.1; 424/256.1; 424/278.1; 435/243; 435/851; 530/300; 530/350

(58) Field of Classification Search .............. 424/184.1, 424/234.1, 242.1, 256.1, 278.1; 435/243, 435/851; 530/300, 350
See application file for complete search history.

(56) References Cited

U.S. PATENT DOCUMENTS

| 6,054,265 | A | * | 4/2000 | Barney et al. ................... 435/5 |
| 6,268,171 | B1 | | 7/2001 | Meyer et al. |
| 6,476,208 | B1 | * | 11/2002 | Cohen et al. ................ 536/23.1 |
| 6,506,581 | B1 | | 1/2003 | Fleischmann et al. |

OTHER PUBLICATIONS

Anderson et al., *J. Clin. Invest.*, "Human Serum Activities Against *Hemophilus influenzae*, Type b", 51:31-38 (1972).
Bakaletz et al., *Infect. Immun.*, "Frequency of Fimbriation of Nontypable *Haemophilus influenzae* and Its Ability To Adhere to Chinchilla and Human Respiratory Epithelium", 56:331-335 (1988).
Bakaletz et al., *J. Infect. Dis.*, "Modeling Adenovirus Type 1-Induced Otitis Media in the Chinchilla: Effect on Ciliary Activity and Fluid Transport Function of Eustachian Tube Mucosal Epithelium", 168:865-872 (1993).
Bakaletz and Holmes, *Clin. Diagn. Lab. Immunol.*, "Evidence for Transudation of Specific Antibody in the Middle Ears of Parenterally Immunized Chinchillas after an Upper Respiratory Tract Infection with Adenovirus", 4:223-225 (1997).
Bakaletz et al., *Vaccine*, "Relative immunogenicity and efficacy of two synthetic chimeric peptides of fimbrin as vaccinogens against nasopharyngeal colonization by nontypeable *Haemophilus influenzae* in the chinchilla" 15:955-961 (1997).
Bakaletz et al., *Infect. Immun.*, "Protection against Development of Otitis Media Induced by Nontypeable *Haemophilus influenzae* by Both Active and Passive Immunization in a Chinchilla Model of Virus-Bacterium Superinfection", 67:2746-2762 (1999).

Baldwin, *Am. J. Otol.*, "Effects of Otitis Media on Child Development", 14:601-604 (1993).
Bardy, *Microbiology*, "Prokaryotic Motility Structures", 149:295-304 (2003).
Bendler and Goodgal, *J. Microbiol.*, "The Type b Capsulation Locus of *Haemophilus influenzae*: Map Location and Size", 70:411-422 (1972).
Berman et al., *Pediatrics*, "Theoretical Cost Effectiveness of Management Options for Children with Persisting Middle Ear Effusions", 93(3):353-363 (1994).
Black et al., *Pedriatr. Infect. Dis. J.*, "Efficacy, safety and immunogenicity of heptavalent pneumococcal conjugate vaccine in children", 19:187-195 (2000).
Bright et al., *Am. J. Public Health*, "The Prevalence of Tympanostomy Tubes in Children in the United States, 1988", 83(7):1026-1028 (1993).
Cimons, *ASM News*, "Lurid Reports Obscure Reality of Strep A Outbreaks", 60:527-530 (1994).
Coleman et al., *Inf. and Immunity*, "Molecular Cloning, Expression, and Sequence of the Pilin Gene from Nontypeable *Haemophilus influenzae* M37" 59(5):1716-1722 (1991).
Coleman et al., *J. Clin. Micro.*, "Chemically Defined Media for Growth of *Haemophilus influenzae* Strains", 41:4408-4410 (2003).
Daines et al., *J. Med. Microbiol.*, "*Haemophilus influenzae* Rd KW20 has virulence properties", 52:277-282 (2003).
Darzins and Russell, *Gene*, "Molecular genetic analysis of type-4 pilus biogenesis and twitching motility using *Pseudomonas aeruginosa* as a model system—a review", 192:109-115 (1997).
DeMaria et al., *Infect. Immun.*, "Immunization with Outer Membrane Protein P6 from Nontypeable *Haemophilus influenzae* Induces Bactericidal Antibody and Affords Protection in the Chinchilla Model of Otitis Media", 64:5187-5192 (1996).
Doughty et al., *Vet. Microbiol.*, "The type 4 fimbrial subunit gene of *Pasteurella multocida*", 72:79-90 (2000).
Dougherty and Smith, *Microbiology*, "Identification of *Haemophilus influenzae* Rd transformation genes using cassette mutagenesis", 145(2):401-409 (1999).
Ehrlich et al., *JAMA*, "Mucosal Biofilm Formation on Middle-Ear Mucosa in the Chinchilla Model of Otitis Media", 287(13):1710-1715 (2002).

(Continued)

*Primary Examiner*—Rodney P. Swartz
(74) *Attorney, Agent, or Firm*—Marshall Gerstein & Borun LLP

(57) ABSTRACT

The invention described herein relates to a *Haemophilus influenzae* (*H. influenzae*) regulon encoding type IV pili. In particular, the invention relates to type IV pili from nontypeable *H. influenzae* (NTHi) and from *H. influenzae* strains a, b, c, e and f. The invention provides isolated *H. influenzae* pilus polynucleotides and polypeptides encoded by the polynucleotides as well as polynucleotides and polypeptides encoded by the polynucleotides involved in the assembly/disassembly of the structure. The invention also relates to uses of these polynucleotides and/or polypeptides including methods for eliciting an immune response to *H. influenzae* and methods of treating and preventing *H. influenzae* related pathological conditions.

16 Claims, 1 Drawing Sheet

OTHER PUBLICATIONS

Eskola and Kilpi, *Pedriatr. Infect. Dis. J.*, "Potential of bacterial vaccines in the prevention of acute otitis media", 19:S72-78 (2000).

Eskola et al., *N. Engl. J. Med.*, "Efficacy of a Pneumococcal Conjugate Vaccine Against Acute Otitis Media", 344:403-409 (2001).

Fleischmann et al., *Science*, "Whole-Genome Random Sequencing and Assembly of *Haemophilus influenzae* Rd", 269:496-512 (1995).

Friedrich et al., *Applied and Environmental Microbiology* "Molecular Analyses of the Natural Transformation Machinery and Identification of Pilus Structures in the Extremely Thermophilic Bacterium *Thermus thermophilus* Strain HB27", 68(2):745-755 (2002).

Friedrich et al., *Appl. Environ. Microbiol.*, "Pilin-Like Proteins in the Extremely Thermophilic Bacterium *Thermus thermophilus* HB27:Implication in Competence for Natural Transformation and Links to Type IV Pilus Biogenesis", 69:3695-3700 (2003).

Fussenegger et al., *Gene*, "Transformation competence and type-4 pilus biogenesis in *Neisseria gonorrhoeae*—a review", 192:125-134 (1997).

Genbank Accession No. U32715, "*Haemophilus influenzae* Rd KW20 section 30 of 163 of the complete genome" (Aug. 9, 1995).

Gilsdorf et al., *Pediatr. Res.*, "Role of Pili in *Haemophilus influenzae* Adherence to, and Internalization by, Respiratory Cells", 39:343-348 (1996).

Gilsdorf et al., *Infect. Immun.*, "Role of Pili in *Haemophilus influenzae* Adherence and Colonization", 65:2997-3002 (1997).

Holmes et al., *Microb. Pathog.*, "Adherence of non-typeable *Haemophilus influenzae* promotes reorganization of the actin cytoskeleton in human or chinchilla epithelial cells in vitro", 23:157-166 (1997).

Hunter et al., *Ann. Otol. Rhinol. Laryngol. Suppl.*, "Identification of Hearing Loss in Children with Otitis Media", 163:59-61 (1994).

Jesaitis et al., *J. Immunol.*, "Compromised Host Defense on *Pseudomonas aeruginosa* Biofilms: Characterization of Neutrophil and Biofilm Interactions", 171:4329-4339 (2003).

Kaplan et al., *Pediatr. Infect. Dis. J.*, "Overall cost in the treatment of otitis media", 16:S9-11 (1997).

Karudapuram et al., *J. Bacteriology*, "The *Haemophilus influenzae* dprABC Genes Constitute a Competence-Inducibe Operon That Requires the Product of the tfoX(sxy) Gene for Transcriptional Activation," 179(15):4815-4820 (1997).

Keizer et al., *J. Biol. Chem.*, "Structure of a Pilin Monomer from *Pseudomonas aeruginosa*", 276:24186-24193 (2001).

Kennedy et al., *Infect. Immun.*, "Passive Transfer of Antiserum Specific for Immunogens Derived from a Nontypeable *Haemophilus influenzae* Adhesin and Lipoprotein D Prevents Otitis Media after Heterologous Challenge", 68:2756-2765 (2000).

Klausen et al., *Mol. Microbiol.*, "Biofilm formation by *Pseudomonas aeruginosa* wild type, flagella and type IV pili mutants", 48:1511-1524 (2003).

Klausen et al., *Mol. Microbiol.*, "Involvement of bacterial migration in the development of complex multicellular structures in *Pseudomonas aeruginosa* biofilms", 50:61-68 (2003).

Klein, *Pedriatr. Infect. Dis. J.*, "Role of nontypeable *Haemophilus influenzae* in pediatric respiratory tract infections," 16:S5-8 (1997).

Klein, *Vaccine*, "The Burden of Otitis Media", 19(Suppl. 1):S2-S8 (2001).

Kyd et al., *Infect. Immun.*, "Potential of a Novel Protein, OMP26, from Nontypeable *Haemophilus influenzae* To Enhance Pulmonary Clearance in a Rat Model", 66:2272-2278 (1998).

Mason et al., *Infect. Immun.*, "Nontypeable *Haemophilus influenzae* Gene Expression Induced In Vivo in a Chinchilla Model of Otitis Media", 71:3454-3462 (2003).

Mattick, *Annu. Rev. Microbiol.*, "Type IV Pili and Twitching Motility", 56:289-314 (2002).

Merz et al., *Nature*, "Pilus retraction powers bacterial twitching motility", 407:98-102 (2000).

Mhlanga-Mutangadura et al., *J. Bacteriol.*, "Evolution of the Major Pilus Gene Cluster of *Haemophilus influenzae*", 180(17):4693-4703 (1998).

Mudannayake et al., *Abstracts of the General Meeting of the American Society for Microbiology* "Whole Genome Analysis of Gene Expression Changes During Competence Development in *Haemophilus influenzae*,", 103:D-001 (2003).

Novotny et al., *Infect. Immunity*, "Epitope Mapping of the Outer Membrane Protein P5-Homologous Fimbrin Adhesin of Nontypeable *Haemophilus influenzae*", 68(4):2119-2128 (2000).

Novotny and Bakaletz, *J. Immunol.*, "The Fourth Surface-Exposed Region of the Outer Membrane Protein P5-Homologous Adhesion of Nontypable *Haemophilus influenzae* Is an Immunodominant But Nonprotective Decoying Epitope", 171:1978-1983 (2003).

O'Toole and Kolter, *Mol. Microbiol.*, "Flagellar and twitching motility are necessary for *Pseudomonas aeruginosa* biofilm development", 30:295-304 (1998).

Paap, *Ann. Pharmacother.*, "Management of Otitis Media with Effusion in Young Children", 30(11):1291-1297 (1996).

Perez-Casal et al., *J. Bacteriol.*, "Mry, a trans-Acting Positive Regulator of the M Protein Gene of *Streptococcus pyogenes* with Similarity to the Receptor Proteins of Two-Component Regulatory Systems", 173:2617-2624 (1991).

Poje and Redfield, pp. 57-70 in Herbert et al., (Eds.), *Haemophilus influenzae* Protocols, "Transformation of *Haemophilus influenzae*", Humana Press Inc., Toronto, 2003.

Poolman et al., *Vaccine*, "Developing a nontypeable *Haemophilus influenzae* (NTHi) vaccine", 19 (Suppl. 1):S108-S115 (2001).

Risberg et al., *Eur. J. Biochem.*, "Structural analysis of the lipopolysaccharide oligosaccharide epitopes expressed by a capsule-deficient strain of *Haemophilus influenzae* Rd", 261:171-180 (1999).

Ruffolo et al., *Infect. Immun.*, "Identification, Purification, and Characterization of the Type 4 Fimbriae of *Pasteurella multocida*", 65:339-343 (1997).

Semmler et al., *Microbiology*, "A re-examination of twitching motility in *Pseudomonas aeruginosa*", 145:2863-2873 (1999).

Skerker and Berg, *Proc. Nat'l. Acad. Sci. USA*, "Direct observation of extension and retraction of type IV pili", 98:6901-6904 (2001).

Snow et al., *Otol. Neurotol.*, "Progress in the Prevention of Otitis Media through Immunization", 23:1-2 (2002).

Spinola et al., *J. Infect. Dis.*, "Epidemiology of Colonization of Nontypable *Haemophilus influenzae* in Children: A Longitudinal Study", 154:100-109 (1986).

Stevenson et al., *Vet. Microbiol.*, "Cloning and characterisation of type 4 fimbrial genes from *Actinobacillus pleuropneumoniae*", 92:121-134 (2003).

Strom and Lory, *Annu. Rev. Microbiol.*, "Structure-Function and Biogenesis of the Type IV Pili", 47:565-596 (1993).

St. Geme III, *Cell Microbiol.*, "Molecular and cellular determinants of non-typeable *Haemophilus influenzae* adherence and invasion", 4:191-200 (2002).

Suzuki and Bakaletz, *Infect. Immun.*, "Synergistic Effect of Adenovirus Type 1 and Nontypeable *Haemophilus influenzae* in a Chinchilla Model of Experimental Otitis Media", 62:1710-1718 (1994).

Swiss Prot Accession No. P31768, Jul. 1, 1993.

Swiss Prot Accession No. P31769, Jul. 1, 1993.

Swiss Prot Accession No. P31770, Jul. 1, 1993.

Swiss Prot Accession No. P31771, Jul. 1, 1993.

Swiss Prot Accession No. P31772, Jul. 1, 1993.

Swiss Prot Accession No. P31773, Jul. 1, 1993.

Teele et al., *J. Infect. Dis.*, "Otitis Media in Infancy and Intellectual Ability, School Achievement, Speech, and Language at Age 7 Years", 162:685-694 (1990).

Tønjum and Koomey, *Gene*, "The pilus colonization factor of pathogenic neisserial species : organelle biogenesis and structure/function relationships—a review", 192:155-163 (1997).

Wall and Kaiser, *Mol. Microbiol.*, "Type IV pili and cell motility", 32:1-10 (1999).

Watson et al., *Gene*, "Identification of a gene, *pilF*, required for type 4 fimbrial biogenesis and twitching motility in *Pseudomonas aeruginosa*", 180:49-56 (1996).

Wolfgang et al., *EMBO J.*, "Components and dynamics of fiber formation define a ubiquitous biogenesis pathway for bacterial pili", 19:6408-6418 (2000).

Zhang et al., *FEMS Microbiol Lett.*, "Identification of type 4 fimbriae in *Actinobacillus pleuropneumoniae*", 189:15-18 (2000).

Zwahlen et al., *Infect. Immun.*, "Participation of Complement in Host Defense Against Capsule-Deficient *Haemophilus influenzae*", 42:708-715 (1983).

Microbial-Pathogenesis.org, "The Genomic Sequence of an Otitis Media Isolate of Nontypeable *Haemophilus influenzae*" (http://www.microbial-pathogenesis.org).

* cited by examiner

Figure 1

HAEMOPHILUS INFLUENZAE TYPE IV PILI

This application claims priority to U.S. Provisional Patent Application No. 60/532,296, filed Dec. 23, 2003. This application is incorporated by reference herein in its entirety.

Experimental work relating to the invention described herein was supported by grants R01 DC03915 and R01 DC005980 from the NIH/NIDCD. The United States government may have certain rights in the invention.

FIELD OF THE INVENTION

The invention described herein relates to a *Haemophilus influenzae* (*H. influenzae*) regulon encoding type IV pili. In particular, the invention relates to type IV pili from nontypeable *H. influenzae* (NTHi) and from *H. influenzae* strains a, b, c, e and f. The invention provides isolated *H. influenzae* pilus polynucleotides and polypeptides encoded by the polynucleotides as well as polynucleotides and polypeptides encoded by the polynucleotides involved in the assembly/disassembly of the structure. The invention also relates to uses of these polynucleotides and/or polypeptides including methods for eliciting an immune response to *H. influenzae* and methods of treating and preventing *H. influenzae* related pathological conditions.

BACKGROUND

The clinical term for middle ear infections is otitis media (OM). According to Klein, *Vaccine*, 19 (Suppl. 1): S2-S8, 2000, OM is the most common reason for an ill child to obtain healthcare and for a child in the United States to receive antibiotics or undergo a general anesthetic. Statistics indicate that 24.5 million physician office visits were made for OM in 1990, representing a greater than 200% increase over those reported in the 1980s. While rarely associated with mortality, the morbidity associated with OM is significant. Hearing loss is a common problem associated with this disease, often affecting a child's behavior, education and development of language skills (Baldwin, *Am. J. Otol.*, 14: 601-604, 1993; Hunter et al., *Ann. Otol. Rhinol. Laryngol. Suppl.*, 163: 59-61, 1994; Teele et aL, *J. Infect. Dis.*, 162: 685-694, 1990). The socioeconomic impact of OM is also great, with direct and indirect costs of diagnosing and managing OM exceeding $5 billion annually in the U.S. alone (Kaplan et al., *Pediatr. Infect. Dis. J.*, 16: S9-11, 1997).

OM is thought to result from infectious, environmental and host genetics factors. Bacteria such as *Haemophilus influenzae*, *Streptococcus pneumoniae* and *Moraxella catarrhalis* are the most common infectious organisms in OM. Acute OM is a disease characterized by rapid onset and short duration of signs and symptoms of inflammation in the middle ear, while chronic OM refers to a condition that is defined by the relatively asymptomatic presence of fluid (or effusion) in the middle ear. However, in chronic OM, despite the absence of certain signs of acute infection (i.e., ear pain or fever), these abnormal middle ear fluids can persist for periods exceeding three months. Treatment of acute OM by antibiotic therapy is common, but antibiotic-resistant bacteria have emerged. Surgical management of chronic OM involves the insertion of tympanostomy tubes through the tympanic membrane of the ear while a child is under general anesthesia. While this procedure is commonplace (prevalence rates are ~13%; Bright et al., *Am. J. Public Health*, 83(7): 1026-8, 1993) and is highly effective in terms of relieving painful symptoms by draining the middle ear of accumulated fluids, it is invasive and carries incumbent risks (Berman et al., *Pediatrics*, 93(3): 353-63, 1994; Bright et al., supra.; Cimons, *ASM News*, 60: 527-528; Paap, *Ann. Pharmacother.*, 30(11): 1291-7, 1996). There is thus a need for additional approaches to the management and, preferably, the prevention of OM.

OM vaccine development is most advanced for *S. pneumoniae*, the primary causative agent of acute OM (AOM), as evidenced by the recent approval and release of a seven-valent capsular-conjugate vaccine, PREVNAR® (Eskola and Kilpi, *Pedriatr. Infect. Dis. J.* 16: S72-78, 2000). While PREVNAR® has been highly efficacious for invasive pneumococcal disease, coverage for OM has been disappointing (6-8%) with reports of an increased number of OM cases due to serotypes not included in the vaccine (Black et al., *Pedriatr. Infect. Dis J*, 19: 187-195, 2000; Eskola et al., *Pedriatr. Infect. Dis J.*, 19: S72-78, 2000; Eskola et al., *N. Engl. J. Med.*, 344: 403-409, 2001; Snow et al., *Otol. Neurotol.*, 23: 1-2, 2002).

*H. infiuenzae* is a gram-negative bacterium that, as noted above, plays a role in OM. Clinical isolates of *H. influenzae* are classified either as serotypes "a" through "f" or as non-typeable depending on the presence or absence, respectively, of type-specific polysaccharide capsules on the bacteria. A vaccine for *H. influenzae* type b has been developed. Like Prevnar®, the type b *H. influenzae* vaccines target the polysaccharide capsule of this organism and thus the vaccine is comprised of capsule polysaccharide that has been conjugated to a protein carrier. Less progress has been made for a vaccine for non-typeable *H. influenzae* (NTHi) which causes approximately 20% of acute OM in children and predominates in chronic OM with effusion (Coleman et al., *Inf and Immunity*, 59(5), 1716-1722, 1991; Klein, *Pedriatr. Infect. Dis J.*, 16, S5-8, 1997; Spinola et al., *J. Infect. Dis.*, 154, 100-109, 1986). NTHi can also cause pneumonia, sinusitis, septicemia., endocarditis, epiglottitis, septic arthritis, meningitis, postpartum and neonatal infections, postpartum and neonatal sepsis, acute and chromic salpingitis, epiglottis, pericardis, cellulitis, osteomyclitis, endocarditis, cholecystitis, intraabdorninai infections, urinary tract infection, mastoiditis, aortic graft infection, conjunctitivitis, Brazilian purpuric fever, occult bacteremia and exacerbation of underlying lung diseases such as chronic bronchitis, bronchietasis and cystic fibrosis. A prototype NTHi isolate is the low passage isolate 86-028NP which was recovered from a child with chronic OM. This strain has been well characterized in vitro (Bakaletz et al., *Infect. Immun.*, 53: 331-5, 1988; Holmes et al., *Microb. Pathog.*, 23: 157-66, 1997) as well as in a chinchilla OM model (Bakaletz et at., *Vaccine*, 15: 955-61, 1997; Suzuki et al., *Infect. Immun.*, 62: 1710-8, 1994; DeMaria et al., *Infect. Immun.*, 64: 5187-92, 1996). The NTHi strain 86-026NP was deposited with the American Type Culture Collection, 10801 University Blvd., Manassas, Va. 20110, on Oct. 16, 2001 and assigned accession no. PTA-4764. A contig set from the genome of stain 86-028NP can be found at the Microbial-Pathogenesis.org web site of Children's Hospital, Columbus, Ohio.

Adherence and colonization are acknowledged first steps in the pathogenesis of *H. influenzae*. As such, *H. influenzae* express multiple adhesins including hemagglutinating pili, fimbriae and non-fimbrial adhesins (Gilsdorf et al., *Pediatr Res* 39, 343-348, 1996; Gilsdorf., *Infect. Immun.*, 65, 2997-3002, 1997; and St. Geme III, *Cell. Microbiol.*, 4, 191-200, 2002). Notably, none of the adhesins described have previously been associated with a motility function. Moreover, *H. influenzae* do not express flagella with are also associated with motility. Twitching motility is a flagella-independent form of bacterial translocation over moist surfaces and occurs by extension, tethering, and then retraction of polar structures known as type IV pili (Bardy., *Microbiology*, 149, 295-304, 2003; Tonjum and Koomey, *Gene*, 192, 155-163, 1997; Wolfgang et al, *EMBO J.*, 19, 6408-6418,; Mattick, *Annu. Rev. Microbiol.*, 56, 289-314, 2002). Type IV pili are typically 5-7 nm in diameter, several micrometers in length and comprised of a single protein subunit assembled into a helical conformation with 5 subunits per turn (Bardy et al., *Microbiology*, 149, 295-304, 2003; Wall and Kaiser, *Mol. Microbiol.*, 32, 1-10, 1999). Type IV pilin subunits are usually 145-160 amino acids in length and may be glycosylated or phosphorylated. There are two classes of pilin subunits, IVa and IVb, which are distinguished from one another by the average length of the leader peptide and the mature subunit, which N-methylated amino acid occupies the N-terminal position of the mature protein, and the average length of the D-region (for disulfide region). Most of the respiratory pathogens express class IVa pilins, whereas the enteropathogens more typically express class IVb pilins. Type IVa pili are distinguished by the presence of a highly conserved, hydrophobic N-terminal methylated phenylalanine.

Type IV pili serve as a means of rapid colonization of new surfaces. Thus type IV pilus experssion is important to both adherence and biofilm formation by many bacteria (Mattick, *Annu. Rev. Microbiol.*, 56, 289-314 2002; O'Toole and Kolter, *Mol. Microbiol.*, 30, 295-304, 1998; Klausen et al., *Mol. Microbiol.*, 50, 61-68, 2003; Jesaitis et al., *J. Immunol.*, 171, 4329-4339, 2003), as well as virulence of *Neisseria* species, *Moraxella bovis*, *Vibrio cholerae*, enteropathogenic *Escherichia coli* and *Pseudomonas aeruginosa*, among others (O'Toole and Kolter, supra; Klausen et al., supra; Klausen et al., *Mol. Microbiol.*, 48, 1511-1524, 2003; Strom and Lory, *Annu. Rev. Microbiol.*, 47, 565-596, 1993). A biofilm is a complex organization of bacteria that are anchored to a surface via a bacterially extruded exopolysaccharide matrix. The matrix envelopes the bacteria and protects it from the human immune system. Ehrlich et al., *JAMA*, 287(13), 1710-1715 (2002) describes biofilm formation by *H. influenzae*. It has been postulated that blocking the interaction between type IV pili and the human body can avoid or stop the bacterial infection (Meyer et al., U.S. Pat. No. 6,268,171 issued Jul. 31, 2001).

Type IV pilus expression is a complex and highly regulated bacterial function. In *P. aeruginosa*, the biogenesis and function of type IV pili is controlled by over forty genes (Strom and Lory, supra). To date, only a subset of the vast number of related type IV pilus genes (Tonjum and Koomey, supra; Darzins and Russell, *Gene*, 192, 109-115, 1997) have been found in several members of the HAP (*Haemophilus*, *Actinobacillus* and *Pasteurella*) family (Stevenson et al., *Vet. Microbiol.*, 92, 121-134, 2003; Doughty et al., *Vet. Microbiol.*, 72, 79-90, 2000; Dougherty and Smith, *Microbiology*, 145, 401-409 1999), but neither expression of type IV pil nor twitching motility has ever been described for any *H. influenzae* isolate. In fact, *H. influenzae* is classically described as a bacterium that does not express these structures (Friedrich et al. *Appl. Environ. Microbiol.*, 69, 3695-3700, 2003; Fussenegger et al., *Gene*, 192, 125-134, 1997), despite the presence of a cryptic gene cluster within the strain Rd genome (Fleischmann et al., *Science*, 269, 496-512, 1995). Strain Rd is a non-encapsulated derivative of an *H. influenzae* serotype d organism (Zwahlen et al., *Infect. Immun.*, 42, 708-715, 1983; Bendler and Goodgal, *J. Microbiol.*, 70, 411-422, 1972; Risberg et al., *Eur. J. Biochem.*, 261, 171-180, 1999). Although strain Rd has some virulence properties, serotype d strains are generally considered to be commensals; they do not frequently cause disease (Daines et al., *J. Med. Microbiol.*, 52, 277-282, 2003). It is therefore important to make the distinction between disease-causing strains of *H. influenzae* and strain Rd.

SUMMARY OF THE INVENTION

The present invention relates to Type IV pilus gene clusters of *H. influenzae*, in particular non-typeable *H. influenzae* (NTHi) and *H. influenzae* strains a, b, c, e and f.

Polynucleotides and Polypeptides of the Invention

The present invention provides *H. influenzae* polynucleotides and particularly open reading frames from a regulon arranged in two gene clusters plus one other gene. The regulon includes a gene (pilA) that encodes the major subunit of a heretofore uncharacterized *H. influenzae* type IV pilus. The regulon includes polynucleotides from a gene cluster encoding pilin polypeptides PilA (major pilin subunit), PilD (leader peptidase), PilB and PilC (involved in the assembly/disassembly of the pilin structure); another gene cluster encoding ComA, ComB, ComC, ComD, ComE, and ComF (involved in competence for transformation and pilus expression); and a gene encoding PilF (required for type IV pilus biogenesis) (Watson et al, *Gene*, 49: 56, 1996). In one embodiment, the pilus regulon is that of NTHi *H. influenzae* strain 86-028NP.

Polynucleotides encoding the NTHi 86-028NP pilin polypeptides set out in the following SEQ ID NOs are provided by the invention: PilA polypeptide in SEQ ID NO: 2, PilB polypeptide in SEQ ID NO: 4, PilC polypeptide in SEQ ID NO: 6, PilD polypeptide in SEQ ID NO: 8, ComA polypeptide in SEQ ID NO: 10, ComB polypeptide in SEQ ID NO: 12, ComC polypeptide in SEQ ID NO: 14, ComD polypeptide in SEQ ID NO: 16, ComE polypeptide in SEQ ID NO: 18, ComF polypeptide in SEQ ID NO: 20 and PilF polypeptide in SEQ ID NO: 22. Alternative codon usage is thus specifically contemplated by the invention. In one embodiment, the polynucleotides comprise the NTHi 86-028NP gene sequences set out in the following SEQ ID NOs which respectively encode the foregoing polypeptides: pilA in SEQ ID NO: 1, pilB in SEQ ID NO: 3, pilC in SEQ ID NO: 5, pilD in SEQ ID NO: 7, comA in SEQ ID NO: 9, comB in SEQ ID NO: 11, comC in SEQ ID NO: 13, comD in SEQ ID NO: 15, comE in SEQ ID NO: 17, comF in SEQ ID NO: 19; and pilF in SEQ ID NO: 21. Each of the polynucleotide sequences includes a final three nucleotides representing a stop codon.

Also provided are polynucleotides encoding PilA polypeptides from NTHi clinical isolates 1728MEE, 1729MEE, 3224A, 10548MEE, 1060MEE, 1885MEE, 1714MEE, 1236MEE, 1128MEE and 214NP. The amino acid sequences of these PilA polypeptides are set out in SEQ ID NOs: 26, 28, 30, 32, 34, 36, 38, 40, 42 and 44, respectively. Again, the possibility of alternative codon usage is specifically contemplated in polynucleotides encoding the polypeptides. In one embodiment, the polypeptides are respectively encoded by the nucleotide sequences set out in SEQ ID NOs: 25, 27, 29, 31, 33, 35, 37, 39, 41 and 43.

The invention provides for polynucleotides that hybridize under stringent conditions to (a) the complement of the nucleotide sequences set out in SEQ ID NOs: 1, 3, 5, 7, 9, 11, 13, 15, 17, 19, 21, 25, 27, 29, 31, 33, 35, 37, 39, 41 or 43; (b) a polynucleotide which is an allelic variant of any polynucleotides recited above; (c) a polynucleotide which encodes a species homolog of any of the proteins recited above; or (d) a polynucleotide that encodes a polypeptide comprising a specific domain or truncation of the polypeptides of the present invention. Type IV pilin polynucleotides from other non-typeable *H. influenzae* strains and from *H. influenzae* strains a, b, c, e and f are specifically contemplated. These polynucleotides can be identified and isolated by techniques standard in the art such as hybridization and polymerase chain reaction using part or all of the polynucleotides of SEQ ID NOs: 1, 3, 5, 7, 9, 11, 13, 15, 17, 19, 21, 25, 27, 29, 31, 33, 35, 37, 39, 41 or 43 as probes or primers, respectively.

The polynucleotides of the invention also include nucleotide sequences that are substantially equivalent to the polynucleotides recited above. Polynucleotides according to the invention can have, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to the NTHi polynucleotides recited above.

Included within the scope of the nucleic acid sequences of the invention are nucleic acid sequence fragments that hybridize under stringent conditions to the NTHi nucleotide sequences of SEQ ID NOs: 1, 3, 5, 7, 9, 11, 13, 15, 17, 19, 21, 25, 27, 29, 31, 33, 35, 37, 39, 41 or 43, or complements thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated. These nucleic acid sequence fragments capable of specifically hybridizing to a NTHi polynucleotide of the invention can be used as probes to detect NTHi polynucleotides of the invention and/or can differentiate NTHi polynucleotides of the invention from other bacterial genes, and are preferably based on unique nucleotide sequences.

The term "stringent" is used herein to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, 2$^{nd}$ Ed., Cold Spring Harbor Laboratory, (Cold Spring Harbor, N.Y. 1989).

More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., *Nucleic Acid Hybridisation: A Practical Approach*, Ch. 4, IRL Press Limited (Oxford, England). Hybridization conditions can be adjusted by one skilled in the art in order to accommodate these variables and allow DNAs of different sequence relatedness to form hybrids.

As noted above, polynucleotides contemplated by the present invention are not limited to the specific polynucleotides of SEQ ID NOs: 1, 3, 5, 7, 9, 11, 13, 15, 17, 19, 21, 25, 27, 29, 31, 33, 35, 37, 39, 41 or 43, but also include, for example, allelic and species variations thereof. Allelic and species variations can be routinely determined by comparing the sequence provided in SEQ ID NOs: 1, 3, 5, 7, 9, 11, 13, 15, 17, 19, 21, 25, 27, 29, 31, 33, 35, 37, 39, 41 or 43, preferably the open reading frames therein, a representative fragment thereof, or a nucleotide sequence at least 90% identical, preferably 95% identical, to the open reading frames within SEQ ID NOs: 1, 3, 5, 7, 9, 11, 13, 15, 17, 19, 21, 25, 27, 29, 31, 33, 35, 37, 39, 41 or 43 with a sequence from another isolate of the same species or another species. Preferred computer program methods to determine identity and similarity between two sequences include, but are not limited to, the GCG program package, including GAP (Devereux et al., *Nuc. Acid. Res.*, 12: 387, 1984; Genetics Computer Group, University of Wisconsin, Madison, Wis.), BLASTP, BLASTN, and FASTA (Altschul et al., *J. Mol. Biol.*, 215: 403-410, 1990). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well known Smith-Waterman algorithm may also be used to determine identity.

Polynucleotides of the invention may be isolated from natural sources or may be synthesized by standard chemical techniques, e.g., the phosphotriester method described in Matteucci et al., *J. Am Chem Soc.*, 103: 3185 (1981).

Antisense polynucleotides complementary to the polynucleotides encoding the pilus polypeptides of the invention are also provided.

Polypeptides of the invention include pilin polypeptides PilA, PilD, PilB, PilC, ComA, ComB, ComC, ComD, ComE, ComF and PilF. In one embodiment the polypeptides comprise the NTHi 86-028NP amino acid sequences respectively set out in SEQ ID NO: 2, 4, 6, 8, 10, 12, 14, 16, 18, 20 or 22. Polypeptides of the invention also include PilA polypeptides set out in SEQ ID NOs: 26, 28, 30, 32, 34, 36, 38, 40, 42 or 44. In additional embodiments, the Type IV pilin polypeptides of the invention are those of other non-typeable *H. influenzae* strains and from *H. influenzae* strains a, b, c, e and f.

Polypeptides of the invention specifically include peptide fragments (i.e., peptides) that retain one or more biological or immunogenic properties of a full length polypeptide of the invention. In one embodiment PilA peptide fragments provided by the invention are designated TfpQ2, TFPQ3, TfpQ4 and OLP3 and respectively comprise amino acids 35 through 68 of SEQ ID NO: 2, amino acids 69 through 102 of SEQ ID NO: 2, amino acids 103 through 137 of SEQ ID NO: 2, and amino acids 21 through 35 of SEQ ID NO: 2.

The invention also provides for polypeptides with one or more conservative amino acid substitutions that do not affect the biological and/or immunogenic activity of the polypeptide. Alternatively, the polypeptides of the invention are contemplated to have conservative amino acids substitutions which may or may not alter biological activity. The term "conservative amino acid substitution" refers to a substitution of a native amino acid residue with a nonnative residue, including naturally occurring and nonnaturally occurring amino acids, such that there is little or no effect on the polarity or charge of the amino acid residue at that position. For example, a conservative substitution results from the replacement of a non-polar residue in a polypeptide with any other non-polar residue. Further, any native residue in the polypeptide may also be substituted with alanine, according to the methods of "alanine scanning mutagenesis". Naturally occurring amino acids are characterized based on their side chains as follows: basic: arginine, lysine, histidine; acidic: glutamic acid, aspartic acid; uncharged polar: glutamine, asparagine, serine, threonine, tyrosine; and non-polar: phenylalanine, tryptophan, cysteine, glycine, alanine, valine, proline, methionine, leucine, norleucine, isoleucine General rules for amino acid substitutions are set forth in Table 1 below.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asn |
| Gly | Pro, Ala | Ala |
| His | Asn, Gln, Lys, Arg | Arg |
| Ile | Leu, Val, Met, Ala, Phe, | Leu |
| Leu | Norleucine, Ile, Val, Met, | Leu |
| Lys | Arg, 1,4 Diaminobutyric | Arg |
| Met | Leu, Phe, Ile | Leu |
| Phe | Leu, Val, Ile, Ala, Tyr | Arg |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, | Leu |

The invention also provides variants of the polypeptides of the present invention (e.g., a polypeptide exhibiting at least about 65%, at least about 70%, at least about 75%, at least about 80%, at least about 85%, 86%, 87%, 88%, 89%, at least about 90%, 91%, 92%, 93%, 94%, typically at least about 95%, 96%, 97%, more typically at least about 98%, or most typically at least about 99% amino acid identity to a polypeptide of SEQ ID NO: 2, 4, 6, 8, 10, 12, 14, 16, 18, 20 or 22) that retain biological and/or immunogenic activity.

The invention contemplates that polynucleotides of the invention may be inserted in a vector for amplification or expression. For expression, the polynucleotides are operatively linked to appropriate expression control sequences such as promoter and polyadenylation signal sequences. Further provided are host cells comprising polynucleotides of the invention. Exemplary prokaryotic host cells include bacteria such as E. coli, Bacillus, Streptomyces, Pseudomonas, Salmonella and Serratia. Methods of producing polypeptides of the invention by growing the host cells and isolating polypeptide from the host cells or growth medium are specifically contemplated. One or more polynucleotides from the pilus regulon may be expressed in a host cell. For example, expression of the pilA gene alone and expression of multiple polynucleotides from the pilus regulon in order to affect assembly of the native pili structure are both specifically contemplated. Alternatively, polypeptides of the invention can be prepared by chemical synthesis using standard means. Particularly convenient are solid phase techniques (see, e.g., Erikson et al., The Proteins (1976) v. 2, Academic Press, New York, p. 255). Automated solid phase synthesizers are commercially available. In addition, modifications in the sequence are easily made by substitution, addition or omission of appropriate residues. For example, a cysteine residue may be added at the carboxy terminus to provide a sulfhydryl group for convenient linkage to a carrier protein, or spacer elements, such as an additional glycine residue, may be incorporated into the sequence between the linking amino acid at the C-terminus and the remainder of the peptide.

The term "isolated" refers to a substance removed from, and essentially free of, the other components of the environment in which it naturally exists. For example, a polypeptide is separated from other cellular proteins or a DNA is separated from other DNA flanking it in a genome in which it naturally occurs.

Antibodies

The invention, provides antibodies which bind to antigenic epitopes unique to (i.e., are specific for) H. influenzae pilus polypeptides of the invention. Also provided are antibodies which bind to antigenic epiropes common among multiple H. influenzae subtypes but unique with respect to any other antigenic epitopes. The antibodies may be polyclonal antibodies, monoclonal antibodies, antibody fragments which retain their ability to bind their unique epitope (e.g., Fv, Fab and F(ab)2 fragments), single chain antibodies and human or humanized antibodies. Antibodies may be generated by techniques standard in the art using pilin polypeptide(s) of the invention or host cells expressing pilin polypeptide(s) of the invention as antigens.

The present invention provides for antibodies specific for the pilin polypeptides of the present invention and fragments thereof, which exhibit the ability to kill both H. influenzae bacteria and to protect humans from infection. The present invention also provides for antibodies specific for the polypeptides of the invention which reduce the virulence, inhibit adherence, inhibit biofilm formation, inhibit twitching motility, inhibit cell division, and/or inhibit penetration into the epithelium of H. influenzae bacteria and/or enhance phagocytosis of the H. influenzae bacteria.

In vitro complement mediated bactericidal assay systems (Musher et al., Infect. Immun. 39: 297-304, 1983; Anderson et al., J. Clin. Invest. 51: 31-38, 1972) may be used to measure the bactericidal activity of anti-pilus antibodies.

It is also possible to confer short-term protection to a host by passive immunotherapy via the administration of preformed antibody against an H. influenzae polypeptide of the invention. Thus, antibodies of the invention may be used in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals subject to special risks.

In another embodiment, antibodies of the invention may be used in the production of anti-idiotypic antibody, which in turn can be used as an antigen to stimulate an immune response against pilin epitopes.

Methods for Eliciting an Immune Response and Compositions Therefor

The invention contemplates methods of eliciting in an individual an immune response to one or more H. influenzae type IV pilus polypeptides. In certain embodiments, the methods elicit an immune response to the PilA protein. These methods elicit one or more immune responses, including but not limited to, immune responses which inhibit bacterial replication, immune responses which block H. influenzae adherence to cells, immune responses which prevent H. influenzae twitching and immune responses which prevent biofilm formation. In one embodiment, the methods comprise a step of administering an immunogenic dose of a composition comprising one or more polypeptides of the invention. In another embodiment, the methods comprise administering an immunogenic dose of a composition comprising a cell expressing one or more polypeptides of the invention. In yet another embodiment, the methods comprise administering an immunogenic dose of a composition comprising one or more polynucleotides encoding one or more polypeptides of the invention. The polynucleotide may be a naked polynucleotide not associated with any other nucleic acid or may be in a vector such as a plasmid or viral vector (e.g., adeno-associated virus vector or adenovirus vector). The methods may be used in combination in a single individual. The methods may be used prior or subsequent to *H. influenzae* infection of an individual.

In one embodiment of methods of the invention, a composition of the invention is administered as a priming dose followed by one or more booster doses. Co-administration of proteins or polypeptides that beneficially enhance the immune response such as cytokines (e.g., IL-2, IL-12, GM-CSF), cytokine-inducing molecules (e.g. Leaf) or costimulatory molecules is also contemplated.

An "immunogenic dose" of a composition of the invention is one that generates, after administration, a detectable humoral (antibody) and/or cellular (T cell) immune response in comparison to the immune response detectable before administration or in comparison to a standard immune response before administration. The invention contemplates that the immune response resulting from the methods may be protective and/or therapeutic. In a preferred embodiment, the antibody and/or T cell immune response protects the individual from *H. influenzae* infection, particularly infection of the middle ear and/or the nasopharynx or lower airway. In this use, the precise dose depends on the patient's state of health and weight, the mode of administration, the nature of the formulation, etc., but generally ranges from about 1.0 μg to about 5000 μg per 70 kilogram patient, more commonly from about 10 to about 500 μg per 70 kg of body weight.

Humoral immune response may be measured by many well known methods, such as Single Radial Immunodiffussion Assay (SRID), Enzyme Immunoassay (EIA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

The invention correspondingly provides compositions suitable for eliciting an immune response to pilus polypeptides of the invention. As noted above, the compositions comprise one or more pilus polypeptides, cells expressing one or more polypeptides, or one or more polynucleotides encoding one or more pilus polypeptides. The compositions may also comprise other ingredients such as carriers and adjuvants.

In compositions of the invention, a pilus polypeptide may be fused to another protein when produced by recombinant methods. In one embodiment, the other protein may not, by itself, elicit antibodies, but it stabilizes the first protein and forms a fusion protein retaining immunogenic activity. In another embodiment, the fusion protein comprises another protein that is immunogenic, such as Glutathione-S-transferase (GST) or beta-galactosidase, relatively large co-proteins which solubilize the fusion protein and facilitate production and purification thereof. The other protein may act as an adjuvant in the sense of providing a generalized stimulation of the immune system. The other protein may be fused to either the amino or carboxy terminus of the NTHi protein of the invention.

In other compositions of the invention, pilus polypeptides may be otherwise linked to carrier substances. Any method of creating such linkages known in the art may be used. Linkages can be formed with heterobifunctional agents that generate a disulfide link at one functional group end and a peptide link at the other, such as a disulfide amide forming agent, e.g., N-succidimidyl-3-(2-pyridyldithio)proprionate (SPDP) (See, e.g., Jansen et al., *Immun. Rev.* 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl)cyclohexane-1-carboxylic acid and the like, and coupling agent which activate carboxyl groups by combining them with succinimide or 1-hydroxy-2-nitro-4-sulfonic acid, for sodium salt such as succinimmidyl 4-(N-maleimido-methyl)cyclohexane-1-carobxylate (SMCC).

The pilus polypeptides may be formulated as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

Compositions of the invention may further comprise adjuvants. Known adjuvants include, for example, emulsions such as Freund's Adjuvants and other oil emulsions, *Bordetella pertussis*, MF59, purified saponin from *Quillaja saponaria* (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

Compositions of the invention are typically formulated as injectables, either as liquid solutions or suspensions; solid forms suitable for solution in, or suspension in, liquid prior to injection may also be prepared. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants, which enhance the effectiveness of the vaccine. The vaccines are conventionally administered parenterally, by injection, for example, either subcutaneously or intramuscularly.

Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Compositions may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazenes polyphosphatazanes are useful for both transdermal and transmucosal administration. Polymeric complexes comprising synthetic poly-omithate, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-(dioleyl-dihydroxypropyl)-N,N,N,-trimethylammonium-methyl sulfate (DOTAP), dioleyloxy-propyl-trimethylammonium chloride DOTMA, dimystyloxypropyl-3-dimethyl-hydroxyethyl ammonium (DMRIE), dimethyldioctadecyl ammonium bromide (DDAB) and 9N(N',N-dimethylaminoethane) carbamoyl) cholesterol (DC-Chol). The combination of helper lipids and liposomes will enhance up-take of the liposomes through the skin. These helper lipids include, dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

Formulations may be presented in unit-dose or multi-dose containers, for example, sealed ampules and vials and may be stored in a freeze-dried condition requiring only the addition of the sterile liquid carrier immediately prior to use.

Methods of Inhibiting *H. influenzae*

Alternatively, the invention includes methods of inhibiting *H. influenzae* type IV pili function in an individual. The methods comprise administering to the individual, for example, one or more antibodies of the invention; one or more polypeptides of the invention; one or more antisense polynucleotides of the invention; one or more RNAi molecules; and/or one or more small molecules, in an amount that inhibits its function of the pili. In vitro assays may be used to demonstrate the ability to inhibit pili function. Embodiments of these methods include, for example, methods using inhibitors of pilus polyepeptide synthesis and/or pilus assembly, inhibitors of adherence mediated via type IV pili, inhibitors that disrupt existing biofilms mediated by type IV pili, and inhibitors of twitching.

Inhibition is contemplated for any pathological condition involving *H. influenzae*, for example, OM, pneumonia, sinusitis, septicemia, endocarditis, epiglottitis, septic arthritis, meningitis, postpartum and neonatal infections, postpartum and neonatal sepsis, acute and chromic salpingitis, epiglottis, pericardis, cellulitis, osteomyelitis, endocarditis, cholecystitis, intraabdominal infections, urinary tract infection, mastoiditis, aortic graft infection, conjunctitivitis, Brazilian purpuric fever, occult bacteremia and exacerbation of underlying lung diseases such as chronic bronchitis, bronchietasis and cystic fibrosis.

Compositions comprising inhibitors of *H. influenzae* type IV pili function are provided. The compositions may consist of one of the foregoing active ingredients alone, may comprise combinations of the foregoing active ingredients or may comprise additional active ingredients used to treat bacterial infections. As discussed above, the compositions may comprise one or more additional ingredients such as pharmaceutically effective carriers. Also as discussed above, dosage and frequency of the administration of the compositions are determined by standard techniques and depend, for example, on the weight and age of the individual, the route of administration, and the severity of symptoms. Administration of the pharmaceutical compositions may be by routes standard in the art, for example, parenteral, intravenous, oral, buccal, nasal, pulmonary, rectal, intranasal, or vaginal.

Animal Model

Methods of the invention may be demonstrated in a chinchilla model widely accepted as an experimental model for OM. In particular, a chinchilla model of NTHi-induced OM has been well characterized (Bakaletz et al., *J. Infect. Dis.*, 168: 865-872, 1993; Bakaletz and Holmes, *Clin. Diagn. Lab. Immunol.*, 4: 223-225, 1997; Suzuki and Bakaletz, *Infect. Immun.*, 62: 1710-1718, 1994; Mason et al., *Infect. Immun.*, 71:3454-3462, 2003), and has been used to determine the protective efficacy of several NTHi outer membrane proteins, combinations of outer membrane proteins, chimeric synthetic peptide vaccine components, and adjuvant formulations against OM (Bakaletz et al., *Vaccine*, 15: 955-961, 1997; Bakaletz et al., *Infect. Immun.*, 67: 2746-2762, 1999; Kennedy et al., *Infect. Immun.*, 68: 2756-2765, 2000; Kyd et al., *Infect. Immun.*, 66:2272-2278, 2003; Novotny and Bakaletz, *J. Immunol.*, 171, 1978-1983, 2003).

In the model, adenovirus predisposes chinchillas to *H. influenzae*-induced OM media, which allowed for the establishment of relevant cell, tissue and organ culture systems for the biological assessment of NTHi (Bakaletz et al., *J. Infect. Dis.*, 168: 865-72, 1993; Suzuki et al., *Infect. Immunity* 62: 1710-8, 1994). Adenovirus infection alone has been used to assess the transudation of induced serum antibodies into the tympanum (Bakaletz et al., *Clin. Diagnostic Lab Immunol.*, 4(2): 223-5, 1997) and has been used as a co-pathogen with NTHi, to determine the protective efficacy of several active and passive immunization regimens targeting various NTHi outer membrane proteins, combinations of OMPs, chimeric synthetic peptide vaccine components, and adjuvant formulations as vaccinogens against otitis media (Bakaletz et al., *Infect Immunity,* 67(6): 2746-62, 1999; Kennedy et al., *Infect. Immun.,* 68(5): 2756-65, 2000; Novotny et al., *Infect Immunity* 68(4): 2119-28, 2000; Poolman et al., *Vaccine* 19 (Suppl. 1): S108-15, 2000).

Methods of Detecting *H. influenzae* Bacteria

Also provided by the invention are methods for detecting bacteria in an individual. In one embodiment, the methods comprise detecting pili polynucleotides of the invention in a biological sample using primers or probes that specifically bind to the polynucleotides. Detection of the polynucleotide may be accomplished by numerous techniques routine in the art involving, for example, hybridization and/or PCR. In another embodiment, the methods comprise detecting pili polypeptides of the invention in a biological sample using antibodies of the invention that specifically bind to the polypeptides. The antibodies may be used in any immunoassay system known in the art including, but not limited to, radioimmunoassays, ELISA assays, sandwich assays, precipitin reactions, gel diffusion precipitin reactions, immunodiffusion assays, agglutination assays, fluorescent immunoassays, protein A immunoassays and immunoelectrophoresis assays. Biological samples to be utilized in the methods include, but are not limited to, blood, serum, ear fluid, spinal fluid, sputum, urine, lymphatic fluid and cerebrospinal fluid.

BRIEF DESCRIPTION OF THE DRAWINGS

FIG. 1 is an alignment of amino acid sequences of the PilA polypeptides of NTHi Rd, 86-028NP (SEQ ID NO: 2), 1728MEE (SEQ ID NO: 26), 1729MEE (SEQ ID NO: 28), 3224A (SEQ ID NO: 30), 10548MEE (SEQ ID NO: 32), 1060MEE (SEQ ID NO: 34), 1885MEE (SEQ ID NO: 36), 1714MEE (SEQ ID NO: 38), 1236MEE (SEQ ID NO: 40), 1128MEE (SEQ ID NO: 42), 214NP (SEQ ID NO: 44).

DETAILED DESCRIPTION OF THE INVENTION

The following examples illustrate the invention wherein Example 1 describes sequences of NTHi strain 86-028NP type IV pilus genes of the invention and detection of the pilA gene in thirteen clinical *H. influenzae* isolates, Example 2 demonstrates classical type IV pilus-dependent aggregate formation by NTHi strain 86-028NP, Example 3 demonstrates twitching motility in NTHi strain 86-028NP, Example 4 describes observation of type IV pili on NTHi strain 86-928NP by negative staining and transmission electron microscopy, Example 5 describes the generation of a pilA mutant, Example 6 describes experiments in a chinchilla model of infection with NTHi and pilA mutant NTHi, Example 7 describes pilA genes from ten NTHi clinical isolates, Example 8 describes experiments demonstrating an immune response to NTHi pilli in children and Example 9 describes the identification of NTHi peptide fragments for use as immunogens.

EXAMPLE 1

A type IV pilus regulon was identified in an OM isolate of NTHi.

Many strains of NTHi, including strain 86-028NP, do not possess the hif locus required for the expression of hemagglutinating LKP pili (Mhlanga-Murangadurn et al., J. Bacteriol., 180(17), 4693-4703, 1988), yet most form biofilms. Because pili are important to biofilm formation in other bacterial systems, the contig set from the NTHi strain 86-028NP genomic sequencing effort Microbial-Pathogenesis.org web site of Children's Hospital, Columbus, Ohio or co-owned U.S. Ser. No. 60/453,134) was analyzed for genes potentially encoding another type of pilus. The dataset was BLASTed using the tblasn algorithm with default parameters using the *Pseudomonas aeruginosa* proteins annotated as related to the type IV pilus or twitching motility for *P. aeruginosa* including PilQ and PilT at www.*Pseudomonas*.com. The translated polypeptide for the *P. multocida* PilA protein was also used in this search (Doughty et al., Vet. Microbiol., 72, 79-90, 2000).

What initially appeared to be a cryptic type IV pilus gene locus was identified. Specifically, in strain 86-028NP, there are four genes that are highly homologous to those in *H. influenzae* strain Rd, *A. pleuropneumoniae* and *P. multocicla* (Stevenson et al., *Vet. Microbiol.,* 92, 121-134, 2003; Doughty et al., supra; Zhang et al., *FEMS Microbiol Lett,* 189, 15-18, 2000; and Ruffolo et al., *Infect. Immun.,* 65, 339-343, 1997). These genes encode PilA, PilB, PilC and PilD in strain Rd (Dougherty and Smith, *Microbiology,* 145(2), 401-409, 1999).

The NTHi strain 86-028NP regulon includes a gene cluster of polynucleotides encoding pilin polypeptides PilA (major pilin subunit), PilD (leader peptidase), PilB and PilC (contemplated to be transcribed from the same mRNA and to be involved in the assembly/disassembly of the pilin structure); a gene cluster of polynucleotides encoding pilin polypeptides ComA, ComB, ComC, ComD, ComE, and ComF (involved in competence for transformation and pilus expression); and another gene encoding PilF (required for type IV pilus biogenesis). The amino acid sequences of the pilin polypeptides set out in the following SEQ ID NOs: PilA in SEQ ID NO: 2, PilB in SEQ ID NO: 4, PilC in SEQ ID NO: 6, PilD in SEQ ID NO: 8, ComA in SEQ ID NO: 10, ComB in SEQ ID NO: 12, ComC in SEQ ID NO: 14, ComD in SEQ ID NO: 16, ComE in SEQ ID NO: 18, ComF in SEQ ID NO: 20 and PilF in SEQ ID NO: 22. The gene sequences encoding the polypeptides are set out in the following SEQ ID NOs which respectively encode the foregoing polypeptides: pilA in SEQ ID NO: 1, pilB in SEQ ID NO: 3, pilC in SEQ ID NO: 5, pilD in SEQ ID NO: 7, comA in SEQ ID NO: 9, comB in SEQ ID NO: 11, comC in SEQ ID NO: 13, comD in SEQ ID NO: 15, comE in SEQ ID NO: 17, comF in SEQ ID NO: 19; and pilF in SEQ ID NO: 21. Each of the polynucleotides sequences includes a final three nucleotides representing a stop codon.

In gene expression profiling studies employing cDNA microarrays to characterize the regulation of NTHi genes during the development of competence (i.e., the natural ability of NTHi to take up foreign DNA potentially enhancing or expanding its genetic diversity), the com genes as well as the pil genes are up-regulated during competence development.

In a Southern blot experiment using pilA sequences as a probe, thirteen low-passage clinical NTHi OM isolates recovered from patients undergoing tympanostomy and tube insertion for chronic otitis media and one clinical isolate recovered from a patient with cystic fibrosis had a single copy of pilA within their genome. These fourteen total isolates were designated by the following strain numbers, respectively: 86-028NP; 1728MEE; 1729MEE; 1714MEE; 214NP; 1236MEE; 165NP; 1060MEE; 1128MEE; 10548MEE; 3224A; 3185A, 1885MEE and 27W11679INI.

In the experiment, bacterial chromosomal DNA was isolated using a PUREGENE DNA isolation kit from Gentra Systems (Minneapolis, Minn.), digested with MfeI and the digests run on a 0.8% agarose gel. DNA was transferred to a Nytran SuPerCharge membrane using the Turbo Blotter kit (Schleicher & Schuell, Keene, N.H.). The probe was generated by PCR amplification of the coding sequence of the 86-028NPpilA gene using the primers 5'tgtgacacttccgcaaaaa (SEQ ID NO: 23) and 5'taataaaaggaaaatgaatga (SEQ ID NO: 24). The amplicon was purified using a QlAquick PCR purification kit (Qiagen Inc., Valencia, Calif.). Following the manufacturer's directions, 100 ng of purified PCR product was labeled with horseradish peroxidase using the ECL Direct Nucleic Acid Labeling and Detection System (Amersham Biosciences UK Ltd., Little Chalfont, Bucks, UK). Developed blots were exposed to Fuji Super Rx X-ray film (Fuji Photo Film Co., Tokyo, Japan).

The PilA polypeptide of NTHi strain 86-028NP has a predicted and apparent molecular mass of approximately 14 kDa, contains an N-terminal methylated phenylalanine.

EXAMPLE 2

NTHi strain 86-028NP formed classic aggregates in a subagar surface translocation assay and a surface growth assay when grown under conditions of nutrient depletion.

NTHi strain 86-028NP was grown on chocolate agar for 18-20 hours (37° C., 5% $CO_2$, in a humidified atmosphere) prior to all experiments. Subsequently, this organism was inoculated onto either sBHI, a rich medium on which the NTHi grows very well, or a chemically defined medium which supports the growth of *H. influenzae* (Coleman et al. *J. Clin. Micro.*, 41:4408-4410, 2003) that comprised 83% RPMI1640 media (Gibco BRL, Rockville, Md.), sodium pyruvate (87.3 mM) (Gibco BRL), β-NAD (0.0087 mg/ml) (Sigma Chemical Co., St Louis, Mo.), HEME-histidine (0.0175 mg/ml) (Sigma), Uracil (0.087 mg/ml) (Sigma), and inosine (1.75 mg/ml) (Sigma).

Both agars were poured into one of two formats, in sterile 8-well chamber slides (Lab-tech, Naperville, Ill.) or into sterile 35 mm glass petri dishes (Fisher Scientific, location). When the glass slide was separated from the 8-well chamber slides, the agar remained within the chambers, thus enabling use of the "bottom" surface of the agar for inoculation, which is optimal for assay of twitching motility due to the relative smoothness of this surface (Semmler et al., *Microbiology*, 145, 2863-2873, 1999 and Mattick, *Ann. Rev. Microbiol.*, 56, 289-314, 2002). Whereas agars cast into 8-well chamber slides were used to demonstrate a surface growth phenotype, agars poured into the petri dishes were used for demonstration of sub-surface agar translocation (Semmler et al., supra) whereas agars cast into 8-well chamber slides were used to demonstrate agar surface growth phenotype. All assays were repeated a minimum of three times, on separate days.

Agars that had been poured into sterile glass petri dishes were inoculated subsurface with 0.5 µl of a suspension of NTHi grown as described above, using a sterile micropipet tip. Plates were observed after 24 hours incubation (37° C., 5% $CO_2$) and were then held at room temperature (25° C.) for an additional 24 hours prior to re-reading for signs of bacterial translocation between the bottom surface of the agar and the glass petri dish.

On sBHI medium, 24 hours post-inoculation, NTHi was observed to have grown in a small area (~0.5 mm radius) surrounding the inoculation site between the agar and the glass petri dish bottom. After an additional 24 hours, the growth pattern remained similar to that observed at 24 hours. On the chemically defined medium after 24 hours of incubation, growth of NTHi was observed between the agar surface and the glass petri dish bottom, at a distance 2 to 5 mm from the inoculation site. The bacteria had also aggregated into small colonies in a halo-like pattern surrounding the inoculation site. After 48 hours, NTHi had formed a very distinct array of micro-colonies with many occurring at a distance>5 mm from the inoculation site. The formation of micro-satellites up to 5 mm distance from original site of inoculation was a hallmark finding of growth on chemically defined medium and was never seen when strain 86-028NP was grown on rich agar.

Chamber slides were either inoculated with 0.5 ul of a suspension of 18-20 hour chocolate agar-grown NTHi [suspended in sterile pyrogen free saline (American Pharmaceutical Partners Inc., Schaumburg, Ill.)], or a single colony was stabbed for transfer to the surface of the agar with a sterile toothpick.

On sBHI medium, thirty minutes post-inoculation, NTHi appeared in close association with the agar surface and was growing in a sheet-like pattern. At 2.5 hours, approximately 80-90% of the surface area was covered with a thin sheet of bacteria. Also at this time, micro-aggregates of NTHi began to appear. At 6-7 hours post-inoculation, these micro-aggregates were discernable with the naked eye and there were approximately 3-5 micro-aggregates per well. In addition, NTHi were still observed to be growing as a sheet that covered approximately 50-70% of the agar surface. Twenty-four hours after inoculation, NTHi appeared as large single colonies at each inoculation site.

On chemically defined medium, like that observed on sBHI, thirty minutes post-inoculation, NTHi appeared to be growing in sheet, however the density of the bacteria appeared much less than that observed on sBHI agar. At 2.5 hours after inoculation, numerous micro-aggregates were evident throughout the agar surface. In contrast to those noted when NTHi was inoculated onto sBHI agar, these micro-aggregates were larger and much more dense in appearance. Approximately 30-40 micro-aggregates could be seen on each well. There was still a large area of sheet like growth of NTHi at this time point, with approximately 80% of the surface area covered by bacteria. At 6-7 hours post inoculation, the micro-aggregates were larger, denser, and easily seen with the naked eye. Also, areas of radial growth or halos were seen radiating outward from large colonies, similar to the growth patterns described for *Neisseria* and *Pseudomonas* sp. (refs). By this time period, most of the bacteria appeared to be arranged in small clusters or micro-aggregates with a very small proportion seen covering the agar surface as a sheet or monolayer. After 24 hours, there were large single colonies at each inoculation site, however there were also many small satellite colonies present over the entire agar surface, including sites remote from the points of inoculation.

Thus, NTHi strain 86-028NP demonstrates classic aggregate formation, similar to that reported for type IV pilus-expressing *P. aeruginosa* (Semmler et al., *Microbiology*, 145 (10), 2863-2873, 1999), when grown under conditions of nutrient depletion.

EXAMPLE 3

The movement of individual NTHi cells between a glass coverslip and a smooth agar surface was traced by video microscopy. The cells moved at approximately 0.42 µm/sec, consistent with that reported for twitching *P. aeruginosa* (Skerker and Berg, *Proc. Natl. Acad., Sci. USA*, 98, 6901-6904, 2001) and *Neisseria gonorrhoeae* (Merz et al., *Nature*, 207, 98-102, 2000).

A loopful of NTHi stain 86-028NP, grown on chocolate agar at 37° C. and 5% $CO_2$ for 20 hours and then held at ambient temperature for an additional 24 hours, was suspended in sterile water and 0.5 µl of the resulting suspension was placed onto a sterile glass slide. To provide contrast and thus aid visualization, 0.5 μl of trypan blue (0.4%, Sigma, St. Louis Mo.) was added to the bacterial suspension. The droplet was then covered with a sterile coverslip and viewed via light microscope (Axioskope 40, Zeiss, Thornwood, N.Y.). Specimens were observed at room temperature over a period of approximately 15-20 minutes. The bacteria were readily observable and directional movement of several, although not all, cells or microaggregates of cells was noted. In order to stimulate activity, we added 0.5 μl of a heme solution (1 mg/ml) (Sigma, St. Louis, Mo.) to one side of the sterile coverslip. Twitching activity was documented by the capture of both video [video otoscopy system (MEDR$_X$ Inc, Seminole, Fla.) attached to a VCR] and still images in order to determine length and rate of excursions.

Individual cells, or microaggregates of cells, traveled a total linear distance of approximately 11.0 μm over a period of 51 seconds (rate approximately 0.22 μm/sec). However, over the entire period of observation, the rate of twitching motility observed ranged from 0.14 to 0.48 μm/sec.

EXAMPLE 4

Type IV pili were visualized by negative staining and transmission electron microscopy.

Overnight cultures of NTHi strain 86-028NP were inoculated onto sBHI and defined agar plates and incubated for 2, 6 or 24 hours at 37° C., 5% $CO_2$. Additionally, cultures were inoculated into sBHI broth and defined broth and incubated for 2.5 or 5.5 hours. These latter time points represent entry into exponential and lag phases of growth, respectively. Bacteria were then negatively stained using a Whatman-filtered solution containing 2.0% ammonium acetate w/v (Sigma) and 2.0% ammonium molybdate w/v (Sigma) in sterile water (Bakaletz et al. *Infect Immun*, 1988 56:331-5). Formvar- and carbon-coated copper grids, 300 mesh, (Electron Microscopy Sciences) were touched to individual colonies grown on agar plates, and then floated on a droplet of the negative stain solution. Broth-grown cultures were pelleted, the bacteria resuspended in sterile water and grids were floated on equal volumes of bacterial suspension and negative stain. After 5 minutes, grids were blotted and allowed to air dry prior to viewing in an Hitachi Model H-600 transmission electron microscope with attached video monitor (Gatan, Inc., Pleasanton, Calif.) and digital imaging system (Gatan, Inc.).

When NTHi were grown on sBHI, no type IV pilus-like structures were observed. Conversely, when grown under defined nutrient conditions, NTHi was seen to express structures of approximately 6-7 nm diameter. Many of these structures were also found free on the grid surface. There were approximately 5 to 6 pili per bacterial cell and these were polar in location.

EXAMPLE 5

A mutant deficient in the expression of PilA was generated to further characterize components of the structures observed when strain 86-028NP was grown in alkaline conditions on chemically defined media.

The pilA gene and approximately 1 kb 5' and 3' of the gene from strain 86-028NP was amplified by PCR, cloned into pGEM-T Easy (Promega) and the DNA sequence determined to verify that there were no changes in the sequence in the clone as a result of the PCR amplification. As there was no convenient restriction site in the pilA gene, a BamHI site was engineered into the gene using the Stratagene QuikChange Site-Directed Mutagenesis Kit. The resulting construct was linearized with BamHI and the gene was insertionally inactivated with the ΩKn-2 cassette (Perez-Casal et al., *J. Bacteriol.*, 173: 2617-2624, 1991). The resulting construct was linearized and transformed into strain 86-028NP using the MIV method (Poje and Redfield, p. 57-70 in Herbert et al. (Eds.), *Haemophilus influenzae* Protocols, Humana Press Inc., Toronto, 2003). Kanamycin-resistant clones were selected and insertional inactivation of the 86-028NP pilA gene was verified in selected clones by Southern hybridization.

When the pilA mutant was evaluated for expression of type IV pili after growth under conditions that induced the increased expression of type IV pili in the parental isolate (Example 4), no cell-associated or free type IV pili were observed confirming that the pilA gene product (and/or the pilBCD gene products since the mutation is pilA is likely to disrupt the downstream gene products) are required for pilus expression.

EXAMPLE 6

To determine whether type IV pili are necessary for colonization of the nasopharynx, as well as survival in and/or ability to form a biofilm in the middle ear, we challenged fourteen adult chinchillas both intranasally and transbullarly with either the parent strain 86-028NP or with an isogenic pilA mutant (Example 5). On days 2, 5, 10, 15 and 20 post-challenge, nasopharyngeal lavages and epitympanic taps were performed, and both nasal and middle ear mucosae were retrieved from 1-2 chinchillas per cohort to determine cfu of NTHi in each of these anatomic sites. Both the parent and pilA mutant were able to survive in the chinchilla host for twenty days. However, whereas both strains were present in equivalent amounts in lavage and tap fluids, when assayed for an adherent subpopulation in tissue homogenates of nasal mucosae, the pilA mutant was absent from, or below our ability to detect, in 80% of the homogenates recovered after day 5 whereas 87% of similar nasal mucosae recovered from animals challenged with the parental isolate were culture positive.

Confocal microscopy was performed on snap-frozen tissue to determine whether a biofilm was present. The biomass formed by the pilA mutant in the middle ear was of a different character than the well-structured biofilm characteristic of the parental isolate. The data indicate that NTHi type IV pili play a key role in the disease course of OM.

EXAMPLE 7

Figure 1:
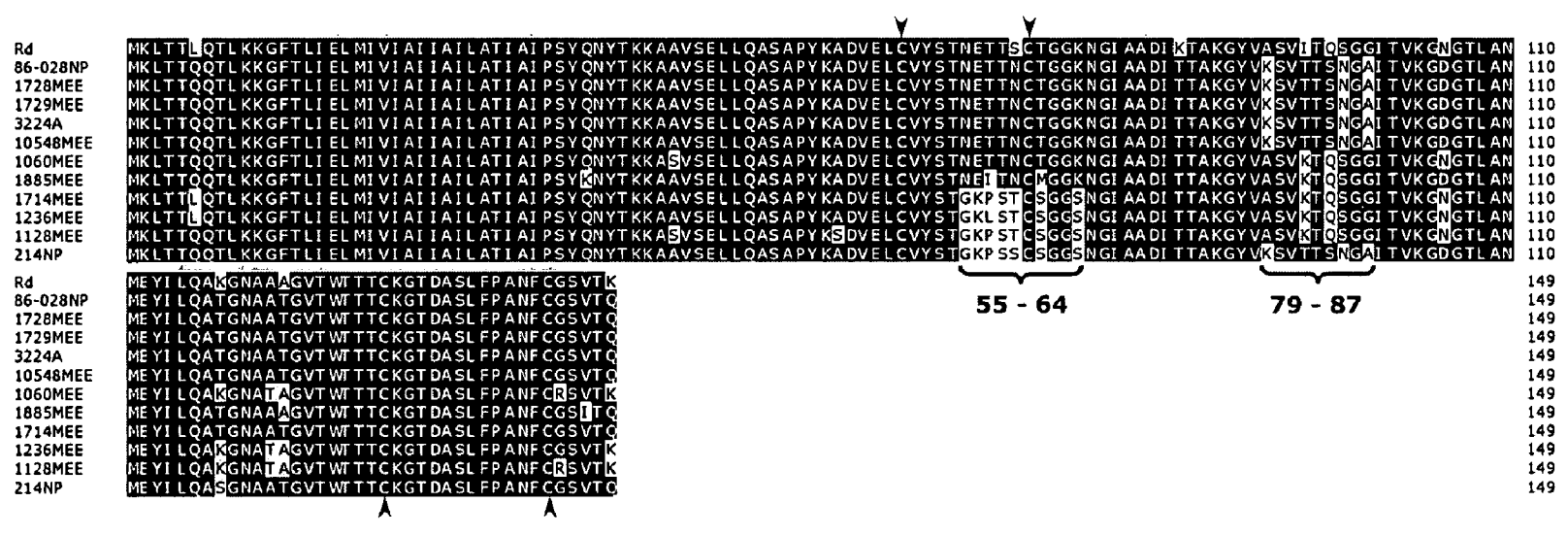

The pilA gene of ten clinical isolates of NTHi have been sequenced. The nucleotide and amino acid sequences from the isolates are respectively set out as follows: 1728MEE in SEQ ID NOs: 25 and 26, 1729MEE in SEQ ID NOs: 27 and 28, 3224A in SEQ ID NOs: 29 and 30, 10548MEE in SEQ ID NOs: 31 and 32, 1060MEE in SEQ ID NOs: 33 and 34, 1885MEE in SEQ ID NOs: 35 and 36, 1714MEE in SEQ ID NOs: 37 and 38, 1236MEE in SEQ ID NOs: 39 and 40, 1128MEE in SEQ ID NOs: 41 and 42, and 214NP in SEQ ID NOs: 43 and 44. An alignment of the amino acid sequences with those of the pilA polypeptides from Rd and 86-028NP is presented in FIG. 1.

The pilA genes of all isolates encode a 12-residue leader peptide that is largely invariant save a Q to L substitution at position 6 in two isolates as well as in strain Rd. Mature PilA contains 137 residues and is predicted to contain a characteristic methylated phenylalanine at position +1. Tyrosine residues at positions +24 and +27, and believed to be involved in subunit-subunit interactions, are highly conserved as are four Cys residues at positions +50, +60,+119 and +132. Interestingly, the NTHi PilA proteins appear to represent a new class of type IV pili. The leader peptide is larger than that characteristic for type IVa pilins (typically 5-6 residues in length), yet shorter than the typical IVb leader peptide (15-30 residues). At 137 residues, the mature NTHi pilin is shorter than either class IVa or IVb pilins (150 and 190 residues, respectively). Since the NTHi PilA proteins begin with an N-methylated phenylalanine, they are more like class IVa pilins however in electron micrographs, free NTHi type IV pili always appear in laterally associated bundles, a phenotype more classically associated with class IVb pilins due to their ability to self-associate through anti-parallel interactions.

In terms of NTHi PilA sequence diversity, overall these sequences are highly homologous. See FIG. 1. Two areas of potentially important diversity, if surface accessible and also targeted for vaccine development due to protective immunodominance or adhesin-binding function, exist at positions 55-64 and 79-87. Within the first region, amongst the clinical isolates, there appears to be two major variants, one representing the majority (seven of eleven isolates, 64%) and characterized by the following sequence: NET/ITNCT/MGGK and the other representing the minority (four of eleven isolates, 36%) and characterized by the sequence: GKP/LST/SCSGGS. There are however some additional minor variations at positions +57 and +61 in the majority grouping and at positions +57 and +59 for the minority grouping. The diversity noted at position +61 is only seen in one isolate to date (strain #1885), wherein there is a T to M substitution. Within the second focused region of diversity (position 79-87), there appears to be two equally distributed variants among the clinical NTHi isolates. The sequence ASVKTQSGG is present in five of eleven clinical isolates (~45%), whereas the sequence KSVTTSNGA is present in six of eleven clinical isolates (~55%).

Overall, of the seven isolates with the majority sequence at position 55-64, five isolates also have the KSVTTSNGA motif at region 79-87, with the remaining two isolates having the ASVKTQSGG motif in this region. Of the four remaining clinical isolates with the minority sequence at position 55-64, three of these also have the ASVKTQSGG motif at region 79-87, with only one isolate having the KSVTTSNGA sequence in this domain. Thereby, depending on whether or not these are conservative substitutions or not and if the sequences reside within surface accessible, hydrophilic areas of high antigenic index and thus are targets for vaccine development, they may or may not need to be included as type IV pili-based components for inducing an immune response to NTHi.

EXAMPLE 8

To examine the role of type IV pili in NTHi-induced OM and determine if antibodies from children during natural disease recognize type IV pili, four sequential synthetic peptides were synthesized representing amino acids 21-137 of SEQ ID NO: 2 of the mature PilA of NTHi strain 86-028NP and assayed via biosensor versus a panel of pediatric sera and middle ear effusions obtained from children with OM. Serum from children at 2, 6-7, or 18-19 mos and 4-6 yrs of age with OM due to NTHi were segregated into low and high incidence groups, as determined by the number of episodes of OM.

To date, antibodies in sera obtained from children 2 and 6-7 mos of age of either high or low incidence of OM demonstrated limited reactivity with any of the type IV pili peptides, with values of 3-38 and 4-61 resonance units (RU), respectively. However, a striking difference between these groups was seen with serum obtained at 18-19 mos of age. Whereas values obtained with sera from the low incidence 18-19 mos group were 44-105 RU, sera from the high incidence panel recognized the type IV pili peptides up to five-fold greater (81-528 RU). At 4-6 yrs of age, as children naturally resolve OM, reactivity to the type IV pili peptides was again similar between the two incidence groups. To confirm that the reactivity observed here was specific for disease due to NTHi, sera from children with OM due to *S. pneumoniae* were also assayed. In all cases, RU values of 16-120 were obtained versus all type IV pili peptides. To assay for the presence of antibodies directed against type IV pili in effusions obtained from the middle ears, we also assayed these fluids via biosensor. Whereas effusions from children with OM due to *Streptococcus* were unreactive, those recovered from children with OM due to NTHi were highly reactive with type IV pili peptides. Collectively, the data strongly suggests that NTHi type IV pili are expressed in vivo, during the disease course of OM and that these structures are immunogenic.

EXAMPLE 9

Identification of immunogens that confer broad cross-protective immune responses against NTHi may be carried out as follows.

Synthesis of NTHi Pilin Pepetides

In order to map both immunodominant and adhesin-binding domains of PilA, a panel of overlapping sequential peptides as well as peptides derived from two focused areas of known diversity (see Example 6 above) are synthesized. For example, thirteen 15-mer peptides with a 5-residue overlap will be synthesized to map the entire 137 residue mature pilin protein. The final C-terminal peptide will actually be a 17-mer spanning residues 121-137 in order to incorporate the final two amino acids of mature PilA. To accommodate the two described regions of diversity, two variants of the peptide that spans residues 51-65 and two variants of the peptide that spans residues 79-95 will be synthesized. In order to fully accommodate this latter region of diversity, two peptides are made varying in length by one amino acid at the N-terminus since the region of diversity actually spans residues 79-87. Due to the additional residue, each of these latter two peptides will be 16-mers in length. Thus a total of fifteen peptides will be synthesized: twelve will be 15-mers, one will be a 17-mer and two will be 16-mer peptides. The peptides are set out in Table 2 below wherein amino acid residue numbers correspond to amino acids in SEQ ID No: 2.

TABLE 2

| Peptide | | Sequence |
| --- | --- | --- |
| OLP1 | [Residues 1-15] | FTLIELMIVIAIIAI |
| OLP2 | [Residues 11-25] | AIIAILATIAIPSYQ |
| OLP3 | [Residues 21-35] | IPSYQNYTKKAAVSE |
| OLP4 | [Residues 31-45] | AAVSELLQASAPYKA |
| OLP5 | [Residues 41-55] | APYKADVELCVYSTN |
| OLP6vA | [Residues 51-65] | VYSTNETTNCTGGKN |
| OLP6vB | [Residues 51-65] | VYSTGKPSTCSGGSN |
| OLP7 | [Residues 61-75] | TGGKNGIAADITTAK |

TABLE 2-continued

| Peptide | | Sequence |
|---|---|---|
| OLP8 | [Residues 71-85] | ITTAKGYVKSVTTSN |
| OLP9vA | [Residues 79-94] 77-95 | YVKSVTTSNGAITVKGDGT |
| OLP9vB | [Residues 79-94] 77-95 | YVASVKTQSGGITVKGNGT |
| OLP10 | [Residues 91-105] | KGDGTLANMEYILQA |
| OLP11 | [Residues 101-115] | YILQATGNAATGVTW |
| OLP12 | [Residues 111-125] | TGVTWTTTCKGTDAS |
| OLP13 | [Residues 121-137] | GTDASLFPANFCGSVTQ |

Generation of Recombinant NTHi Pilin (rPilA)

Recombinant PilA protein (rPilA) may be generated to serve as a more readily renewable product for use in assays to represent the entire pilin subunit protein. To do this, the published protocol of Keizer et al. (*J. Biol. Chem.*, 276: 24186-14193, 2001), who studied a pilin which also had four Cys residues as it will be critical that rPilA similarly be properly folded so as to possess functional qualities of the native pilin subunit, is utilized. Briefly, a truncated pilin is engineered wherein the first 28 residues are removed from the N-terminus to prevent aggregation, and this truncated pilin will be further engineered to be transported to the periplasm by means of the incorporation of an OmpA leader sequence in the construct. Using this strategy Keizer et al. generated a recombinant soluble monomeric *P. aeruginosa* pilin protein that was able to bind to its receptor (asialo GM1) in in vitro assays and decrease morbidity and mortality in mice when the peptide was delivered 15 mins. prior to heterologous challenge. This soluble, monomeric, truncated form of NTHi PilA will be useful in the studies described below.

Mapping Immunodominant Domains of PilA

The peptides and native and recombinant PilA proteins are used in concert with both acute and convalescent chinchilla and pediatric sera in addition to middle ear fluids from chinchillas and children experiencing either experimental or natural OM due to NTHi (all available within our current specimen collection or planned for collection as part of a separate initiative) to map immunodominant domains of PilA via ELISA and also biosensor assays. Briefly, PilA peptides, rPilA and native pili are bound to 96-well microtiter plates or to a biosensor chip surface, then assayed for the relative amount of antibody within serum or middle ear fluid samples that binds to each peptide.

These studies identify those regions of the pilin subunit that are relatively more immunodominant than others as recognized by both the chinchilla host and the human child. Due to the fact that the N-terminal-most synthetic peptide is comprised of highly non-polar (hydrophobic) amino acids and is thus likely buried within the pilus fiber and inaccessible to antibody, this 15-mer peptide is anticipated to serve as an internal negative control for the assays described here. Normal pediatric sera and naive chinchilla sera will serve as negative serum controls and middle ear lavage fluids recovered from a naive animal will be used as a negative control for effusions recovered during NTHi infection of the middle ear.

Mapping Adhesin Binding Domains of PilA

In order to map the eukaryotic cell binding domains of PilA, competitive ELISA assays are conducted as well as evaluations of the ability of the synthetic pilin peptides to inhibit NTHi binding to eukaryotic cells in cell culture via confocal microscopy. For initial screening assays, relevant eukaryotic target cells are grown within 96-well microtiter dishes. Cells will be washed, then pre-incubated with synthetic pilin peptides, rPilA or native NTHi pili [0.2 µg in PBS] to determine their relative ability to block binding of NTHi strain 86-028NP (grown under conditions known to promote pilin expression) to these eukaryotic cells. Relative adherence of NTHi will be determined using polyclonal antisera directed against a homologous whole NTHi OMP preparation and HRP-conjugated protein A with color developed with tetramethylbenzidine (TMB). For these assays relevant epithelial target cells [i.e. chinchilla middle ear epithelial cells (CMEEs), normal human bronchial/tracheal cells (NHuBr), human type II alveolar epithelial cell line (A549s)], a clinically irrelevant epithelial target cell to which NTHi do not adhere (CHOs) as well as an endothelial target cells [human umbilical vein endothelial cells (HUVECs)] will be used.

For those peptides that show inhibitory activity (typically the cut-off is at ≧15% inhibition of adherence relative to controls), any dose-dependence to the observed bacterial adherence blocking capability is determined. The interaction may be further evaluated by conducting adherence-blockade assays using a Transwell system wherein respiratory tract epithelial cells (CMEEs and NHuBrs) are grown at the air-fluid interface. These cells are incubated with first synthetic peptides of interest (or appropriate controls, i.e. isolated OMP P5 and P2 as positive and negative controls for NTHi surface proteins involved or not in adherence, respectively and rPilA) to attempt to block available Tfp receptors, then they will be washed 5× with fresh growth medium followed by inoculation with ~2-5×10$^7$ NTHi grown under conditions we know will promote expression of Tfp. Cultures will be washed to remove non-adherent bacteria, then fixed with methanol on ice for 5 min, air dried, rinsed with PBS and the membranes removed from the Transwell and placed on glass coverslips for imaging via confocal microscopy. To detect adherent NTHi, chinchilla hyperimmune anti-NTHi OMP serum and FITC-Protein A will be used to document the interaction of NTHi with its epithelial target cell, or conversely the blocking of this interaction by peptides that represent putative adhesin binding domains of PilA.

Choice of Immunogen

Based on the data acquired in above, immunogenic peptides are chosen based on both relative immunodominance as well as ability to inhibit adherence of NTHi to respiratory epithelial target cells. Depending on the biochemical and structural characteristics of the regions of interest, the peptides will be produced as either synthetic peptide(s) or recombinant peptide(s).

Immunogenicity and protective efficacy of the PilA immunogens is evaluated initially in the chinchilla animal model disclosed herein and in human trials.

EXAMPLE SUMMARY

The foregoing evidence indicates that NTHi express functional type IV pili on their surface. The proteins encoded by these genes are known to be important for transformation competence in typeable *H. influenzae* and are contemplated herein to be important for biofilm formation by NTHi as well. Collectively, these observations indicate that NTHi is likely to up-regulate expression of type IV pili in the nutrient restricted environment of the human host. Thus, type IV pili represent an excellent target for a vaccine and/or for an antimicrobial strategy for pathogenic conditions caused by NTHi as well as *H. influenzae* strains a, b, c, e and f.

We claim:

1. An isolated polypeptide comprising an amino acid sequence encoded by a nucleotide sequence selected from the group consisting of pilA SEQ ID NO: 1, pilB SEQ ID NO: 3, pilC SEQ ID NO: 5, pilD SEQ ID NO: 7, comA SEQ ID NO: 9, comB SEQ ID NO: 11, comC SEQ ID NO: 13, comD SEQ ID NO: 15, comE SEQ ID NO: 17, comF SEQ ID NO: 19, pilF SEQ ID NO: 21, pilA SEQ ID NO: 33, pilA SEQ ID NO: 35, pilA SEQ ID NO: 37, pilA SEQ ID NO: 39, pilA SEQ ID NO: 41and pilA SEQ ID NO: 43.

2. An isolated polypeptide comprising an amino acid sequence selected from the group consisting of polypeptide SEQ ID NO: 2, PilB polypeptide SEQ ID NO: 4, PilC polypeptide SEQ ID NO: 6, PilD polypeptide SEQ ID NO: 8, ComA polypeptide SEQ ID NO: 10, ComB polypeptide SEQ ID NO: 12, ComC polypeptide SEQ ID NO: 14, ComD polypeptide SEQ ID NO: 16, ComE polypeptide SEQ ID NO: 18, ComF polypeptide SEQ ID NO: 20, PilF polypeptide SEQ ID NO: 22, PilA polypeptide SEQ ID NO: 34, PilA polypeptide SEQ ID NO: 36, PilA polypeptide SEQ ID NO: 38, PilA polypeptide SEQ ID NO: 40, PilA polypeptide SEQ ID NO: 42, and pilA polypeptide SEQ ID NO: 44.

3. A composition comprising a polypeptide of claim 2 and a pharmaceutically acceptable carrier.

4. A method of treating NTHi bacterial infection comprising administering a molecule that inhibits expression or activity of a polypeptide of claim 2 to an patient in need thereof.

5. The method of claim 4 wherein the molecule administered to the patient in need is an antisense oligonucleotide.

6. The method of claim 4 wherein the molecule administered to the patient in need is an antibody.

7. The method of claim 4 wherein the molecule administered to the patient in need is a small molecule.

8. The method of claim 4 wherein the NTHi infection is in the middle ear.

9. An isolated peptide fragment consisting of a fragment of an amino acid sequence selected from the group consisting of PilA polypeptide SEQ ID NO: 2, PilB polypeptide SEQ ID NO: 4, PilC polypeptide SEQ ID NO: 6, PilD polypeptide SEQ ID NO: 8, ComA polypeptide SEQ ID NO: 10, ComB polypeptide SEQ ID NO: 12, ComC polypeptide SEQ ID NO: 14, ComD polypeptide SEQ ID NO: 16, ComE polypeptide SEQ ID NO: 18, ComF polypeptide SEQ ID NO: 20, PilF polypeptide SEQ ID NO: 22, PilA polypeptide SEQ ID NO: 34, PilA polypeptide SEQ ID NO: 36, PilA polypeptide SEQ ID NO: 38, PilA polypeptide SEQ ID NO: 40, PilA polypeptide SEQ ID NO: 42, and pilA polypeptide SEQ ID NO: 44, wherein the peptide fragment elicits an immune response to H. influenzae pilin polypeptide.

10. An isolated peptide fragment consisting of a fragment of an amino acid sequence selected from the group consisting of PilA polypeptide SEQ ID NO: 2, PilB polypeptide SEQ ID NO: 4, PilC polypeptide SEQ ID NO: 6, PilD polypeptide SEQ ID NO: 8, ComA polypeptide SEQ ID NO: 10, ComB polypeptide SEQ ID NO: 12, ComC polypeptide SEQ ID NO: 14, ComD polypeptide SEQ ID NO: 16, ComE polypeptide SEQ ID NO: 18, ComF polypeptide SEQ ID NO: 20, PilF polypeptide SEQ ID NO: 22, PilA polypeptide SEQ ID NO: 34, PilA polypeptide SEQ ID NO: 36, PilA polypeptide SEQ ID NO: 38, PilA polypeptide SEQ ID NO: 40, PilA polypeptide SEQ ID NO: 42, and pilA polypeptide SEQ ID NO: 44, wherein the peptide fragment inhibits H. influenzae cellular adherence.

11. An isolated peptide fragment of the polypeptide of claim 2, wherein the peptide fragment comprises amino acids 35 through 68 of SEQ ID NO:2.

12. An isolated peptide fragment of the polypeptide of claim 2, wherein the peptide fragment comprises amino acids 69 through 102 of SEQ ID NO: 2.

13. An isolated peptide fragment of the polypeptide of claim 2, wherein the peptide fragment comprises amino acids 102 through 137 of SEQ ID NO: 2.

14. An isolated peptide fragment of the polypeptide of claim 2, wherein the peptide fragment comprises amino acids 21 through 35 of SEQ ID NO: 2.

15. A method for eliciting an immune response to NTHi bacteria comprising administering an immunogenic dose of one or more polypeptides of claim 2 or peptide fragments of claim 11-14 to a patient at risk of NTHi bacterial infection.

16. A composition comprising (a) said peptide fragment of claim 9, 10, 11, 12, 13, or 14 and (b) a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,501,131 B2 | Page 1 of 1 |
| APPLICATION NO. | : 11/019005 | |
| DATED | : March 10, 2009 | |
| INVENTOR(S) | : Lauren O. Bakaletz et al. | |

It is certified that error appears in the above-identified patent and that said Letters Patent is hereby corrected as shown below:

Title Page:

Item (74), "Marshall" should be -- Marshall, --.

In the Claims:

At Column 117, line 12, "of polypeptide" should be -- of PilA polypeptide --.

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,501,131 B2 | Page 1 of 1 |
| APPLICATION NO. | : 11/019005 | |
| DATED | : March 10, 2009 | |
| INVENTOR(S) | : Lauren O. Bakaletz et al. | |

It is certified that error appears in the above-identified patent and that said Letters Patent is hereby corrected as shown below:

In the Specification:

At column 1, lines 6-9 –

"Experimental work related to the invention described herein was supported by grants R01 DC3915 and R01 DC005980 from NIH/NIDCD. The United States government may have certain rights in the invention." should be --

"Part of the work during the development of this invention was made with government support from the National Institutes of Health under grant numbers R01DC03915 and R01DC005980. The U.S. Government has certain rights in the invention."

Signed and Sealed this
Sixteenth Day of October, 2012

David J. Kappos
*Director of the United States Patent and Trademark Office*

SEQUENCE LISTING

<160> NUMBER OF SEQ ID NOS: 44

<210> SEQ ID NO 1
<211> LENGTH: 4345
<212> TYPE: DNA
<213> ORGANISM: H. influenzae
<220> FEATURE:
<221> NAME/KEY: CDS
<222> LOCATION: (403)..(852)

<400> SEQUENCE: 1

```
gcgatcatta aaattgacat attgcgtaat tcgcccattt cgttcgatca acaatgtgc      60 tgaaacacgc atttgataaa tttctgcaaa ataaggatga atcttaggat ctaattttcc   120
ttgaaaaaaa tcatccacat atccgccgcc aaattgttct ggcggcagac taatataatg   180
aataaccaat aaggaaatat cctgtggatt tgggcgttta tcgaagtgag gtgactgaat   240
ttgccgacaa tccaatatac cttgttcaat atctttagt ttttgcatac tttttcctt    300 tttttgcgat caggatcgca gaaaaagtgc ggtcaatttt acaaacaaat ttttcctttt   360
cacaatgtcg tcgctaacaa aggcttaata aaaggaaaat ga atg aaa cta aca      414
                                              Met Lys Leu Thr
                                                1 aca cag caa acc ttg aaa aaa ggg ttt aca tta ata gag cta atg att    462
Thr Gln Gln Thr Leu Lys Lys Gly Phe Thr Leu Ile Glu Leu Met Ile
  5                  10                  15                  20 gtg att gca att att gct att tta gcc act atc gca att ccc tct tat    510
Val Ile Ala Ile Ile Ala Ile Leu Ala Thr Ile Ala Ile Pro Ser Tyr
                 25                  30                  35 caa aat tat act aaa aaa gca gcg gta tct gaa tta ctg caa gcg tca    558
Gln Asn Tyr Thr Lys Lys Ala Ala Val Ser Glu Leu Leu Gln Ala Ser
             40                  45                  50 gcg cct tat aag gct gat gtg gaa tta tgt gta tat agc aca aat gaa    606
Ala Pro Tyr Lys Ala Asp Val Glu Leu Cys Val Tyr Ser Thr Asn Glu
         55                  60                  65 aca aca aac tgt acg ggt gga aaa aat ggt att gca gca gat ata acc    654
Thr Thr Asn Cys Thr Gly Gly Lys Asn Gly Ile Ala Ala Asp Ile Thr
     70                  75                  80 aca gca aaa ggc tat gta aaa tca gtg aca aca agc aac ggt gca ata    702
Thr Ala Lys Gly Tyr Val Lys Ser Val Thr Thr Ser Asn Gly Ala Ile
 85                  90                  95                 100 aca gta aaa ggg gat ggc aca ttg gca aat atg gaa tat att ttg caa    750
Thr Val Lys Gly Asp Gly Thr Leu Ala Asn Met Glu Tyr Ile Leu Gln
                105                 110                 115 gct aca ggt aat gct gca aca ggt gta act tgg aca aca act tgc aaa    798
Ala Thr Gly Asn Ala Ala Thr Gly Val Thr Trp Thr Thr Thr Cys Lys
            120                 125                 130 gga acg gat gcc tct tta ttt cca gca aat ttt tgc gga agt gtc aca    846
Gly Thr Asp Ala Ser Leu Phe Pro Ala Asn Phe Cys Gly Ser Val Thr
        135                 140                 145 caa tga cgagctatgc tttacttcat actcagcgtg taaccgctca aaatggcgag      902
Gln atctttacga tctcgccaga tttatgggaa cgcaatcagc agcaacaatc cttgctcttg   962
cggtattttg ctttgccact taagaagaa ataatcgtc tttggctagg ggttgattct    1022
ctctccaatc tttcagcttg tgaaaccatt gcgtttataa caggaaaacc tgtcgaacca   1082
attttgttag aaagcagcca actcaaagaa ctgttacaac aacttactcc gcaccaaatg   1142
caagtggaag agcaagttaa attctatcaa catcaagaaa cccatttga acaagaagat    1202
```

```
gatgaacctg ttatccgctt acttaatcag attttttgaat ctgccttaca aaaaaatgcc   1262
tctgatattc atttagaaac cttggctgat cagtttcaag tgcggtttag aattgatggt   1322
gttttacaac cacaacccct aataagcaaa atattcgcca atcgtattat ttcacgctta   1382
aaattactgg ctaaattaga tattagtgaa atcgacttc cacaagatgg acgatttcaa    1442
tttaaaacca cttttttccga tattcttgat tttcgccttt caaccttacc aacccattgg  1502
ggcgaaaaaa tcgtgttgcg agcgcaacaa aataaacctg tagaacttag ctttgctgaa   1562
ctgggtatga ccgaaaatca gcaacaagca tttcaacgct cacttagcca gccacaagga   1622
ttaattttag taaccggccc cacaggaagt gggaaaagta tctcgcttta caccgcactt   1682
cagtggctaa atacgcctga taaacatatt atgaccgctg aagatcccat tgaaattgaa   1742
cttgatggta ttattcaaag ccaaattaat ccgcagattg gattagattt tagccgtcta   1802
ttgcgtgctt ttttacgtca agatcccgac atcattatgc taggtgaaat tcgagatgaa   1862
gaaagtgcaa ggattgcact acgtgccgct caaacgggac atttggtgct ttcaaccttta  1922 cataccaatg atgcaatatc tgccatttct cgcttacaac aactcggtat tcaacaacat   1982
gaaattgaaa acagtttact actcgtcatt gcacagcgtc ttgtacgaaa aatctgtcca   2042
aagtgcggtg gaaatttaat aaaattcttgt gattgccatc aaggttatcg agggcgaatc   2102
ggcgtgtatc aatttctaca ttggcaacag aatggctatc aaacggattt tgagaattta   2162
cgagagagtg gtttggaaaa agttagccaa ggcataacag atgagaaaga aattgaacgt   2222
gtgttaggta aaaactcatg actaaaaaac tcttttatta tcaaggtagt aacgcattaa   2282
atcagaaaca aaaaggctca attattgcgg atacgaaaca acaagcgcac tttcagttaa   2342
taagccgcgg gcttactcac atcaaattac aacaaaactg gcaatttggg gcaaaaccca   2402
aaaattcaga aatcagtgaa ttactcaatc aattagcgac attgctacag tccgtaattc   2462
cgttaaaaaa cagcctacaa attttgcaac aaaattgtac tcaaattatg ctcaacaaat   2522
ggcttgaacg actgcttcaa tccattgaat ctggcttagc attctcacaa gccattgaac   2582
aacaaggaaa atatctcaca caacaagaaa ttcaactgat tcaagtggga gaaatgacag   2642
gaaaacttgc cgtagtttgt aaaaaaatag ccacgcaccg tagtcaatct ttggctttac   2702
aacgcaaatt acagaaaatt atgttatatc cctcaatggt attgggaatt tctctattat   2762
tgacactcgc attactgctt tttatcgcgc ctcaatttgc tgaaatgtac agtggcaata   2822
atgcggagtc accaacaata accgcaatat tgctctcaat atctaatttc cttaagcaaa   2882
atattggcat tttgctattt ttcgttttga gttttttttct attttattat ttctatctaa   2942
aacgccagac ttggtttcat caaaagaaaa atcaacttat ttctatcacg cctattttg    3002 gcacaattca aaagctttca cgtttagtga actttagtca aagtttacaa attatgttgc   3062
aggccggcgt accgcttaat caggcactag acagttttct tcctcgcaca caaacttggc   3122
aaaccaagaa aacgcttgta aacgatatgg tattagataa agaagtgcgg tcaattttgc   3182
aatgggtttc tcaaggctat gcgttttcta atagcgtaag tagcgatctt ttcccgatgg   3242
aagcacaaca aatgctacaa attggcgaac aaagcggaaa actcgctttg atgctagagc   3302
atatcgcaga taattaccaa gaaaaactta atcatcaaat tgacttactc tcacaaatgc   3362
tagaaccatt aatgatggta atcatcggca gtctgattgg gattattatg atgggaatgt   3422 atttaccctat ctttaatatg ggatcagtta ttcaatgatt tacttcacaa tgttttttatt  3482 aggcggcatc ttagggatcg cattgtggtt ctacctatct ggttttatta cgcatttgca   3542
```

```
gcaagagatt tatgcgactt acgttgaatt atttccacaa aacagttctc catttcaacc    3602
gcactttgcc tctattcaac aaaaaaagtg cggtcatatt ttgaggtatt tttttagtat    3662
tggggttgga tttatatttt tacaaattgc cttcaaagat tctattttta ctgtatggat    3722
cggactcaca cttattattc tttggacaat cagttatctt gattggcact atcaacttat    3782
ttctacgaca ccctgtttat ggttacttac tctcggttta tttggcgcag acaataactt    3842
ttcattgcta acgttatctg aaagcataaa aagtgcggct agttttttta ttgttttcta    3902
cgcaatctat tggattgcaa atgttatta tagaaaagaa gcctttggac ggggagatta    3962
ttggctagca atggcattag gaagttttat tcatttagaa accttaccgc acttttatt    4022 attagcctca gtgcttggaa tatgttttc gcttattcat aaaaagaaaa agaatttat    4082 accttttgcc cctttatga acttatcggc tatcattatt tatctcgtca aatattacgg    4142
atattaaaaa ggggaaaaca taatattttt cccttgttct tcatagaagt gcggttgttt    4202
ttacgaacgt ttcatcactt caaaaaactc ttcgttggtt ttcgccatca tcagcttatc    4262
aatcaagaat tccattgcat ccacttcatc cattggatta agaatcttac gaagaatcca    4322
cattttttgt aattcgtccg ctg                                           4345
```

<210> SEQ ID NO 2
<211> LENGTH: 149
<212> TYPE: PRT
<213> ORGANISM: H. influenzae

<400> SEQUENCE: 2

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

<210> SEQ ID NO 3
<211> LENGTH: 4345
<212> TYPE: DNA
<213> ORGANISM: H. influenzae
<220> FEATURE:
<221> NAME/KEY: CDS
<222> LOCATION: (849)..(2243)

<400> SEQUENCE: 3

```
gcgatcatta aaattgacat attgcgtaat tcgcccattt cgttcgatca aacaatgtgc      60
```

```
tgaaacacgc atttgataaa tttctgcaaa ataaggatga atcttaggat ctaattttcc      120
ttgaaaaaaa tcatccacat atccgccgcc aaattgttct ggcggcagac taatataatg      180
aataaccaat aaggaaatat cctgtggatt tgggcgttta tcgaagtgag gtgactgaat      240
ttgccgacaa tccaatatac cttgttcaat atctttttagt ttttgcatac ttttttcctt    300 ttttgcgat caggatcgca gaaaaagtgc ggtcaattt acaaacaaat ttttcctttt       360
cacaatgtcg tcgctaacaa aggcttaata aaaggaaaat gaatgaaact aacaacacag      420
caaaccttga aaaagggtt tacattaata gagctaatga ttgtgattgc aattattgct      480
attttagcca ctatcgcaat tccctcttat caaaattata ctaaaaaagc agcggtatct     540
gaattactgc aagcgtcagc gccttataag gctgatgtgg aattatgtgt atatagcaca     600
aatgaaacaa caaactgtac gggtggaaaa atggtatttg cagcagatat aaccacagca    660
aaaggctatg taaaatcagt gacaacaagc aacggtgcaa taacagtaaa aggggatggc    720
acattggcaa atatggaata tattttgcaa gctacaggta atgctgcaac aggtgtaact   780
tggacaacaa cttgcaaagg aacggatgcc tctttattttc cagcaaattt tgcggaagt   840 gtcacaca atg acg agc tat gct tta ctt cat act cag cgt gta acc gct     890
         Met Thr Ser Tyr Ala Leu Leu His Thr Gln Arg Val Thr Ala
          1               5                    10 caa aat ggc gag atc ttt acg atc tcg cca gat tta tgg gaa cgc aat      938
Gln Asn Gly Glu Ile Phe Thr Ile Ser Pro Asp Leu Trp Glu Arg Asn
 15              20                    25                    30 cag cag caa caa tcc ttg ctc ttg cgg tat ttt gct ttg cca ctt aaa      986
Gln Gln Gln Gln Ser Leu Leu Leu Arg Tyr Phe Ala Leu Pro Leu Lys
                 35                    40                    45 gaa gaa aat aat cgt ctt tgg cta ggg gtt gat tct ctc tcc aat ctt     1034
Glu Glu Asn Asn Arg Leu Trp Leu Gly Val Asp Ser Leu Ser Asn Leu
             50                    55                    60 tca gct tgt gaa acc att gcg ttt ata aca gga aaa cct gtc gaa cca     1082
Ser Ala Cys Glu Thr Ile Ala Phe Ile Thr Gly Lys Pro Val Glu Pro
         65                    70                    75 att ttg tta gaa agc agc caa ctc aaa gaa ctg tta caa caa ctt act     1130
Ile Leu Leu Glu Ser Ser Gln Leu Lys Glu Leu Leu Gln Gln Leu Thr
     80                    85                    90 ccg cac caa atg caa gtg gaa gag caa gtt aaa ttc tat caa cat caa     1178
Pro His Gln Met Gln Val Glu Glu Gln Val Lys Phe Tyr Gln His Gln
 95                   100                   105                  110 gaa acc cat ttt gaa caa gaa gat gat gaa cct gtt atc cgc tta ctt     1226
Glu Thr His Phe Glu Gln Glu Asp Asp Glu Pro Val Ile Arg Leu Leu
                115                   120                   125 aat cag att ttt gaa tct gcc tta caa aaa aat gcc tct gat att cat     1274
Asn Gln Ile Phe Glu Ser Ala Leu Gln Lys Asn Ala Ser Asp Ile His
            130                   135                   140 tta gaa acc ttg gct gat cag ttt caa gtg cgg ttt aga att gat ggt     1322
Leu Glu Thr Leu Ala Asp Gln Phe Gln Val Arg Phe Arg Ile Asp Gly
        145                   150                   155 gtt tta caa cca caa ccc tta ata agc aaa ata ttc gcc aat cgt att     1370
Val Leu Gln Pro Gln Pro Leu Ile Ser Lys Ile Phe Ala Asn Arg Ile
    160                   165                   170 att tca cgc tta aaa tta ctg gct aaa tta gat att agt gaa aat cga     1418
Ile Ser Arg Leu Lys Leu Leu Ala Lys Leu Asp Ile Ser Glu Asn Arg
175                   180                   185                   190 ctt cca caa gat gga cga ttt caa ttt aaa acc act ttt tcc gat att     1466
Leu Pro Gln Asp Gly Arg Phe Gln Phe Lys Thr Thr Phe Ser Asp Ile
                195                   200                   205 ctt gat ttt cgc ctt tca acc tta cca acc cat tgg ggc gaa aaa atc     1514
```

-continued

```
                Leu Asp Phe Arg Leu Ser Thr Leu Pro Thr His Trp Gly Glu Lys Ile
                            210                 215                 220 gtg ttg cga gcg caa caa aat aaa cct gta gaa ctt agc ttt gct gaa        1562
Val Leu Arg Ala Gln Gln Asn Lys Pro Val Glu Leu Ser Phe Ala Glu
            225                 230                 235 ctg ggt atg acc gaa aat cag caa caa gca ttt caa cgc tca ctt agc        1610
Leu Gly Met Thr Glu Asn Gln Gln Gln Ala Phe Gln Arg Ser Leu Ser
        240                 245                 250 cag cca caa gga tta att tta gta acc ggc ccc aca gga agt ggg aaa        1658
Gln Pro Gln Gly Leu Ile Leu Val Thr Gly Pro Thr Gly Ser Gly Lys
255                 260                 265                 270 agt atc tcg ctt tac acc gca ctt cag tgg cta aat acg cct gat aaa        1706
Ser Ile Ser Leu Tyr Thr Ala Leu Gln Trp Leu Asn Thr Pro Asp Lys
                275                 280                 285 cat att atg acc gct gaa gat ccc att gaa att gaa ctt gat ggt att        1754
His Ile Met Thr Ala Glu Asp Pro Ile Glu Ile Glu Leu Asp Gly Ile
            290                 295                 300 att caa agc caa att aat ccg cag att gga tta gat ttt agc cgt cta        1802
Ile Gln Ser Gln Ile Asn Pro Gln Ile Gly Leu Asp Phe Ser Arg Leu
        305                 310                 315 ttg cgt gct ttt tta cgt caa gat ccc gac atc att atg cta ggt gaa        1850
Leu Arg Ala Phe Leu Arg Gln Asp Pro Asp Ile Ile Met Leu Gly Glu
320                 325                 330 att cga gat gaa gaa agt gca agg att gca cta cgt gcc gct caa acg        1898
Ile Arg Asp Glu Glu Ser Ala Arg Ile Ala Leu Arg Ala Ala Gln Thr
335                 340                 345                 350 gga cat ttg gtg ctt tca act tta cat acc aat gat gca ata tct gcc        1946
Gly His Leu Val Leu Ser Thr Leu His Thr Asn Asp Ala Ile Ser Ala
                355                 360                 365 att tct cgc tta caa caa ctc ggt att caa caa cat gaa att gaa aac        1994
Ile Ser Arg Leu Gln Gln Leu Gly Ile Gln Gln His Glu Ile Glu Asn
            370                 375                 380 agt tta cta ctc gtc att gca cag cgt ctt gta cga aaa atc tgt cca        2042
Ser Leu Leu Leu Val Ile Ala Gln Arg Leu Val Arg Lys Ile Cys Pro
        385                 390                 395 aag tgc ggt gga aat tta ata aat tct tgt gat tgc cat caa ggt tat        2090
Lys Cys Gly Gly Asn Leu Ile Asn Ser Cys Asp Cys His Gln Gly Tyr
400                 405                 410 cga ggg cga atc ggc gtg tat caa ttt cta cat tgg caa cag aat ggc        2138
Arg Gly Arg Ile Gly Val Tyr Gln Phe Leu His Trp Gln Gln Asn Gly
415                 420                 425                 430 tat caa acg gat ttt gag aat tta cga gag agt ggt ttg gaa aaa gtt        2186
Tyr Gln Thr Asp Phe Glu Asn Leu Arg Glu Ser Gly Leu Glu Lys Val
                435                 440                 445 agc caa ggc ata aca gat gag aaa gaa att gaa cgt gtg tta ggt aaa        2234
Ser Gln Gly Ile Thr Asp Glu Lys Glu Ile Glu Arg Val Leu Gly Lys
            450                 455                 460 aac tca tga ctaaaaaact cttttattat caaggtagta acgcattaaa               2283
Asn Ser tcagaaacaa aaaggctcaa ttattgcgga tacgaaacaa caagcgcact ttcagttaat      2343
aagccgcggg cttactcaca tcaaattaca acaaaactgg caatttgggg caaaaccccaa    2403 aaattcagaa atcagtgaat tactcaatca attagcgaca ttgctacagt ccgtaattcc     2463
gttaaaaaac agcctacaaa ttttgcaaca aaattgtact caaattatgc tcaacaaatg     2523
gcttgaacga ctgcttcaat ccattgaatc tggcttagca ttctcacaag ccattgaaca     2583
acaaggaaaa tatctcacac aacaagaaat tcaactgatt caagtgggag aaatgacagg     2643
aaaacttgcc gtagtttgta aaaaaatagc cacgcaccgt agtcaatctt tggctttaca     2703
```

```
acgcaaatta cagaaaatta tgttatatcc ctcaatggta ttgggaattt ctctattatt   2763
gacactcgca ttactgcttt ttatcgcgcc tcaatttgct gaaatgtaca gtggcaataa   2823
tgcggagtta ccaacaataa ccgcaatatt gctctcaata tctaatttcc ttaagcaaaa   2883
tattggcatt ttgctatttt tcgttttgag ttttttttcta ttttattatt tctatctaaa   2943
acgccagact tggtttcatc aaaagaaaaa tcaacttatt tctatcacgc ctattttgg    3003 cacaattcaa aagctttcac gtttagtgaa ctttagtcaa agtttacaaa ttatgttgca   3063
ggccggcgta ccgcttaatc aggcactaga cagttttctt cctcgcacac aaacttggca   3123
aaccaagaaa acgcttgtaa acgatatggt attagataaa gaagtgcggt caattttgca   3183
atgggtttct caaggctatg cgttttctaa tagcgtaagt agcgatcttt cccgatgga    3243 agcacaacaa atgctacaaa ttggcgaaca aagcggaaaa ctcgctttga tgctagagca   3303
tatcgcagat aattaccaag aaaaacttaa tcatcaaatt gacttactct cacaaatgct   3363
agaaccatta atgatggtaa tcatcggcag tctgattggg attattatga tgggaatgta   3423
tttacctatc tttaatatgg gatcagttat tcaatgattt acttcacaat gttttttatta  3483 ggcggcatct tagggatcgc attgtggttc tacctatctg gttttattac gcatttgcag   3543
caagagattt atgcgactta cgttgaatta tttccacaaa acagttctcc atttcaaccg   3603
cactttgcct ctattcaaca aaaaaagtgc ggtcatattt tgaggtattt ttttagtatt   3663
ggggttggat ttatattttt acaaattgcc ttcaaagatt ctattttac tgtatggatc    3723 ggactcacac ttattattct ttggacaatc agttatcttg attggcacta tcaacttatt   3783
tctacgacac cctgtttatg gttacttact ctcggtttat ttggcgcaga caataacttt   3843
tcattgctaa cgttatctga aagcataaaa agtgcggcta gttttttat tgttttctac   3903 gcaatctatt ggattgcaaa atgttattat agaaagaag cctttggacg gggagattat    3963
tggctagcaa tggcattagg aagttttatt catttagaaa ccttaccgca ctttttatta   4023
ttagcctcag tgcttggaat atgttttcg cttattcata aaagaaaaa agaatttata     4083 cctttttgccc ctttttatgaa cttatcggct atcattattt atctcgtcaa atattacgga  4143
tattaaaaag gggaaaacat aatatttttc ccttgttctt catagaagtg cggttgtttt   4203
tacgaacgtt tcatcacttc aaaaaactct cgttggttt tcgccatcat cagcttatca    4263
atcaagaatt ccattgcatc cacttcatcc attggattaa gaatcttacg aagaatccac   4323 atttttttgta attcgtccgc tg                                           4345
```

<210> SEQ ID NO 4
<211> LENGTH: 464
<212> TYPE: PRT
<213> ORGANISM: H. influenzae

<400> SEQUENCE: 4

```
Met Thr Ser Tyr Ala Leu Leu His Thr Gln Arg Val Thr Ala Gln Asn
1               5                   10                  15

Gly Glu Ile Phe Thr Ile Ser Pro Asp Leu Trp Glu Arg Asn Gln Gln
            20                  25                  30

Gln Gln Ser Leu Leu Leu Arg Tyr Phe Ala Leu Pro Leu Lys Glu Glu
        35                  40                  45

Asn Asn Arg Leu Trp Leu Gly Val Asp Ser Leu Ser Asn Leu Ser Ala
    50                  55                  60

Cys Glu Thr Ile Ala Phe Ile Thr Gly Lys Pro Val Glu Pro Ile Leu
65                  70                  75                  80
```

```
Leu Glu Ser Ser Gln Leu Lys Glu Leu Leu Gln Gln Leu Thr Pro His
                 85                  90                  95
Gln Met Gln Val Glu Glu Gln Val Lys Phe Tyr Gln His Gln Glu Thr
            100                 105                 110
His Phe Glu Gln Glu Asp Asp Glu Pro Val Ile Arg Leu Leu Asn Gln
        115                 120                 125
Ile Phe Glu Ser Ala Leu Gln Lys Asn Ala Ser Asp Ile His Leu Glu
    130                 135                 140
Thr Leu Ala Asp Gln Phe Gln Val Arg Phe Arg Ile Asp Gly Val Leu
145                 150                 155                 160
Gln Pro Gln Pro Leu Ile Ser Lys Ile Phe Ala Asn Arg Ile Ile Ser
                165                 170                 175
Arg Leu Lys Leu Leu Ala Lys Leu Asp Ile Ser Glu Asn Arg Leu Pro
            180                 185                 190
Gln Asp Gly Arg Phe Gln Phe Lys Thr Thr Phe Ser Asp Ile Leu Asp
        195                 200                 205
Phe Arg Leu Ser Thr Leu Pro Thr His Trp Gly Glu Lys Ile Val Leu
    210                 215                 220
Arg Ala Gln Gln Asn Lys Pro Val Glu Leu Ser Phe Ala Glu Leu Gly
225                 230                 235                 240
Met Thr Glu Asn Gln Gln Ala Phe Gln Arg Ser Leu Ser Gln Pro
                245                 250                 255
Gln Gly Leu Ile Leu Val Thr Gly Pro Thr Gly Ser Gly Lys Ser Ile
            260                 265                 270
Ser Leu Tyr Thr Ala Leu Gln Trp Leu Asn Thr Pro Asp Lys His Ile
        275                 280                 285
Met Thr Ala Glu Asp Pro Ile Glu Ile Glu Leu Asp Gly Ile Ile Gln
    290                 295                 300
Ser Gln Ile Asn Pro Gln Ile Gly Leu Asp Phe Ser Arg Leu Leu Arg
305                 310                 315                 320
Ala Phe Leu Arg Gln Asp Pro Asp Ile Ile Met Leu Gly Glu Ile Arg
                325                 330                 335
Asp Glu Glu Ser Ala Arg Ile Ala Leu Arg Ala Ala Gln Thr Gly His
            340                 345                 350
Leu Val Leu Ser Thr Leu His Thr Asn Asp Ala Ile Ser Ala Ile Ser
        355                 360                 365
Arg Leu Gln Gln Leu Gly Ile Gln Gln His Glu Ile Glu Asn Ser Leu
    370                 375                 380
Leu Leu Val Ile Ala Gln Arg Leu Val Arg Lys Ile Cys Pro Lys Cys
385                 390                 395                 400
Gly Gly Asn Leu Ile Asn Ser Cys Asp Cys His Gln Gly Tyr Arg Gly
                405                 410                 415
Arg Ile Gly Val Tyr Gln Phe Leu His Trp Gln Gln Asn Gly Tyr Gln
            420                 425                 430
Thr Asp Phe Glu Asn Leu Arg Glu Ser Gly Leu Glu Lys Val Ser Gln
        435                 440                 445
Gly Ile Thr Asp Glu Lys Glu Ile Glu Arg Val Leu Gly Lys Asn Ser
    450                 455                 460

<210> SEQ ID NO 5
<211> LENGTH: 4345
<212> TYPE: DNA
<213> ORGANISM: H. influenzae
<220> FEATURE:
```

```
<221> NAME/KEY: CDS
<222> LOCATION: (2240)..(3460)

<400> SEQUENCE: 5
gcgatcatta aaattgacat attgcgtaat tcgcccattt cgttcgatca aacaatgtgc      60
tgaaacacgc atttgataaa tttctgcaaa ataaggatga atcttaggat ctaattttcc    120
ttgaaaaaaa tcatccacat atccgccgcc aaattgttct ggcggcagac taatataatg    180
aataaccaat aaggaaatat cctgtggatt tgggcgttta tcgaagtgag gtgactgaat    240
ttgccgacaa tccaatatac cttgttcaat atcttttagt ttttgcatac tttttttcctt   300
tttttgcgat caggatcgca gaaaaagtgc ggtcaatttt acaaacaaat ttttccttttt   360
cacaatgtcg tcgctaacaa aggcttaata aaaggaaaat gaatgaaact aacaacacag    420
caaaccttga aaaagggtt  tacattaata gagctaatga ttgtgattgc aattattgct    480
atttttagcca ctatcgcaat tccctcttat caaaattata ctaaaaaagc agcggtatct   540
gaattactgc aagcgtcagc gccttataag gctgatgtgg aattatgtgt atatagcaca    600
aatgaaacaa caactgtac  gggtggaaaa atggtattg  cagcagatat aaccacagca    660
aaaggctatg taaaatcagt gacaacaagc aacggtgcaa taacagtaaa aggggatggc    720
acattggcaa atatggaata tattttgcaa gctacaggta atgctgcaac aggtgtaact    780
tggacaacaa cttgcaaagg aacggatgcc tctttatttc cagcaaattt ttgcggaagt    840
gtcacacaat gacgagctat gctttacttc atactcagcg tgtaaccgct caaaatggcg    900
agatctttac gatctcgcca gatttatggg aacgcaatca gcagcaacaa tccttgctct    960
tgcggtattt tgctttgcca cttaagaag  aaaataatcg tctttggcta ggggttgatt   1020
ctctctccaa tctttcagct tgtgaaacca ttgcgtttat aacaggaaaa cctgtcgaac   1080
caattttgtt agaaagcagc caactcaaag aactgttaca acaacttact ccgcaccaaa   1140
tgcaagtgga agagcaagtt aaattctatc aacatcaaga aacccatttt gaacaagaag   1200
atgatgaacc tgttatccgc ttacttaatc agatttttga atctgcctta caaaaaaatg   1260
cctctgatat tcatttagaa accttggctg atcagtttca agtgcggttt agaattgatg   1320
gtgttttaca accacaaccc ttaataagca aaatattcgc caatcgtatt atttcacgct   1380
taaaattact ggctaaatta gatattagtg aaaatcgact tccacaagat ggacgatttc   1440
aatttaaaac cacttttttcc gatattcttg attttcgcct ttcaaccttta ccaacccatt   1500
ggggcgaaaa atcgtgttg cgagcgcaac aaaataaacc tgtagaactt agctttgctg    1560
aactgggtat gaccgaaaat cagcaacaag catttcaacg ctcacttagc cagccacaag   1620
gattaattt  agtaaccggc cccacaggaa gtgggaaaag tatctcgctt tacaccgcac   1680
ttcagtggct aaatacgcct gataaacata ttatgaccgc tgaagatccc attgaaattg   1740
aacttgatgg tattattcaa agccaaatta atccgcagat tggattagat tttagccgtc   1800
tattgcgtgc tttttttacgt caagatcccg acatcattat gctaggtgaa attcgagatg   1860
aagaaagtgc aaggattgca ctacgtgccg ctcaaacggg acatttggtg ctttcaactt   1920
tacataccaa tgatgcaata tctgccattt ctcgcttaca acaactcggt attcaacaac   1980
atgaaattga aaacagttta ctactcgtca ttgcacagcg tcttgtacga aaaatctgtc   2040
caaagtgcgg tggaaattta ataaattctt gtgattgcca tcaaggttat cgagggcgaa   2100
tcggcgtgta tcaatttcta cattggcaac agaatggcta tcaaacggat tttgagaatt   2160
tacgagagag tggtttggaa aaagttagcc aaggcataac agatgagaaa gaaattgaac   2220
```

-continued

```
gtgtgttagg taaaaactc atg act aaa aaa ctc ttt tat tat caa ggt agt        2272
              Met Thr Lys Lys Leu Phe Tyr Tyr Gln Gly Ser
              1               5                   10 aac gca tta aat cag aaa caa aaa ggc tca att att gcg gat acg aaa         2320
Asn Ala Leu Asn Gln Lys Gln Lys Gly Ser Ile Ile Ala Asp Thr Lys
            15                  20                  25 caa caa gcg cac ttt cag tta ata agc cgc ggg ctt act cac atc aaa         2368
Gln Gln Ala His Phe Gln Leu Ile Ser Arg Gly Leu Thr His Ile Lys
    30                  35                  40 tta caa caa aac tgg caa ttt ggg gca aaa ccc aaa aat tca gaa atc         2416
Leu Gln Gln Asn Trp Gln Phe Gly Ala Lys Pro Lys Asn Ser Glu Ile
45                  50                  55 agt gaa tta ctc aat caa tta gcg aca ttg cta cag tcc gta att ccg         2464
Ser Glu Leu Leu Asn Gln Leu Ala Thr Leu Leu Gln Ser Val Ile Pro
60                  65                  70                  75 tta aaa aac agc cta caa att ttg caa caa aat tgt act caa att atg         2512
Leu Lys Asn Ser Leu Gln Ile Leu Gln Gln Asn Cys Thr Gln Ile Met
            80                  85                  90 ctc aac aaa tgg ctt gaa cga ctg ctt caa tcc att gaa tct ggc tta         2560
Leu Asn Lys Trp Leu Glu Arg Leu Leu Gln Ser Ile Glu Ser Gly Leu
            95                  100                 105 gca ttc tca caa gcc att gaa caa caa gga aaa tat ctc aca caa caa         2608
Ala Phe Ser Gln Ala Ile Glu Gln Gln Gly Lys Tyr Leu Thr Gln Gln
    110                 115                 120 gaa att caa ctg att caa gtg gga gaa atg aca gga aaa ctt gcc gta         2656
Glu Ile Gln Leu Ile Gln Val Gly Glu Met Thr Gly Lys Leu Ala Val
125                 130                 135 gtt tgt aaa aaa ata gcc acg cac cgt agt caa tct ttg gct tta caa         2704
Val Cys Lys Lys Ile Ala Thr His Arg Ser Gln Ser Leu Ala Leu Gln
140                 145                 150                 155 cgc aaa tta cag aaa att atg tta tat ccc tca atg gta ttg gga att         2752
Arg Lys Leu Gln Lys Ile Met Leu Tyr Pro Ser Met Val Leu Gly Ile
            160                 165                 170 tct cta tta ttg aca ctc gca tta ctg ctt ttt atc gcg cct caa ttt         2800
Ser Leu Leu Leu Thr Leu Ala Leu Leu Leu Phe Ile Ala Pro Gln Phe
            175                 180                 185 gct gaa atg tac agt ggc aat aat gcg gag tta cca aca ata acc gca         2848
Ala Glu Met Tyr Ser Gly Asn Asn Ala Glu Leu Pro Thr Ile Thr Ala
            190                 195                 200 ata ttg ctc tca ata tct aat ttc ctt aag caa aat att ggc att ttg         2896
Ile Leu Leu Ser Ile Ser Asn Phe Leu Lys Gln Asn Ile Gly Ile Leu
205                 210                 215 cta ttt ttc gtt ttg agt ttt ttt cta ttt tat tat ttc tat cta aaa         2944
Leu Phe Phe Val Leu Ser Phe Phe Leu Phe Tyr Tyr Phe Tyr Leu Lys
220                 225                 230                 235 cgc cag act tgg ttt cat caa aag aaa aat caa ctt att tct atc acg         2992
Arg Gln Thr Trp Phe His Gln Lys Lys Asn Gln Leu Ile Ser Ile Thr
            240                 245                 250 cct att ttt ggc aca att caa aag ctt tca cgt tta gtg aac ttt agt         3040
Pro Ile Phe Gly Thr Ile Gln Lys Leu Ser Arg Leu Val Asn Phe Ser
            255                 260                 265 caa agt tta caa att atg ttg cag gcc ggc gta ccg ctt aat cag gca         3088
Gln Ser Leu Gln Ile Met Leu Gln Ala Gly Val Pro Leu Asn Gln Ala
    270                 275                 280 cta gac agt ttt ctt cct cgc aca caa act tgg caa acc aag aaa acg         3136
Leu Asp Ser Phe Leu Pro Arg Thr Gln Thr Trp Gln Thr Lys Lys Thr
285                 290                 295 ctt gta aac gat atg gta tta gat aaa gaa gtg cgg tca att ttg caa         3184
Leu Val Asn Asp Met Val Leu Asp Lys Glu Val Arg Ser Ile Leu Gln
300                 305                 310                 315
```

```
tgg gtt tct caa ggc tat gcg ttt tct aat agc gta agt agc gat ctt    3232
Trp Val Ser Gln Gly Tyr Ala Phe Ser Asn Ser Val Ser Ser Asp Leu
            320                 325                 330 ttc ccg atg gaa gca caa caa atg cta caa att ggc gaa caa agc gga    3280
Phe Pro Met Glu Ala Gln Gln Met Leu Gln Ile Gly Glu Gln Ser Gly
335                 340                 345 aaa ctc gct ttg atg cta gag cat atc gca gat aat tac caa gaa aaa    3328
Lys Leu Ala Leu Met Leu Glu His Ile Ala Asp Asn Tyr Gln Glu Lys
        350                 355                 360 ctt aat cat caa att gac tta ctc tca caa atg cta gaa cca tta atg    3376
Leu Asn His Gln Ile Asp Leu Leu Ser Gln Met Leu Glu Pro Leu Met
    365                 370                 375 atg gta atc atc ggc agt ctg att ggg att att atg atg gga atg tat    3424
Met Val Ile Ile Gly Ser Leu Ile Gly Ile Ile Met Met Gly Met Tyr
380                 385                 390                 395 tta cct atc ttt aat atg gga tca gtt att caa tga tttacttcac         3470
Leu Pro Ile Phe Asn Met Gly Ser Val Ile Gln
                400                 405 aatgtttta ttaggcggca tcttagggat cgcattgtgg ttctacctat ctggttttat    3530
tacgcatttg cagcaagaga tttatgcgac ttacgttgaa ttatttccac aaaacagttc    3590
tccatttcaa ccgcactttg cctctattca acaaaaaaag tgcggtcata ttttgaggta    3650
tttttttagt attggggttg gatttatatt tttacaaatt gccttcaaag attctatttt    3710
tactgtatgg atcggactca cacttattat tctttggaca atcagttatc ttgattggca    3770
ctatcaactt atttctacga cacctgtttt atggttactt actctcggtt tatttggcgc    3830
agacaataac ttttcattgc taacgttatc tgaaagcata aaaagtgcgg ctagtttttt    3890
tattgttttc tacgcaatct attggattgc aaaatgttat tatagaaaag aagcctttgg    3950
acggggagat tattggctag caatggcatt aggaagtttt attcatttag aaaccttacc    4010
gcactttta ttattagcct cagtgcttgg aatatgtttt tcgcttattc ataaaaagaa    4070
aaaagaattt ataccttttg ccccttttat gaacttatcg gctatcatta tttatctcgt    4130
caaatattac ggatattaaa aaggggaaaa cataatattt ttcccttgtt cttcatagaa    4190
gtgcggttgt ttttacgaac gtttcatcac ttcaaaaaac tcttcgttgg ttttcgccat    4250
catcagctta tcaatcaaga attccattgc atccacttca tccattggat taagaatctt    4310
acgaagaatc cacattttt gtaattcgtc cgctg                              4345

<210> SEQ ID NO 6
<211> LENGTH: 406
<212> TYPE: PRT
<213> ORGANISM: H. influenzae

<400> SEQUENCE: 6

Met Thr Lys Lys Leu Phe Tyr Tyr Gln Gly Ser Asn Ala Leu Asn Gln
1               5                   10                  15

Lys Gln Lys Gly Ser Ile Ile Ala Asp Thr Lys Gln Gln Ala His Phe
            20                  25                  30

Gln Leu Ile Ser Arg Gly Leu Thr His Ile Lys Leu Gln Asn Trp
        35                  40                  45

Gln Phe Gly Ala Lys Pro Lys Asn Ser Glu Ile Ser Glu Leu Leu Asn
    50                  55                  60

Gln Leu Ala Thr Leu Leu Gln Ser Val Ile Pro Leu Lys Asn Ser Leu
65                  70                  75                  80

Gln Ile Leu Gln Gln Asn Cys Thr Gln Ile Met Leu Asn Lys Trp Leu
```

```
                    85                  90                  95
Glu Arg Leu Leu Gln Ser Ile Glu Ser Gly Leu Ala Phe Ser Gln Ala
            100                 105                 110
Ile Glu Gln Gln Gly Lys Tyr Leu Thr Gln Gln Glu Ile Gln Leu Ile
        115                 120                 125
Gln Val Gly Glu Met Thr Gly Lys Leu Ala Val Val Cys Lys Lys Ile
    130                 135                 140
Ala Thr His Arg Ser Gln Ser Leu Ala Leu Gln Arg Lys Leu Gln Lys
145                 150                 155                 160
Ile Met Leu Tyr Pro Ser Met Val Leu Gly Ile Ser Leu Leu Leu Thr
                165                 170                 175
Leu Ala Leu Leu Leu Phe Ile Ala Pro Gln Phe Ala Glu Met Tyr Ser
            180                 185                 190
Gly Asn Asn Ala Glu Leu Pro Thr Ile Thr Ala Ile Leu Leu Ser Ile
        195                 200                 205
Ser Asn Phe Leu Lys Gln Asn Ile Gly Ile Leu Phe Phe Val Leu
    210                 215                 220
Ser Phe Phe Leu Phe Tyr Tyr Phe Tyr Leu Lys Arg Gln Thr Trp Phe
225                 230                 235                 240
His Gln Lys Lys Asn Gln Leu Ile Ser Ile Thr Pro Ile Phe Gly Thr
                245                 250                 255
Ile Gln Lys Leu Ser Arg Leu Val Asn Phe Ser Gln Ser Leu Gln Ile
            260                 265                 270
Met Leu Gln Ala Gly Val Pro Leu Asn Gln Ala Leu Asp Ser Phe Leu
        275                 280                 285
Pro Arg Thr Gln Thr Trp Gln Thr Lys Lys Thr Leu Val Asn Asp Met
    290                 295                 300
Val Leu Asp Lys Glu Val Arg Ser Ile Leu Gln Trp Val Ser Gln Gly
305                 310                 315                 320
Tyr Ala Phe Ser Asn Ser Val Ser Ser Asp Leu Phe Pro Met Glu Ala
                325                 330                 335
Gln Gln Met Leu Gln Ile Gly Glu Gln Ser Gly Lys Leu Ala Leu Met
            340                 345                 350
Leu Glu His Ile Ala Asp Asn Tyr Gln Glu Lys Leu Asn His Gln Ile
        355                 360                 365
Asp Leu Leu Ser Gln Met Leu Glu Pro Leu Met Met Val Ile Ile Gly
    370                 375                 380
Ser Leu Ile Gly Ile Ile Met Met Gly Tyr Leu Pro Ile Phe Asn
385                 390                 395                 400
Met Gly Ser Val Ile Gln
            405

<210> SEQ ID NO 7
<211> LENGTH: 4345
<212> TYPE: DNA
<213> ORGANISM: H. influenzae
<220> FEATURE:
<221> NAME/KEY: CDS
<222> LOCATION: (3457)..(4149)

<400> SEQUENCE: 7
gcgatcatta aaattgacat attgcgtaat tcgcccattt cgttcgatca acaatgtgc      60 tgaaacacgc atttgataaa tttctgcaaa ataaggatga atcttaggat ctaattttcc    120
ttgaaaaaaa tcatccacat atccgccgcc aaattgttct ggcggcagac taatataatg   180
```

-continued

```
aataaccaat aaggaaatat cctgtggatt tgggcgttta tcgaagtgag gtgactgaat    240
ttgccgacaa tccaatatac cttgttcaat atctttagt ttttgcatac ttttttcctt    300
tttttgcgat caggatcgca gaaaaagtgc ggtcaatttt acaaacaaat ttttcctttt    360
cacaatgtcg tcgctaacaa aggcttaata aaaggaaaat gaatgaaact aacaacacag    420
caaaccttga aaaagggtt tacattaata gagctaatga ttgtgattgc aattattgct     480
attttagcca ctatcgcaat tccctcttat caaaattata ctaaaaaagc agcggtatct    540
gaattactgc aagcgtcagc gccttataag gctgatgtgg aattatgtgt atatagcaca    600
aatgaaacaa caaactgtac gggtggaaaa atggtattg cagcagatat aaccacagca     660
aaaggctatg taaatcagt gacaacaagc aacggtgcaa taacagtaaa aggggatggc     720
acattggcaa atatggaata tattttgcaa gctacaggta atgctgcaac aggtgtaact    780
tggacaacaa cttgcaaagg aacggatgcc tctttatttc cagcaaattt ttgcggaagt    840
gtcacacaat gacgagctat gctttacttc atactcagcg tgtaaccgct caaaatggcg    900
agatctttac gatctcgcca gatttatggg aacgcaatca gcagcaacaa tccttgctct    960
tgcggtattt tgctttgcca cttaaagaag aaaataatcg tctttggcta ggggttgatt   1020
ctctctccaa tctttcagct tgtgaaacca ttgcgtttat aacaggaaaa cctgtcgaac   1080
caattttgtt agaaagcagc caactcaaag aactgttaca acaacttact ccgcaccaaa   1140
tgcaagtgga agagcaagtt aaattctatc aacatcaaga aacccatttt gaacaagaag   1200
atgatgaacc tgttatccgc ttacttaatc agattttga atctgcctta caaaaaaatg    1260
cctctgatat tcatttagaa accttggctg atcagtttca agtgcggttt agaattgatg   1320
gtgttttaca accacaaccc ttaataagca aaatattcgc caatcgtatt atttcacgct   1380
taaaattact ggctaaatta gatattagtg aaaatcgact tccacaagat ggacgatttc   1440
aatttaaaac cactttttcc gatattcttg attttcgcct ttcaaccttta ccaacccatt  1500 ggggcgaaaa atcgtgttg cgagcgcaac aaaataaacc tgtagaactt agctttgctg    1560
aactgggtat gaccgaaaat cagcaacaag catttcaacg ctcacttagc cagccacaag   1620
gattaatttt agtaaccggc cccacaggaa gtgggaaaag tatctcgctt tacaccgcac   1680
ttcagtggct aaatacgcct gataaacata ttatgaccgc tgaagatccc attgaaattg   1740
aacttgatgg tattattcaa agccaaatta atccgcagat tggattagat tttagccgtc   1800
tattgcgtgc ttttttacgt caagatcccg acatcattat gctaggtgaa attcgagatg   1860
aagaaagtgc aaggattgca ctacgtgccg ctcaaacggg acatttggtg cttttcaactt  1920 tacataccaa tgatgcaata tctgccattt ctcgcttaca acaactcggt attcaacaac   1980
atgaaattga aaacagttta ctactcgtca ttgcacagcg tcttgtacga aaaatctgtc   2040
caaagtgcgg tggaaattta ataaattctt gtgattgcca tcaaggttat cgagggcgaa   2100
tcggcgtgta tcaatttcta cattggcaac agaatggcta tcaaacggat tttgagaatt   2160
tacgagagag tggtttggaa aaagttagcc aaggcataac agatgagaaa gaaattgaac   2220
gtgtgttagg taaaaactca tgactaaaaa actcttttat tatcaaggta gtaacgcatt   2280
aaatcagaaa caaaaaggct caattattgc ggatacgaaa caacaagcgc actttcagtt   2340
aataagccgc gggcttactc acatcaaatt acaacaaaac tggcaatttg gggcaaaacc   2400
caaaaattca gaaatcagtg aattactcaa tcaattagcg acattgctac agtccgtaat   2460
tccgttaaaa aacagcctac aaattttgca acaaaattgt actcaaatta tgctcaacaa   2520
atggcttgaa cgactgcttc aatccattga atctggctta gcattctcac aagccattga   2580
```

| | |
|---|---|
| acaacaagga aaatatctca cacaacaaga aattcaactg attcaagtgg gagaaatgac | 2640 |
| aggaaaactt gccgtagttt gtaaaaaaat agccacgcac cgtagtcaat ctttggcttt | 2700 |
| acaacgcaaa ttacagaaaa ttatgttata tccctcaatg gtattgggaa tttctctatt | 2760 |
| attgacactc gcattactgc tttttatcgc gcctcaattt gctgaaatgt acagtggcaa | 2820 |
| taatgcggag ttaccaacaa taaccgcaat attgctctca atatctaatt tccttaagca | 2880 |
| aaatattggc attttgctat ttttcgtttt gagttttttt ctattttatt atttctatct | 2940 |
| aaaacgccag acttggtttc atcaaaagaa aaatcaactt atttctatca cgcctatttt | 3000 |
| tggcacaatt caaaagcttt cacgtttagt gaactttagt caaagtttac aaattatgtt | 3060 |
| gcaggccggc gtaccgctta atcaggcact agacagtttt cttcctcgca cacaaacttg | 3120 |
| gcaaaccaag aaaacgcttg taacgatat ggtattagat aaagaagtgc ggtcaatttt | 3180 |
| gcaatgggtt tctcaaggct atgcgttttc taatagcgta agtagcgatc ttttcccgat | 3240 |
| ggaagcacaa caaatgctac aaattggcga acaaagcgga aaactcgctt tgatgctaga | 3300 |
| gcatatcgca gataattacc aagaaaaact taatcatcaa attgacttac tctcacaaat | 3360 |
| gctagaacca ttaatgatgg taatcatcgg cagtctgatt gggattatta tgatgggaat | 3420 |

| | | |
|---|---|---|
| gtatttacct atctttaata tgggatcagt tattca atg att tac ttc aca atg<br>                                           Met Ile Tyr Phe Thr Met<br>                                              1                  5 | 3474 |
| ttt tta tta ggc ggc atc tta ggg atc gca ttg tgg ttc tac cta tct<br>Phe Leu Leu Gly Gly Ile Leu Gly Ile Ala Leu Trp Phe Tyr Leu Ser<br>              10                    15                    20 | 3522 |
| ggt ttt att acg cat ttg cag caa gag att tat gcg act tac gtt gaa<br>Gly Phe Ile Thr His Leu Gln Gln Glu Ile Tyr Ala Thr Tyr Val Glu<br>         25                    30                    35 | 3570 |
| tta ttt cca caa aac agt tct cca ttt caa ccg cac ttt gcc tct att<br>Leu Phe Pro Gln Asn Ser Ser Pro Phe Gln Pro His Phe Ala Ser Ile<br>40                       45                    50 | 3618 |
| caa caa aaa aag tgc ggt cat att ttg agg tat ttt ttt agt att ggg<br>Gln Gln Lys Lys Cys Gly His Ile Leu Arg Tyr Phe Phe Ser Ile Gly<br>55                60                    65                    70 | 3666 |
| gtt gga ttt ata ttt tta caa att gcc ttc aaa gat tct att ttt act<br>Val Gly Phe Ile Phe Leu Gln Ile Ala Phe Lys Asp Ser Ile Phe Thr<br>              75                    80                    85 | 3714 |
| gta tgg atc gga ctc aca ctt att att ctt tgg aca atc agt tat ctt<br>Val Trp Ile Gly Leu Thr Leu Ile Ile Leu Trp Thr Ile Ser Tyr Leu<br>         90                    95                    100 | 3762 |
| gat tgg cac tat caa ctt att tct acg aca ccc tgt tta tgg tta ctt<br>Asp Trp His Tyr Gln Leu Ile Ser Thr Thr Pro Cys Leu Trp Leu Leu<br>         105                    110                    115 | 3810 |
| act ctc ggt tta ttt ggc gca gac aat aac ttt tca ttg cta acg tta<br>Thr Leu Gly Leu Phe Gly Ala Asp Asn Asn Phe Ser Leu Leu Thr Leu<br>         120                    125                    130 | 3858 |
| tct gaa agc ata aaa agt gcg gct agt ttt ttt att gtt ttc tac gca<br>Ser Glu Ser Ile Lys Ser Ala Ala Ser Phe Phe Ile Val Phe Tyr Ala<br>135                       140                    145                    150 | 3906 |
| atc tat tgg att gca aaa tgt tat tat aga aaa gaa gcc ttt gga cgg<br>Ile Tyr Trp Ile Ala Lys Cys Tyr Tyr Arg Lys Glu Ala Phe Gly Arg<br>              155                    160                    165 | 3954 |
| gga gat tat tgg cta gca atg gca tta gga agt ttt att cat tta gaa<br>Gly Asp Tyr Trp Leu Ala Met Ala Leu Gly Ser Phe Ile His Leu Glu<br>         170                    175                    180 | 4002 |
| acc tta ccg cac ttt tta tta tta gcc tca gtg ctt gga ata tgt ttt<br>Thr Leu Pro His Phe Leu Leu Leu Ala Ser Val Leu Gly Ile Cys Phe | 4050 |

-continued

```
                185                 190                 195
tcg ctt att cat aaa aag aaa aaa gaa ttt ata cct ttt gcc cct ttt    4098
Ser Leu Ile His Lys Lys Lys Lys Glu Phe Ile Pro Phe Ala Pro Phe
    200                 205                 210 atg aac tta tcg gct atc att att tat ctc gtc aaa tat tac gga tat    4146
Met Asn Leu Ser Ala Ile Ile Ile Tyr Leu Val Lys Tyr Tyr Gly Tyr
215                 220                 225                 230 taa aaagggaaa acataatatt tttcccttgt tcttcataga agtgcggttg          4199
tttttacgaa cgtttcatca cttcaaaaaa ctcttcgttg gttttcgcca tcatcagctt  4259
atcaatcaag aattccattg catccacttc atccattgga ttaagaatct tacgaagaat  4319
ccacattttt tgtaattcgt ccgctg                                      4345
```

<210> SEQ ID NO 8
<211> LENGTH: 230
<212> TYPE: PRT
<213> ORGANISM: H. influenzae

<400> SEQUENCE: 8

Met Ile Tyr Phe Thr Met Phe Leu Leu Gly Gly Ile Leu Gly Ile Ala
1               5                   10                  15

Leu Trp Phe Tyr Leu Ser Gly Phe Ile Thr His Leu Gln Gln Glu Ile
            20                  25                  30

Tyr Ala Thr Tyr Val Glu Leu Phe Pro Gln Asn Ser Ser Pro Phe Gln
        35                  40                  45

Pro His Phe Ala Ser Ile Gln Gln Lys Lys Cys Gly His Ile Leu Arg
    50                  55                  60

Tyr Phe Phe Ser Ile Gly Val Gly Phe Ile Phe Leu Gln Ile Ala Phe
65                  70                  75                  80

Lys Asp Ser Ile Phe Thr Val Trp Ile Gly Leu Thr Leu Ile Ile Leu
                85                  90                  95

Trp Thr Ile Ser Tyr Leu Asp Trp His Tyr Gln Leu Ile Ser Thr Thr
            100                 105                 110

Pro Cys Leu Trp Leu Leu Thr Leu Gly Leu Phe Gly Ala Asp Asn Asn
        115                 120                 125

Phe Ser Leu Leu Thr Leu Ser Glu Ser Ile Lys Ser Ala Ala Ser Phe
    130                 135                 140

Phe Ile Val Phe Tyr Ala Ile Tyr Trp Ile Ala Lys Cys Tyr Tyr Arg
145                 150                 155                 160

Lys Glu Ala Phe Gly Arg Gly Asp Tyr Trp Leu Ala Met Ala Leu Gly
                165                 170                 175

Ser Phe Ile His Leu Glu Thr Leu Pro His Phe Leu Leu Ala Ser
            180                 185                 190

Val Leu Gly Ile Cys Phe Ser Leu Ile His Lys Lys Lys Glu Phe
        195                 200                 205

Ile Pro Phe Ala Pro Phe Met Asn Leu Ser Ala Ile Ile Ile Tyr Leu
    210                 215                 220

Val Lys Tyr Tyr Gly Tyr
225                 230

<210> SEQ ID NO 9
<211> LENGTH: 4864
<212> TYPE: DNA
<213> ORGANISM: H. influenzae
<220> FEATURE:
<221> NAME/KEY: CDS
<222> LOCATION: (517)..(1314)

<400> SEQUENCE: 9

```
tacgaataat ggttttttct ggggttaaga aaaagttacg cgctaattgt tgagtaatcg      60
tacttgcacc ttgtgatgca ccgccattac tcactgcgac aaacaatgca cgagcaatgc     120
cgatagggtc taatccgtga tgatcgtaaa acgattgtc ttccgttgct aaaaatgcgt      180
caattaagcg ttgtggcaca tcggctaatt tcactggaat acggcgttgc tcgcccactt     240
cgccaattaa tttaccgtca gccgtataaa tctgcattgg ttgttgtaat tcaacggttc     300
ttaatgtttc tactgagggc aattccgatt ttaggtggaa atacaacatt ccgccagcca     360
ctaaacctaa aatacataaa gttaataggg tgtttaatat taattttgcg atccgcatcg     420
taaaattctc gcttggttaa tgaatattct tgtcaagaga cctatgattt agttgttaag     480
tataaaagat tcagccttta aagaatagga agaat atg caa ttc tcc ctg aaa        534
                                    Met Gln Phe Ser Leu Lys
                                     1               5 aat tac cgc act tta caa atc ggc att cat cgt aag cag ggt tat ttt       582
Asn Tyr Arg Thr Leu Gln Ile Gly Ile His Arg Lys Gln Gly Tyr Phe
            10                  15                  20 gat ttt gtg tgg ttt gat gat ctt gaa cag cca caa agt tat caa att       630
Asp Phe Val Trp Phe Asp Asp Leu Glu Gln Pro Gln Ser Tyr Gln Ile
        25                  30                  35 ttt gtt aat gat cgt gat ttt aaa aat cgt ttt tta caa cag cta aaa       678
Phe Val Asn Asp Arg Asp Phe Lys Asn Arg Phe Leu Gln Gln Leu Lys
    40                  45                  50 aca caa tat caa ggg aaa acc ttt cct tta cag ttt gtg gca agc att       726
Thr Gln Tyr Gln Gly Lys Thr Phe Pro Leu Gln Phe Val Ala Ser Ile
55                  60                  65                  70 ccc gct cac tta act tgg tcg aaa gta tta atg ttg cca caa gtg tta       774
Pro Ala His Leu Thr Trp Ser Lys Val Leu Met Leu Pro Gln Val Leu
                75                  80                  85 aat gcg caa gaa tgt cat caa caa tgt aaa ttt gtg att gaa aaa gag       822
Asn Ala Gln Glu Cys His Gln Gln Cys Lys Phe Val Ile Glu Lys Glu
            90                  95                 100 ctg cct att tct tta aat gaa tta tgg ttt gat tat cgt tct acc tcg       870
Leu Pro Ile Ser Leu Asn Glu Leu Trp Phe Asp Tyr Arg Ser Thr Ser
        105                 110                 115 tta aag caa ggt ttt cga tta gac gtt act gca att cgt aaa agt act       918
Leu Lys Gln Gly Phe Arg Leu Asp Val Thr Ala Ile Arg Lys Ser Thr
    120                 125                 130 gct caa act tat ttg caa gat ttt cag cca ttt aaa att aat gta ttg       966
Ala Gln Thr Tyr Leu Gln Asp Phe Gln Pro Phe Lys Ile Asn Val Leu
135                 140                 145                 150 gat gtt gcg tca aat gct att ttg cgt gca ttt cag tat ttg ttg aat      1014
Asp Val Ala Ser Asn Ala Ile Leu Arg Ala Phe Gln Tyr Leu Leu Asn
                155                 160                 165 gaa caa gtg cgg tca gaa aat acc tta ttt tta ttt caa gaa gat gac      1062
Glu Gln Val Arg Ser Glu Asn Thr Leu Phe Leu Phe Gln Glu Asp Asp
            170                 175                 180 tat tgt ttg gcg atc tgt gaa aga tcg cag caa tcg caa att tta caa      1110
Tyr Cys Leu Ala Ile Cys Glu Arg Ser Gln Gln Ser Gln Ile Leu Gln
        185                 190                 195 tct cac gaa aat ttg acc gca ctt tat gaa caa ttt acc gaa cgt ttt      1158
Ser His Glu Asn Leu Thr Ala Leu Tyr Glu Gln Phe Thr Glu Arg Phe
    200                 205                 210 gaa gga caa ctt gaa caa gtt ttt gtt tat caa att ccc tca agt cat      1206
Glu Gly Gln Leu Glu Gln Val Phe Val Tyr Gln Ile Pro Ser Ser His
215                 220                 225                 230
```

-continued

```
aca cca tta ccc gaa aac tgg cag cga gta gaa aca gaa ctc cct ttt      1254
Thr Pro Leu Pro Glu Asn Trp Gln Arg Val Glu Thr Glu Leu Pro Phe
            235                 240                 245 att gcg ctt ggc aac gcg cta tgg caa aaa gat tta cat caa caa aaa      1302
Ile Ala Leu Gly Asn Ala Leu Trp Gln Lys Asp Leu His Gln Gln Lys
        250                 255                 260 gtg ggt ggt taa atgtcgatga atttattgcc ttggcgtact tatcaacatc          1354
Val Gly Gly
        265 aaaagcgttt acgtcgttta gcttttata tcgctttatt tatcttgctt gctattaatt    1414
taatgttggc tttagcaat ttgattgaac aacagaaaca aaatttgcaa gcgcagcaaa    1474
catcttttga acaacttaat cagcaacttc acaaaactac catgcaaatt gatcagttac   1534
gcagtgcggt gaaagttggt gaagttttga catctattcc caacgagcaa gtaaaaaaga   1594
gtttacaaca gctaagtgaa ttaccttttc aacaaggaga actgaataaa tttaaacaag   1654
atgccaataa cttaagtttg gaaggtaacg cgcaagatca aacagaattt gaactgattc   1714
atcaattttt aaagaaacat tttcccaatg tgaaattaag tcaggttcaa cctgaacaag   1774
atacattgtt ttttcacttt gatgtggaac aaggggcgga aaaatgaaag cttttttttaa  1834
cgatcctttt actccttttg gaaaatggct aagtcagcct ttttatgtgc acggtttaac   1894
ctttttattg ctattaagtg cggtgatttt tcgccccgtt ttagattata tcgaggggag   1954
ttcacgtttc catgaaattg aaaatgagtt agcggtgaaa cgttcagaat gttgcatca    2014
acagaaaatt ttaacttctt tacagcagca gtcggaaagt cgaaaacttt ctccagaact   2074
ggctgcacaa attattcctt tgaataaaca aattcaacgt ttagctgcgc gtaacggttt   2134
atctcagcat ttacgttggg aaatgggggca aaagccatt ttgcatttac agcttacagg   2194
tcattttgag aaaacgaaga cattttttaac cgcacttttg gctaattcgt cacagctttc  2254
agtgagtcgc ttgcagttta tcaaacccga agacaaccca ttgcaaaccg agatcatttt   2314
tcagctagat aaggaaacaa atgaaacat tggtttttcc tgattatatt attttttatg    2374
aattgcagtt ggggacaaga tccttttcgat aaaacacagc gtaaccgttc tcagtttgat  2434
aacgcacaaa cagtaatgga gcagacagaa ataatttcct cagatgtacc taataatcta   2494
tgcggagcgg atgaaaatcg ccaagcggct gaaattcctt gaacgctttt aaaattggtg   2554
ggcgtagtga tttctaaaga taaagccttt gccttgttgc aagatcaagg tttgcaaatt   2614
tacagcgttt tagagggcgt tgatgtggct caagagggct atattgtaga aaaaatcaac   2674
caaaacaatg ttcaatttat gcgtaagctc ggagagcaat gtgatagtag tgaatggaaa   2734
aaattaagtt tttaaaggaa gattatgaag aaatatttt taaagtgcgg ttattttta    2794
gtgtgttttt gtttgccatt aatcgttttt gctaatccta aaacagataa cgaatgtttt   2854
tttattcgtt tatcgcaagc acctttagct caaacactgg agcaattagc ttttcaacaa   2914
gatgtgaatt tagtgatggg tgagaggtta gaaggcaata tttctttgaa attaaacaat   2974
attgatatgc cacgtttgct aaaaataatc gcaaaagta agcatcttac tttgaataaa    3034
gatgatgggg tttattattt aaacggcagt caatctggca aaggtcaagt tgcaggaaat   3094
cttacgacaa atgaaccgca cttagtcagc cacacggtaa aacttcattt tgctaaagcc   3154
tctgaattaa tgaaatcctt aacaacagga agtggatctt tgctttcttc tgcggggagc   3214
attaccttttg atgatcgcag taatttgctg gttattcagg atgaacctcg ttttgtgcaa  3274
aatatcaaaa aactgattgc tgaaatggat aagcctattg aacagatcgc tattgaagcg   3334
cgaattgtga caattacgga tgagagtttg aaagaacttg gcgttcggtg ggggattttt   3394
```

```
aatccaactg aaaatgcaag acgagttgcg ggcagcctta caggcaatag ctttgaaaat   3454
attgcggata atcttaatgt aaattttgcg acaacgacga cacctgctgg ctctatagca   3514
ttacaagtcg cgaaaattaa tgggcgattg cttgatttag aattgagtgc gttggagcgt   3574
gaaaataatg tagaaattat tgcaagtcct cgcttactca ctaccaataa gaaaagtgcg   3634
agcattaaac aggggacaga aattccttac atcgtgagta atactcgtaa cgatacgcaa   3694
tctgtggaat tcgtgaggc agtacttggt ttggaagtga cgccacatat ttctaaagat   3754
aacaatatct tacttgattt attggtaagt caaaattccc ctggttctcg tgtcgcttat   3814
ggacaaaatg aggtggtttc tattgataag caagaaatta atactcaggt ttttgccaaa   3874
gatggggaaa ccattgtgct tggcggcgta tttcacgaca caatcacgaa agcgaagat   3934
aaagtgccat tgcttggcga tatcccgtt attaaacgat tatttagcaa agaaagtgaa   3994
cgacatcaaa aacgtgagct cgtgattttc gtcacgccgc atattttaaa agcaggagaa   4054
acgttagagg cgttgaaaca aaaaagtgcg gggaaaaaat aactttttta gacgatgaat   4114
tttttttaatt ttcgctgtat ccactgtcgt ggcaatcttc atattgcaaa aaatgggcta   4174
tgttcaggtt gccaaaaaca aattaaatct tttccttatt gcggtcattg tggtgcggaa   4234
ttgcaatatt atgcgcagca ttgtggtaat tgtcttaaac aagaaccaag ttgggataag   4294
atggtcatta ttgggcatta tattgaacct ctttcgatat tgattcaccg ttttaaattt   4354
caaaatcaat tttggattga ccgcacttta gctcggcttt tatatcttgc ggtgcgtgat   4414
gctaaacgaa cgcatcaact taaattgcca gaagcaatca ttccagtgcc tttatatcat   4474
tttcgtcagt ggcgacgggg ttataatcag gcagatttat tatctcggca attaagtcgc   4534
tggctggata ttcctaattt gagcaatatc gtaaagcgtg tgaaacacac ctatactcaa   4594
cgtggtttga gtgcaaaaga tcgtcgtcag aatttaaaaa atgccttttc tcttgttgtt   4654
tcgaaaaatg aatttcctta tcgccgtgtt gcgttggtgg atgatgtgat tactactggt   4714
tctacactca atgaaatctc aaaattgttg cgaaaattag gtgtggagga gattcaagtg   4774
tgggggctgg cacagagctta atataaagca ctggaaaaaa aagcgcgata agcgtattat   4834
tcccgatact ttctctcaag tatttaggac                                   4864
```

<210> SEQ ID NO 10
<211> LENGTH: 265
<212> TYPE: PRT
<213> ORGANISM: H. influenzae

<400> SEQUENCE: 10

```
Met Gln Phe Ser Leu Lys Asn Tyr Arg Thr Leu Gln Ile Gly Ile His
1               5                   10                  15

Arg Lys Gln Gly Tyr Phe Asp Phe Val Trp Phe Asp Asp Leu Glu Gln
            20                  25                  30

Pro Gln Ser Tyr Gln Ile Phe Val Asn Asp Arg Asp Phe Lys Asn Arg
        35                  40                  45

Phe Leu Gln Gln Leu Lys Thr Gln Tyr Gln Gly Lys Thr Phe Pro Leu
    50                  55                  60

Gln Phe Val Ala Ser Ile Pro Ala His Leu Thr Trp Ser Lys Val Leu
65                  70                  75                  80

Met Leu Pro Gln Val Leu Asn Ala Gln Glu Cys His Gln Cys Lys
                85                  90                  95

Phe Val Ile Glu Lys Glu Leu Pro Ile Ser Leu Asn Glu Leu Trp Phe
            100                 105                 110
```

-continued

```
Asp Tyr Arg Ser Thr Ser Leu Lys Gln Gly Phe Arg Leu Asp Val Thr
            115                 120                 125

Ala Ile Arg Lys Ser Thr Ala Gln Thr Tyr Leu Gln Asp Phe Gln Pro
        130                 135                 140

Phe Lys Ile Asn Val Leu Asp Val Ala Ser Asn Ala Ile Leu Arg Ala
145                 150                 155                 160

Phe Gln Tyr Leu Leu Asn Glu Gln Val Arg Ser Glu Asn Thr Leu Phe
                165                 170                 175

Leu Phe Gln Glu Asp Asp Tyr Cys Leu Ala Ile Cys Glu Arg Ser Gln
            180                 185                 190

Gln Ser Gln Ile Leu Gln Ser His Glu Asn Leu Thr Ala Leu Tyr Glu
        195                 200                 205

Gln Phe Thr Glu Arg Phe Glu Gly Gln Leu Glu Gln Val Phe Val Tyr
    210                 215                 220

Gln Ile Pro Ser Ser His Thr Pro Leu Pro Glu Asn Trp Gln Arg Val
225                 230                 235                 240

Glu Thr Glu Leu Pro Phe Ile Ala Leu Gly Asn Ala Leu Trp Gln Lys
                245                 250                 255

Asp Leu His Gln Gln Lys Val Gly Gly
            260                 265

<210> SEQ ID NO 11
<211> LENGTH: 4864
<212> TYPE: DNA
<213> ORGANISM: H. influenzae
<220> FEATURE:
<221> NAME/KEY: CDS
<222> LOCATION: (1321)..(1821)

<400> SEQUENCE: 11
tacgaataat ggttttttct ggggttaaga aaaagttacg cgctaattgt tgagtaatcg      60
tacttgcacc ttgtgatgca ccgccattac tcactgcgac aaacaatgca cgagcaatgc     120
cgatagggtc taatccgtga tgatcgtaaa acgattgtc ttccgttgct aaaaatgcgt      180
caattaagcg ttgtggcaca tcggctaatt tcactggaat acggcgttgc tcgcccactt     240
cgccaattaa tttaccgtca gccgtataaa tctgcattgg ttgttgtaat tcaacggttc     300
ttaatgtttc tactgagggc aattccgatt ttaggtggaa atacaacatt ccgccagcca     360
ctaaacctaa aatacataaa gttaataggg tgtttaatat taattttgcg atccgcatcg     420
taaaattctc gcttggttaa tgaatattct tgtcaagaga cctatgattt agttgttaag     480
tataaaagat tcagccttta aagaatagga aagaatatgc aattctccct gaaaaattac     540
cgcactttac aaatcggcat tcatcgtaag cagggttatt ttgattttgt gtggtttgat     600
gatcttgaac agccacaaag ttatcaaatt tttgttaatg atcgtgattt taaaaatcgt     660 ttttacaac agctaaaaac acaatatcaa gggaaaccct ttcctttaca gtttgtggca     720
agcattcccg ctcacttaac ttggtcgaaa gtattaatgt tgccacaagt gttaaatgcg     780
caagaatgtc atcaacaatg taaatttgtg attgaaaaag agctgcctat ttctttaaat     840
gaattatggt ttgattatcg ttctacctcg ttaaagcaag gttttcgatt agacgttact     900
gcaattcgta aaagtactgc tcaaactttat ttgcaagatt tcagccatt taaaattaat     960 gtattggatg ttgcgtcaaa tgctattttg cgtgcatttc agtatttgtt gaatgaacaa    1020
gtgcggtcag aaaataccct ttatttttattt caagaagatg actattgttt ggcgatctgt    1080
gaaagatcgc agcaatcgca aattttacaa tctcacgaaa atttgaccgc actttatgaa    1140
```

```
caatttaccg aacgttttga aggacaactt gaacaagttt ttgtttatca aattccctca    1200
agtcatacac cattacccga aaactggcag cgagtagaaa cagaactccc ttttattgcg    1260
cttggcaacg cgctatggca aaaagattta catcaacaaa aagtgggtgg ttaaatgtcg    1320
```

| | | | | | | | | | | | | | | | | |
|---|---|---|---|---|---|---|---|---|---|---|---|---|---|---|---|---|
| atg | aat | tta | ttg | cct | tgg | cgt | act | tat | caa | cat | caa | aag | cgt | tta | cgt | 1368 |
| Met | Asn | Leu | Leu | Pro | Trp | Arg | Thr | Tyr | Gln | His | Gln | Lys | Arg | Leu | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgt | tta | gct | ttt | tat | atc | gct | tta | ttt | atc | ttg | ctt | gct | att | aat | tta | 1416 |
| Arg | Leu | Ala | Phe | Tyr | Ile | Ala | Leu | Phe | Ile | Leu | Leu | Ala | Ile | Asn | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| atg | ttg | gct | ttt | agc | aat | ttg | att | gaa | caa | cag | aaa | caa | aat | ttg | caa | 1464 |
| Met | Leu | Ala | Phe | Ser | Asn | Leu | Ile | Glu | Gln | Gln | Lys | Gln | Asn | Leu | Gln | |
| | | | | 35 | | | | | 40 | | | | | 45 | | |

| | | | | | | | | | | | | | | | | |
|---|---|---|---|---|---|---|---|---|---|---|---|---|---|---|---|---|
| gcg | cag | caa | aca | tct | ttt | gaa | caa | ctt | aat | cag | caa | ctt | cac | aaa | act | 1512 |
| Ala | Gln | Gln | Thr | Ser | Phe | Glu | Gln | Leu | Asn | Gln | Gln | Leu | His | Lys | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| acc | atg | caa | att | gat | cag | tta | cgc | agt | gcg | gtg | aaa | gtt | ggt | gaa | gtt | 1560 |
| Thr | Met | Gln | Ile | Asp | Gln | Leu | Arg | Ser | Ala | Val | Lys | Val | Gly | Glu | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttg | aca | tct | att | ccc | aac | gag | caa | gta | aaa | aag | agt | tta | caa | cag | cta | 1608 |
| Leu | Thr | Ser | Ile | Pro | Asn | Glu | Gln | Val | Lys | Lys | Ser | Leu | Gln | Gln | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| agt | gaa | tta | cct | ttt | caa | caa | gga | gaa | ctg | aat | aaa | ttt | aaa | caa | gat | 1656 |
| Ser | Glu | Leu | Pro | Phe | Gln | Gln | Gly | Glu | Leu | Asn | Lys | Phe | Lys | Gln | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| gcc | aat | aac | tta | agt | ttg | gaa | ggt | aac | gcg | caa | gat | caa | aca | gaa | ttt | 1704 |
| Ala | Asn | Asn | Leu | Ser | Leu | Glu | Gly | Asn | Ala | Gln | Asp | Gln | Thr | Glu | Phe | |
| | | | | 115 | | | | | 120 | | | | | 125 | | |

| | | | | | | | | | | | | | | | | |
|---|---|---|---|---|---|---|---|---|---|---|---|---|---|---|---|---|
| gaa | ctg | att | cat | caa | ttt | tta | aag | aaa | cat | ttt | ccc | aat | gtg | aaa | tta | 1752 |
| Glu | Leu | Ile | His | Gln | Phe | Leu | Lys | Lys | His | Phe | Pro | Asn | Val | Lys | Leu | |
| | | 130 | | | | | 135 | | | | | 140 | | | | |

| | | | | | | | | | | | | | | | | |
|---|---|---|---|---|---|---|---|---|---|---|---|---|---|---|---|---|
| agt | cag | gtt | caa | cct | gaa | caa | gat | aca | ttg | ttt | ttt | cac | ttt | gat | gtg | 1800 |
| Ser | Gln | Val | Gln | Pro | Glu | Gln | Asp | Thr | Leu | Phe | Phe | His | Phe | Asp | Val | |
| 145 | | | | | 150 | | | | | 155 | | | | | 160 | |

| | | | | | | | |
|---|---|---|---|---|---|---|---|
| gaa | caa | ggg | gcg | gaa | aaa | tga | aagcttttt taacgatcct tttactcctt    1851 |
| Glu | Gln | Gly | Ala | Glu | Lys | | |
| | | | | 165 | | | |

```
ttggaaaatg gctaagtcag cctttttatg tgcacggttt aacctttta ttgctattaa    1911 gtgcggtgat ttttcgcccc gttttagatt atatcgaggg gagttcacgt ttccatgaaa    1971
ttgaaaatga gttagcggtg aaacgttcag aattgttgca tcaacagaaa attttaactt    2031
ctttacagca gcagtcggaa agtcgaaaac tttctccaga actggctgca caaattattc    2091
ctttgaataa acaaattcaa cgtttagctg cgcgtaacgg tttatctcag catttacgtt    2151
gggaaatggg gcaaaagcct attttgcatt tacagcttac aggtcatttt gagaaaacga    2211
agacattttt aaccgcactt ttggctaatt cgtcacagct ttcagtgagt cgcttgcagt    2271
ttatcaaacc cgaagacaac ccattgcaaa ccgagatcat ttttcagcta gataaggaaa    2331
caaaatgaaa cattggtttt tcctgattat attattttt atgaattgca gttggggaca    2391
agatcctttc gataaaacac agcgtaaccg ttctcagttt gataacgcac aaacagtaat    2451
ggagcagaca gaaataattt cctcagatgt acctaataat ctatgcggag cggatgaaaa    2511
tcgccaagcg gctgaaattc ctttgaacgc tttaaaattg gtgggcgtag tgatttctaa    2571
agataaagcc tttgccttgt tgcaagatca aggtttgcaa atttacgcg ttttagaggg    2631 cgttgatgtg gctcaagagg gctatattgt agaaaaaatc aaccaaaaca atgttcaatt    2691
```

```
tatgcgtaag ctcggagagc aatgtgatag tagtgaatgg aaaaaattaa gttttaaag    2751
gaagattatg aagaaatatt ttttaaagtg cggttatttt ttagtgtgtt tttgtttgcc    2811
attaatcgtt tttgctaatc ctaaaacaga taacgaatgt ttttttattc gtttatcgca    2871
agcacctta gctcaaacac tggagcaatt agcttttcaa caagatgtga atttagtgat    2931
gggtgagagg ttagaaggca atatttcttt gaaattaaac aatattgata tgccacgttt    2991
gctaaaaata atcgcaaaaa gtaagcatct tactttgaat aaagatgatg gggtttatta    3051
tttaaacggc agtcaatctg gcaaaggtca agttgcagga atcttacga caaatgaacc    3111
gcacttagtc agccacacgg taaaacttca ttttgctaaa gcctctgaat taatgaaatc    3171
cttaacaaca ggaagtggat ctttgctttc ttctgcgggg agcattacct ttgatgatcg    3231
cagtaatttg ctggttattc aggatgaacc tcgttttgtg caaatatca aaaaactgat    3291
tgctgaaatg gataagccta ttgaacagat cgctattgaa gcgcgaattg tgacaattac    3351
ggatgagagt ttgaaagaac ttggcgttcg gtgggggatt tttaatccaa ctgaaaatgc    3411
aagacgagtt gcgggcagcc ttacaggcaa tagctttgaa atattgcgg ataatcttaa    3471
tgtaaatttt gcgacaacga cgacacctgc tggctctata gcattacaag tcgcgaaaat    3531
taatgggcga ttgcttgatt tagaattgag tgcgttggag cgtgaaaata atgtagaaat    3591
tattgcaagt cctcgcttac tcactaccaa taagaaaagt gcgagcatta aacaggggac    3651
agaaattcct tacatcgtga gtaatactcg taacgatacg caatctgtgg aatttcgtga    3711
ggcagtactt ggtttggaag tgacgccaca tatttctaaa gataacaata tcttacttga    3771
tttattggta agtcaaaatt cccctggttc tcgtgtcgct tatggacaaa atgaggtggt    3831
ttctattgat aagcaagaaa ttaatactca ggttttttgcc aaagatgggg aaaccattgt    3891
gcttggcggc gtatttcacg acacaatcac gaaaagcgaa gataaagtgc cattgcttgg    3951
cgatataccc gttattaaac gattatttag caaagaaagt gaacgacatc aaaaacgtga    4011
gctcgtgatt ttcgtcacgc cgcatatttt aaaagcagga gaaacgttag aggcgttgaa    4071
acaaaaaagt gcggggaaaa ataacttttt ttagacgatg aattttttta attttcgctg    4131
tatccactgt cgtggcaatc ttcatattgc aaaaaatggg ctatgttcag gttgccaaaa    4191
acaaattaaa tcttttcctt attgcggtca ttgtggtgcg gaattgcaat attatgcgca    4251
gcattgtggt aattgtctta aacaagaacc aagttgggat aagatggtca ttattgggca    4311
ttatattgaa cctctttcga tattgattca ccgttttaaa tttcaaaatc aattttggat    4371
tgaccgcact ttagctcggc ttttatatct tgcggtgcgt gatgctaaac gaacgcatca    4431
acttaaattg ccagaagcaa tcattccagt gcctttatat catttcgtc agtggcgacg    4491
gggttataat caggcagatt tattatctcg gcaattaagt cgctggctgg atattcctaa    4551
tttgagcaat atcgtaaagc gtgtgaaaca cacctatact caacgtggtt tgagtgcaaa    4611
agatcgtcgt cagaatttaa aaaatgcctt ttctcttgtt gtttcgaaaa atgaatttcc    4671
ttatcgccgt gttgcgttgg tggatgatgt gattactact ggttctacac tcaatgaaat    4731
ctcaaaattg ttgcgaaaat taggtgtgga ggagattcaa gtgtggggc tggcacgagc    4791
ttaatataaa gcactggaaa aaaagcgcg ataagcgtat tattcccgat actttctctc    4851
aagtatttag gac                                                       4864
```

<210> SEQ ID NO 12
<211> LENGTH: 166
<212> TYPE: PRT
<213> ORGANISM: H. influenzae

<400> SEQUENCE: 12

```
Met Asn Leu Leu Pro Trp Arg Thr Tyr Gln His Gln Lys Arg Leu Arg
1               5                   10                  15

Arg Leu Ala Phe Tyr Ile Ala Leu Phe Ile Leu Ala Ile Asn Leu
            20                  25                  30

Met Leu Ala Phe Ser Asn Leu Ile Glu Gln Gln Lys Gln Asn Leu Gln
        35                  40                  45

Ala Gln Gln Thr Ser Phe Glu Gln Leu Asn Gln Leu His Lys Thr
    50                  55                  60

Thr Met Gln Ile Asp Gln Leu Arg Ser Ala Val Lys Val Gly Glu Val
65                  70                  75                  80

Leu Thr Ser Ile Pro Asn Glu Gln Val Lys Lys Ser Leu Gln Gln Leu
                85                  90                  95

Ser Glu Leu Pro Phe Gln Gln Gly Glu Leu Asn Lys Phe Lys Gln Asp
                100                 105                 110

Ala Asn Asn Leu Ser Leu Glu Gly Asn Ala Gln Asp Gln Thr Glu Phe
            115                 120                 125

Glu Leu Ile His Gln Phe Leu Lys Lys His Phe Pro Asn Val Lys Leu
        130                 135                 140

Ser Gln Val Gln Pro Glu Gln Asp Thr Leu Phe Phe His Phe Asp Val
145                 150                 155                 160

Glu Gln Gly Ala Glu Lys
                165
```

<210> SEQ ID NO 13
<211> LENGTH: 4864
<212> TYPE: DNA
<213> ORGANISM: H. influenzae
<220> FEATURE:
<221> NAME/KEY: CDS
<222> LOCATION: (1818)..(2339)

<400> SEQUENCE: 13

```
tacgaataat ggttttttct ggggttaaga aaaagttacg cgctaattgt tgagtaatcg    60
tacttgcacc ttgtgatgca ccgccattac tcactgcgac aaacaatgca cgagcaatgc   120
cgatagggtc taatccgtga tgatcgtaaa aacgattgtc ttccgttgct aaaaatgcgt   180
caattaagcg ttgtggcaca tcggctaatt tcactggaat acggcgttgc tcgcccactt   240
cgccaattaa tttaccgtca gccgtataaa tctgcattgg ttgttgtaat tcaacggttc   300
ttaatgtttc tactgagggc aattccgatt ttaggtggaa atacaacatt ccgccagcca   360
ctaaacctaa aatacataaa gttaataggg tgtttaatat taattttgcg atccgcatcg   420
taaaattctc gcttggttaa tgaatattct tgtcaagaga cctatgattt agttgttaag   480
tataaaagat tcagcccttta agaatagga agaatatgc aattctccct gaaaaattac   540
cgcactttac aaatcggcat tcatcgtaag cagggttatt ttgattttgt gtggtttgat   600
gatcttgaac agccacaaag ttatcaaatt tttgttaatg atcgtgattt taaaaatcgt   660
ttttacaac agctaaaaac acaatatcaa gggaaaacct ttcctttaca gtttgtggca   720
agcattcccg ctcacttaac ttggtcgaaa gtattaatgt tgccacaagt gttaaatgcg   780
caagaatgtc atcaacaatg taaatttgtg attgaaaaag agctgccat ttctttaaat   840
gaattatggt ttgattatcg ttctaccctcg ttaaagcaag ttttcgatt agacgttact   900
gcaattcgta aagtactgc tcaaacttat ttgcaagatt ttcagccatt taaaattaat   960
```

```
gtattggatg ttgcgtcaaa tgctattttg cgtgcatttc agtatttgtt gaatgaacaa    1020
gtgcggtcag aaaatacctt attttttattt caagaagatg actattgttt ggcgatctgt    1080
gaaagatcgc agcaatcgca aattttacaa tctcacgaaa atttgaccgc actttatgaa    1140
caatttaccg aacgttttga aggacaactt gaacaagttt ttgtttatca aattccctca    1200
agtcatacac cattacccga aaactggcag cgagtagaaa cagaactccc ttttattgcg    1260
cttggcaacg cgctatggca aaaagattta catcaacaaa aagtgggtgg ttaaatgtcg    1320
atgaatttat tgccttggcg tacttatcaa catcaaaagc gtttacgtcg tttagctttt    1380
tatatcgctt tatttatctt gcttgctatt aatttaatgt tggcttttag caatttgatt    1440
gaacaacaga acaaaattt gcaagcgcag caaacatctt ttgaacaact taatcagcaa    1500
cttcacaaaa ctaccatgca aattgatcag ttacgcagtg cggtgaaagt tggtgaagtt    1560
ttgacatcta ttcccaacga gcaagtaaaa aagagtttac aacagctaag tgaattacct    1620
tttcaacaag gagaactgaa taaatttaaa caagatgcca ataacttaag tttggaaggt    1680
aacgcgcaag atcaaacaga atttgaactg attcatcaat ttttaaagaa acattttccc    1740
aatgtgaaat taagtcaggt tcaacctgaa caagatacat tgttttttca ctttgatgtg    1800
```
gaacaagggg cggaaaaa atg aaa gct ttt ttt aac gat cct ttt act cct    1850
                                        Met Lys Ala Phe Phe Asn Asp Pro Phe Thr Pro
                                         1            5                10 ttt gga aaa tgg cta agt cag cct ttt tat gtg cac ggt tta acc ttt    1898
Phe Gly Lys Trp Leu Ser Gln Pro Phe Tyr Val His Gly Leu Thr Phe
          15                 20                 25 tta ttg cta tta agt gcg gtg att ttt cgc ccc gtt tta gat tat atc    1946
Leu Leu Leu Leu Ser Ala Val Ile Phe Arg Pro Val Leu Asp Tyr Ile
          30                 35                 40 gag ggg agt tca cgt ttc cat gaa att gaa aat gag tta gcg gtg aaa    1994
Glu Gly Ser Ser Arg Phe His Glu Ile Glu Asn Glu Leu Ala Val Lys
     45                 50                 55 cgt tca gaa ttg ttg cat caa cag aaa att tta act tct tta cag cag    2042
Arg Ser Glu Leu Leu His Gln Gln Lys Ile Leu Thr Ser Leu Gln Gln
60                 65                 70                 75 cag tcg gaa agt cga aaa ctt tct cca gaa ctg gct gca caa att att    2090
Gln Ser Glu Ser Arg Lys Leu Ser Pro Glu Leu Ala Ala Gln Ile Ile
                   80                 85                 90 cct ttg aat aaa caa att caa cgt tta gct gcg cgt aac ggt tta tct    2138
Pro Leu Asn Lys Gln Ile Gln Arg Leu Ala Ala Arg Asn Gly Leu Ser
          95                 100               105 cag cat tta cgt tgg gaa atg ggg caa aag cct att ttg cat tta cag    2186
Gln His Leu Arg Trp Glu Met Gly Gln Lys Pro Ile Leu His Leu Gln
              110               115               120 ctt aca ggt cat ttt gag aaa acg aag aca ttt tta acc gca ctt ttg    2234
Leu Thr Gly His Phe Glu Lys Thr Lys Thr Phe Leu Thr Ala Leu Leu
     125               130               135 gct aat tcg tca cag ctt tca gtg agt cgc ttg cag ttt atc aaa ccc    2282
Ala Asn Ser Ser Gln Leu Ser Val Ser Arg Leu Gln Phe Ile Lys Pro
140             145               150               155 gaa gac aac cca ttg caa acc gag atc att ttt cag cta gat aag gaa    2330
Glu Asp Asn Pro Leu Gln Thr Glu Ile Ile Phe Gln Leu Asp Lys Glu
                 160               165               170 aca aaa tga aacattggtt tttcctgatt atattatttt ttatgaattg    2379
Thr Lys cagttgggga caagatcctt tcgataaaac acagcgtaac cgttctcagt ttgataacgc    2439
acaaacagta atggagcaga cagaaataat ttcctcagat gtacctaata atctatgcgg    2499

```
agcggatgaa aatcgccaag cggctgaaat tcctttgaac gctttaaaat tggtgggcgt    2559
agtgatttct aaagataaag cctttgcctt gttgcaagat caaggtttgc aaatttacag    2619
cgttttagag ggcgttgatg tggctcaaga gggctatatt gtagaaaaaa tcaaccaaaa    2679
caatgttcaa tttatgcgta agctcggaga gcaatgtgat agtagtgaat ggaaaaaatt    2739
aagttttttaa aggaagatta tgaagaaata tttttttaaag tgcggttatt ttttagtgtg    2799
tttttgtttg ccattaatcg ttttgctaa tcctaaaaca gataacgaat gttttttat       2859
tcgtttatcg caagcacctt tagctcaaac actggagcaa ttagcttttc aacaagatgt    2919
gaatttagtg atgggtgaga ggttagaagg caatatttct ttgaaattaa acaatattga    2979
tatgccacgt ttgctaaaaa taatcgcaaa aagtaagcat cttactttga ataaagatga    3039
tggggtttat tatttaaacg gcagtcaatc tggcaaaggt caagttgcag gaaatcttac    3099
gacaaatgaa ccgcacttag tcagccacac ggtaaaactt cattttgcta aagcctctga    3159
attaatgaaa tccttaacaa caggaagtgg atctttgctt tcttctgcgg ggagcattac    3219
ctttgatgat cgcagtaatt tgctggttat tcaggatgaa cctcgttttg tgcaaaatat    3279
caaaaaactg attgctgaaa tggataagcc tattgaacag atcgctattg aagcgcgaat    3339
tgtgacaatt acggatgaga gtttgaaaga acttggcgtt cggtggggga ttttttaatcc  3399
aactgaaaat gcaagacgag ttgcgggcag ccttacaggc aatagctttg aaaatattgc    3459
ggataatctt aatgtaaatt tgcgacaac gacgacacct gctggctcta tagcattaca     3519
agtcgcgaaa attaatgggc gattgcttga tttagaattg agtgcgttgg agcgtgaaaa    3579
taatgtagaa attattgcaa gtcctcgctt actcactacc aataagaaaa gtgcgagcat    3639
taaacagggg acagaaattc cttacatcgt gagtaatact cgtaacgata cgcaatctgt    3699
ggaatttcgt gaggcagtac ttggtttgga agtgacgcca catatttcta aagataacaa    3759
tatcttactt gatttattgg taagtcaaaa ttccccctggt tctcgtgtcg cttatggaca   3819
aaatgaggtg gtttctattg ataagcaaga aattaatact caggtttttg ccaaagatgg    3879
ggaaaccatt gtgcttggcg gcgtatttca cgacacaatc acgaaaagcg aagataaagt    3939
gccattgctt ggcgatatac ccgttattaa acgattattt agcaaagaaa gtgaacgaca    3999
tcaaaaacgt gagctcgtga ttttcgtcac gccgcatatt ttaaaagcag agaaacgtt     4059
agaggcgttg aaacaaaaaa gtgcggggaa aaaataactt ttttagacga tgaattttt    4119
taattttcgc tgtatccact gtcgtggcaa tcttcatatt gcaaaaaatg ggctatgttc   4179
aggttgccaa aaacaaatta aatctttttcc ttattgcggt cattgtggtg cggaattgca   4239
atattatgcg cagcattgtg gtaattgtct taaacaagaa ccaagttggg ataagatggt    4299
cattattggg cattatattg aacctctttc gatattgatt caccgtttta aatttcaaaa    4359
tcaattttgg attgaccgca ctttagctcg gcttttatat cttgcggtgc gtgatgctaa    4419
acgaacgcat caacttaaat tgccagaagc aatcattcca gtgcctttat atcatttcg    4479
tcagtggcga cggggttata atcaggcaga tttattatct cggcaattaa gtcgctggct    4539
ggatattcct aatttgagca atatcgtaaa gcgtgtgaaa cacacctata ctcaacgtgg    4599
tttgagtgca aaagatcgtc gtcagaattt aaaaaatgcc ttttctcttg ttgtttcgaa    4659
aaatgaattt ccttatcgcc gtgttgcgtt ggtggatgat gtgattacta ctggttctac    4719
actcaatgaa atctcaaaat tgttgcgaaa attaggtgtg gaggagattc aagtgtgggg    4779
gctggcacga gcttaatata aagcactgga aaaaaagcg cgataagcgt attattcccg     4839
atactttctc tcaagtattt aggac                                          4864
```

<210> SEQ ID NO 14
<211> LENGTH: 173
<212> TYPE: PRT
<213> ORGANISM: H. influenzae

<400> SEQUENCE: 14

```
Met Lys Ala Phe Phe Asn Asp Pro Phe Thr Pro Phe Gly Lys Trp Leu
1               5                   10                  15

Ser Gln Pro Phe Tyr Val His Gly Leu Thr Phe Leu Leu Leu Leu Ser
            20                  25                  30

Ala Val Ile Phe Arg Pro Val Leu Asp Tyr Ile Glu Gly Ser Ser Arg
        35                  40                  45

Phe His Glu Ile Glu Asn Glu Leu Ala Val Lys Arg Ser Glu Leu Leu
    50                  55                  60

His Gln Gln Lys Ile Leu Thr Ser Leu Gln Gln Ser Glu Ser Arg
65                  70                  75                  80

Lys Leu Ser Pro Glu Leu Ala Ala Gln Ile Ile Pro Leu Asn Lys Gln
                85                  90                  95

Ile Gln Arg Leu Ala Ala Arg Asn Gly Leu Ser Gln His Leu Arg Trp
            100                 105                 110

Glu Met Gly Gln Lys Pro Ile Leu His Leu Gln Leu Thr Gly His Phe
        115                 120                 125

Glu Lys Thr Lys Thr Phe Leu Thr Ala Leu Leu Ala Asn Ser Ser Gln
    130                 135                 140

Leu Ser Val Ser Arg Leu Gln Phe Ile Lys Pro Glu Asp Asn Pro Leu
145                 150                 155                 160

Gln Thr Glu Ile Ile Phe Gln Leu Asp Lys Glu Thr Lys
                165                 170
```

<210> SEQ ID NO 15
<211> LENGTH: 4864
<212> TYPE: DNA
<213> ORGANISM: H. influenzae
<220> FEATURE:
<221> NAME/KEY: CDS
<222> LOCATION: (2336)..(2749)

<400> SEQUENCE: 15

| | | |
|---|---|---|
| tacgaataat ggttttttct ggggttaaga aaaagttacg cgctaattgt tgagtaatcg | 60 |
| tacttgcacc ttgtgatgca ccgccattac tcactgcgac aaacaatgca cgagcaatgc | 120 |
| cgatagggtc taatccgtga tgatcgtaaa acgattgtc ttccgttgct aaaaatgcgt | 180 |
| caattaagcg ttgtggcaca tcggctaatt tcactggaat acggcgttgc tcgcccactt | 240 |
| cgccaattaa tttaccgtca gccgtataaa tctgcattgg ttgttgtaat tcaacggttc | 300 |
| ttaatgtttc tactgagggc aattccgatt ttaggtggaa atacaacatt ccgccagcca | 360 |
| ctaaacctaa aatacataaa gttaatagg tgtttaatat taattttgcg atccgcatcg | 420 |
| taaaattctc gcttggttaa tgaatattct tgtcaagaga cctatgattt agttgttaag | 480 |
| tataaaagat tcagcctta aagaatagga aagaatatgc aattctccct gaaaaattac | 540 |
| cgcactttac aaatcggcat tcatcgtaag cagggttatt ttgatttgt gtggtttgat | 600 |
| gatcttgaac agccacaaag ttatcaaatt tttgttaatg atcgtgattt taaaaatcgt | 660 |
| tttttacaac agctaaaaac acaatatcaa gggaaaacct tcctttaca gtttgtggca | 720 |
| agcattcccg ctcacttaac ttggtcgaaa gtattaatgt tgccacaagt gttaaatgcg | 780 |

```
caagaatgtc atcaacaatg taaatttgtg attgaaaaag agctgcctat ttctttaaat      840
gaattatggt ttgattatcg ttctacctcg ttaaagcaag gttttcgatt agacgttact      900
gcaattcgta aaagtactgc tcaaacttat ttgcaagatt ttcagccatt taaaattaat     960
gtattggatg ttgcgtcaaa tgctattttg cgtgcatttc agtatttgtt gaatgaacaa     1020
gtgcggtcag aaaataccct attttattt caagaagatg actattgttt ggcgatctgt      1080
gaaagatcgc agcaatcgca aatttttcaa tctcacgaaa atttgaccgc acttatgaa      1140
caatttaccg aacgttttga aggacaactt gaacaagttt tgtttatca aattccctca      1200
agtcatacac cattacccga aaactggcag cgagtagaaa cagaactccc ttttattgcg     1260
cttggcaacg cgctatggca aaaagattta catcaacaaa agtgggtgg ttaaatgtcg      1320
atgaatttat tgccttggcg tacttatcaa catcaaaagc gttacgtcg tttagctttt      1380
tatatcgctt tatttatctt gcttgctatt aatttaatgt ggcttttag caatttgatt      1440
gaacaacaga aacaaaattt gcaagcgcag caaacatctt ttgaacaact taatcagcaa     1500
cttcacaaaa ctaccatgca aattgatcag ttacgcagtg cggtgaaagt tggtgaagtt     1560
ttgacatcta ttcccaacga gcaagtaaaa aagagtttac aacagctaag tgaattacct     1620
tttcaacaag gagaactgaa taaatttaaa caagatgcca ataacttaag tttggaaggt     1680
aacgcgcaag atcaaacaga atttgaactg attcatcaat tttttaaagaa acattttccc   1740
aatgtgaaat taagtcaggt tcaacctgaa caagatacat tgtttttca ctttgatgtg     1800
gaacaagggg cggaaaaatg aaagcttttt ttaacgatcc tttactcct tttgaaaat    1860
ggctaagtca gccttttttat gtgcacggtt taacctttt attgctatta agtgcggtga  1920
tttttcgccc cgttttagat tatatcgagg ggagttcacg tttccatgaa attgaaaatg     1980
agttagcggt gaaacgttca gaattgttgc atcaacagaa aattttaact tctttacagc    2040
agcagtcgga aagtcgaaaa ctttctccag aactggctgc acaaattatt cctttgaata    2100
aacaaattca acgtttagct cgcgtaacg gtttatctca gcatttacgt tgggaaatgg     2160
ggcaaaagcc tattttgcat ttacagctta caggtcattt tgagaaaacg aagcattttt   2220
taaccgcact tttggctaat tcgtcacagc tttcagtgag tcgcttgcag tttatcaaac   2280
ccgaagacaa cccattgcaa accgagatca ttttcagct agataaggaa acaaa atg     2338
                                                                Met
                                                                  1
aaa cat tgg ttt ttc ctg att ata tta ttt ttt atg aat tgc agt tgg       2386
Lys His Trp Phe Phe Leu Ile Ile Leu Phe Phe Met Asn Cys Ser Trp
          5                  10                  15
gga caa gat cct ttc gat aaa aca cag cgt aac cgt tct cag ttt gat      2434
Gly Gln Asp Pro Phe Asp Lys Thr Gln Arg Asn Arg Ser Gln Phe Asp
         20                  25                  30
aac gca caa aca gta atg gag cag aca gaa ata att tcc tca gat gta      2482
Asn Ala Gln Thr Val Met Glu Gln Thr Glu Ile Ile Ser Ser Asp Val
         35                  40                  45
cct aat aat cta tgc gga gcg gat gaa aat cgc caa gcg gct gaa att      2530
Pro Asn Asn Leu Cys Gly Ala Asp Glu Asn Arg Gln Ala Ala Glu Ile
50                  55                  60                  65
cct ttg aac gct tta aaa ttg gtg ggc gta gtg att tct aaa gat aaa      2578
Pro Leu Asn Ala Leu Lys Leu Val Gly Val Val Ile Ser Lys Asp Lys
                 70                  75                  80
gcc ttt gcc ttg ttg caa gat caa ggt ttg caa att tac agc gtt tta      2626
Ala Phe Ala Leu Leu Gln Asp Gln Gly Leu Gln Ile Tyr Ser Val Leu
             85                  90                  95
gag ggc gtt gat gtg gct caa gag ggc tat att gta gaa aaa atc aac      2674
```

```
Glu Gly Val Asp Val Ala Gln Glu Gly Tyr Ile Val Glu Lys Ile Asn
        100                 105                 110 caa aac aat gtt caa ttt atg cgt aag ctc gga gag caa tgt gat agt    2722
Gln Asn Asn Val Gln Phe Met Arg Lys Leu Gly Glu Gln Cys Asp Ser
    115                 120                 125 agt gaa tgg aaa aaa tta agt ttt taa aggaagatta tgaagaaata           2769
Ser Glu Trp Lys Lys Leu Ser Phe
130                 135 tttttttaaag tgcggttatt ttttagtgtg tttttgtttg ccattaatcg ttttgctaa   2829 tcctaaaaca gataacgaat gttttttttat tcgtttatcg caagcacctt tagctcaaac  2889
actggagcaa ttagctttc aacaagatgt gaatttagtg atgggtgaga ggttagaagg    2949
caatatttct ttgaaattaa acaatattga tatgccacgt ttgctaaaaa taatcgcaaa   3009
aagtaagcat cttactttga ataaagatga tggggtttat tatttaaacg gcagtcaatc  3069
tggcaaaggt caagttgcag gaaatcttac gacaaatgaa ccgcacttag tcagccacac  3129
ggtaaaactt cattttgcta aagcctctga attaatgaaa tccttaacaa caggaagtgg  3189
atctttgctt tcttctgcgg ggagcattac ctttgatgat cgcagtaatt tgctggttat  3249
tcaggatgaa cctcgttttg tgcaaaatat caaaaaactg attgctgaaa tggataagcc  3309
tattgaacag atcgctattg aagcgcgaat tgtgacaatt acggatgaga gtttgaaaga  3369
acttggcgtt cggtggggga ttttaatcc aactgaaaat gcaagacgag ttgcgggcag   3429
ccttacaggc aatagctttg aaaatattgc ggataatctt aatgtaaatt ttgcgacaac  3489
gacgacacct gctggctcta tagcattaca agtcgcgaaa attaatgggc gattgcttga  3549
tttagaattg agtgcgttgg agcgtgaaaa taatgtagaa attattgcaa gtcctcgctt  3609
actcactacc aataagaaaa gtgcgagcat taaacagggg acagaaattc cttacatcgt  3669
gagtaatact cgtaacgata cgcaatctgt ggaatttcgt gaggcagtac ttggtttgga  3729
agtgacgcca catatttcta aagataacaa tatcttactt gatttattgg taagtcaaaa  3789
ttcccctggt tctcgtgtcg cttatggaca aaatgaggtg gtttctattg ataagcaaga  3849
aattaatact caggttttg ccaaagatgg ggaaaccatt gtgcttggcg gcgtatttca   3909
cgacacaatc acgaaaagcg aagataaagt gccattgctt ggcgatatac ccgttattaa  3969
acgattattg agcaaagaaa gtgaacgaca tcaaaaacgt gagctcgtga ttttcgtcac  4029
gccgcatatt ttaaaagcag gagaaacgtt agaggcgttg aaacaaaaaa gtgcggggaa  4089
aaaataactt ttttagacga tgaatttttt taatttttcgc tgtatccact gtcgtggcaa  4149
tcttcatatt gcaaaaaatg ggctatgttc aggttgccaa aaacaaatta aatctttttcc 4209 ttattgcggt cattgtggtg cggaattgca atattatgcg cagcattgtg gtaattgtct  4269
taaacaagaa ccaagttggg ataagatggt cattattggg cattatattg aacctctttc  4329
gatattgatt caccgttta aatttcaaaa tcaattttgg attgaccgca ctttagctcg   4389
gcttttatat cttgcggtgc gtgatgctaa acgaacgcat caacttaaat tgccagaagc  4449
aatcattcca gtgcctttat atcattttcg tcagtggcga cggggttata atcaggagca  4509
tttattatct cggcaattaa gtcgctggct ggatattcct aatttgagca atatcgtaaa  4569
gcgtgtgaaa cacacctata ctcaacgtgg tttgagtgca aaagatcgtc gtcagaattt  4629
aaaaaatgcc ttttctcttg ttgtttcgaa aaatgaattt ccttatcgcc gtgttgcgtt  4689
ggtggatgat gtgattacta ctggttctac actcaatgaa atctcaaaat tgttgcgaaa  4749
attaggtgtg gaggagattc aagtgtgggg gctggcacga gcttaatata aagcactgga  4809
```
aaaaaaagcg cgataagcgt attattcccg atactttctc tcaagtattt aggac    4864

<210> SEQ ID NO 16
<211> LENGTH: 137
<212> TYPE: PRT
<213> ORGANISM: H. influenzae

<400> SEQUENCE: 16

Met Lys His Trp Phe Phe Leu Ile Ile Leu Phe Phe Met Asn Cys Ser
1               5                   10                  15

Trp Gly Gln Asp Pro Phe Asp Lys Thr Gln Arg Asn Arg Ser Gln Phe
            20                  25                  30

Asp Asn Ala Gln Thr Val Met Glu Gln Thr Glu Ile Ile Ser Ser Asp
        35                  40                  45

Val Pro Asn Asn Leu Cys Gly Ala Asp Glu Asn Arg Gln Ala Ala Glu
    50                  55                  60

Ile Pro Leu Asn Ala Leu Lys Leu Val Gly Val Ile Ser Lys Asp
65                  70                  75                  80

Lys Ala Phe Ala Leu Leu Gln Asp Gln Gly Leu Gln Ile Tyr Ser Val
                85                  90                  95

Leu Glu Gly Val Asp Val Ala Gln Glu Gly Tyr Ile Val Glu Lys Ile
            100                 105                 110

Asn Gln Asn Asn Val Gln Phe Met Arg Lys Leu Gly Glu Gln Cys Asp
        115                 120                 125

Ser Ser Glu Trp Lys Lys Leu Ser Phe
    130                 135

<210> SEQ ID NO 17
<211> LENGTH: 4864
<212> TYPE: DNA
<213> ORGANISM: H. influenzae
<220> FEATURE:
<221> NAME/KEY: CDS
<222> LOCATION: (2759)..(4096)

<400> SEQUENCE: 17
tacgaataat ggttttttct ggggttaaga aaaagttacg cgctaattgt tgagtaatcg     60
tacttgcacc ttgtgatgca ccgccattac tcactgcgac aaacaatgca cgagcaatgc    120
cgatagggtc taatccgtga tgatcgtaaa acgattgtc ttccgttgct aaaaatgcgt     180
caattaagcg ttgtggcaca tcggctaatt tcactggaat acggcgttgc tcgcccactt    240
cgccaattaa tttaccgtca gccgtataaa tctgcattgg ttgttgtaat tcaacggttc    300
ttaatgtttc tactgagggc aattccgatt ttaggtggaa atacaacatt ccgccagcca    360
ctaaacctaa aatacataaa gttaataggg tgtttaatat taattttgcg atccgcatcg    420
taaaattctc gcttggttaa tgaatattct tgtcaagaga cctatgattt agttgttaag    480
tataaaagat tcagccttta aagaatagga agaatatgaa attctccct gaaaaattac     540 cgcactttac aaatcggcat tcatcgtaag cagggttatt ttgattttgt gtggtttgat    600
gatcttgaac agccacaaag ttatcaaatt tttgttaatg atcgtgattt taaaaatcgt    660 ttttttacaac agctaaaaac acaatatcaa gggaaaacct ttcctttaca gtttgtggca    720
agcattcccg ctcacttaac ttggtcgaaa gtattaatgt tgccacaagt gttaaatgcg    780
caagaatgtc atcaacaatg taaatttgtg attgaaaaag agctgcctat ttctttaaat    840
gaattatggt tgattatcg ttctacctcg ttaaagcaag gttttcgatt agacgttact     900
gcaattcgta aaagtactgc tcaaacttat ttgcaagatt ttcagccatt taaaattaat    960

-continued

```
gtattggatg ttgcgtcaaa tgctatttg cgtgcatttc agtatttgtt gaatgaacaa      1020
gtgcggtcag aaaataccct attttattt caagaagatg actattgttt ggcgatctgt      1080
gaaagatcgc agcaatcgca aattttacaa tctcacgaaa atttgaccgc actttatgaa      1140
caatttaccg aacgttttga aggacaactt gaacaagttt ttgtttatca aattccctca     1200
agtcatacac cattacccga aaactggcag cgagtagaaa cagaactccc ttttattgcg     1260
cttggcaacg cgctatggca aaaagattta catcaacaaa aagtgggtgg ttaaatgtcg     1320
atgaatttat tgccttggcg tactatcaa catcaaaagc gttacgtcg tttagcttt       1380
tatatcgctt tatttatctt gcttgctatt aatttaatgt tggcttttag caatttgatt    1440
gaacaacaga aacaaaattt gcaagcgcag caaacatctt ttgaacaact taatcagcaa    1500
cttcacaaaa ctaccatgca aattgatcag ttacgcagtg cggtgaaagt tggtgaagtt    1560
ttgcatccta ttcccaacga gcaagtaaaa aagagtttac aacagctaag tgaattacct    1620
tttcaacaag gagaactgaa taaattaaa caagatgcca ataacttaag tttggaaggt     1680
aacgcgcaag atcaaacaga atttgaactg attcatcaat ttttaaagaa acattttccc    1740
aatgtgaaat taagtcaggt tcaacctgaa caagatacat tgtttttca ctttgatgtg     1800
gaacaagggg cggaaaaatg aaagctttt ttaacgatcc ttttactcct tttggaaaat    1860
ggctaagtca gccttttat gtgcacggtt taaccttttt attgctatta agtgcggtga    1920
tttttcgccc cgttagat tatatcgagg ggagttcacg tttccatgaa attgaaatg       1980
agttagcggt gaaacgttca gaattgttgc atcaacagaa aatttaact tctttacagc    2040
agcagtcgga aagtcgaaaa ctttctccag aactggctgc acaaattatt cctttgaata   2100
aacaaattca acgtttagct gcgcgtaacg gtttatctca gcatttacgt tgggaaatgg    2160
ggcaaaagcc tattttgcat ttacagctta caggtcattt tgagaaaacg aagacatttt   2220
taaccgcact tttggctaat tcgtcacagc tttcagtgag tcgcttgcag tttatcaaac    2280
ccgaagacaa cccattgcaa accgagatca ttttcagct agataaggaa acaaaatgaa    2340
acattggttt ttcctgatta tattatttt tatgaattgc agttggggac aagatccttt    2400
cgataaaaca cagcgtaacc gttctcagtt tgataacgca caaacagtaa tggagcagac    2460
agaaataatt tcctcagatg tacctaataa tctatgcgga gcggatgaaa atcgccaagc    2520
ggctgaaatt cctttgaacg ctttaaaatt ggtgggcgta gtgatttcta aagataaagc    2580
ctttgccttg ttgcaagatc aaggtttgca aatttacagc gttttagagg gcgttgatgt    2640
ggctcaagag ggctatattg tagaaaaaat caaccaaaac aatgttcaat ttatgcgtaa    2700
gctcggagag caatgtgata gtagtgaatg gaaaaaatta agttttttaaa ggaagatt    2758
```

| | | | | | | | | | | | | | | | | |
|---|---|---|---|---|---|---|---|---|---|---|---|---|---|---|---|---|
| atg | aag | aaa | tat | ttt | tta | aag | tgc | ggt | tat | ttt | tta | gtg | tgt | ttt | tgt | 2806 |
| Met | Lys | Lys | Tyr | Phe | Leu | Lys | Cys | Gly | Tyr | Phe | Leu | Val | Cys | Phe | Cys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | cca | tta | atc | gtt | ttt | gct | aat | cct | aaa | aca | gat | aac | gaa | tgt | ttt | 2854 |
| Leu | Pro | Leu | Ile | Val | Phe | Ala | Asn | Pro | Lys | Thr | Asp | Asn | Glu | Cys | Phe | |
| | | | | 20 | | | | | 25 | | | | | 30 | | |

| | | | | | | | | | | | | | | | | |
|---|---|---|---|---|---|---|---|---|---|---|---|---|---|---|---|---|
| ttt | att | cgt | tta | tcg | caa | gca | cct | tta | gct | caa | aca | ctg | gag | caa | tta | 2902 |
| Phe | Ile | Arg | Leu | Ser | Gln | Ala | Pro | Leu | Ala | Gln | Thr | Leu | Glu | Gln | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| gct | ttt | caa | caa | gat | gtg | aat | tta | gtg | atg | ggt | gag | agg | tta | gaa | ggc | 2950 |
| Ala | Phe | Gln | Gln | Asp | Val | Asn | Leu | Val | Met | Gly | Glu | Arg | Leu | Glu | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| aat | att | tct | ttg | aaa | tta | aac | aat | att | gat | atg | cca | cgt | ttg | cta | aaa | 2998 |
| Asn | Ile | Ser | Leu | Lys | Leu | Asn | Asn | Ile | Asp | Met | Pro | Arg | Leu | Leu | Lys | |

```
                65                  70                  75                  80
ata atc gca aaa agt aag cat ctt act ttg aat aaa gat gat ggg gtt          3046
Ile Ile Ala Lys Ser Lys His Leu Thr Leu Asn Lys Asp Asp Gly Val
                85                  90                  95 tat tat tta aac ggc agt caa tct ggc aaa ggt caa gtt gca gga aat          3094
Tyr Tyr Leu Asn Gly Ser Gln Ser Gly Lys Gly Gln Val Ala Gly Asn
            100                 105                 110 ctt acg aca aat gaa ccg cac tta gtc agc cac acg gta aaa ctt cat          3142
Leu Thr Thr Asn Glu Pro His Leu Val Ser His Thr Val Lys Leu His
            115                 120                 125 ttt gct aaa gcc tct gaa tta atg aaa tcc tta aca aca gga agt gga          3190
Phe Ala Lys Ala Ser Glu Leu Met Lys Ser Leu Thr Thr Gly Ser Gly
        130                 135                 140 tct ttg ctt tct tct gcg ggg agc att acc ttt gat gat cgc agt aat          3238
Ser Leu Leu Ser Ser Ala Gly Ser Ile Thr Phe Asp Asp Arg Ser Asn
145                 150                 155                 160 ttg ctg gtt att cag gat gaa cct cgt ttt gtg caa aat atc aaa aaa          3286
Leu Leu Val Ile Gln Asp Glu Pro Arg Phe Val Gln Asn Ile Lys Lys
                165                 170                 175 ctg att gct gaa atg gat aag cct att gaa cag atc gct att gaa gcg          3334
Leu Ile Ala Glu Met Asp Lys Pro Ile Glu Gln Ile Ala Ile Glu Ala
            180                 185                 190 cga att gtg aca att acg gat gag agt ttg aaa gaa ctt ggc gtt cgg          3382
Arg Ile Val Thr Ile Thr Asp Glu Ser Leu Lys Glu Leu Gly Val Arg
            195                 200                 205 tgg ggg att ttt aat cca act gaa aat gca aga cga gtt gcg ggc agc          3430
Trp Gly Ile Phe Asn Pro Thr Glu Asn Ala Arg Arg Val Ala Gly Ser
        210                 215                 220 ctt aca ggc aat agc ttt gaa aat att gcg gat aat ctt aat gta aat          3478
Leu Thr Gly Asn Ser Phe Glu Asn Ile Ala Asp Asn Leu Asn Val Asn
225                 230                 235                 240 ttt gcg aca acg acg aca cct gct ggc tct ata gca tta caa gtc gcg          3526
Phe Ala Thr Thr Thr Thr Pro Ala Gly Ser Ile Ala Leu Gln Val Ala
                245                 250                 255 aaa att aat ggg cga ttg ctt gat tta gaa ttg agt gcg ttg gag cgt          3574
Lys Ile Asn Gly Arg Leu Leu Asp Leu Glu Leu Ser Ala Leu Glu Arg
            260                 265                 270 gaa aat aat gta gaa att att gca agt cct cgc tta ctc act acc aat          3622
Glu Asn Asn Val Glu Ile Ile Ala Ser Pro Arg Leu Leu Thr Thr Asn
            275                 280                 285 aag aaa agt gcg agc att aaa cag ggg aca gaa att cct tac atc gtg          3670
Lys Lys Ser Ala Ser Ile Lys Gln Gly Thr Glu Ile Pro Tyr Ile Val
        290                 295                 300 agt aat act cgt aac gat acg caa tct gtg gaa ttt cgt gag gca gta          3718
Ser Asn Thr Arg Asn Asp Thr Gln Ser Val Glu Phe Arg Glu Ala Val
305                 310                 315                 320 ctt ggt ttg gaa gtg acg cca cat att tct aaa gat aac aat atc tta          3766
Leu Gly Leu Glu Val Thr Pro His Ile Ser Lys Asp Asn Asn Ile Leu
                325                 330                 335 ctt gat tta ttg gta agt caa aat tcc cct ggt tct cgt gtc gct tat          3814
Leu Asp Leu Leu Val Ser Gln Asn Ser Pro Gly Ser Arg Val Ala Tyr
            340                 345                 350 gga caa aat gag gtg gtt tct att gat aag caa gaa att aat act cag          3862
Gly Gln Asn Glu Val Val Ser Ile Asp Lys Gln Glu Ile Asn Thr Gln
            355                 360                 365 gtt ttt gcc aaa gat ggg gaa acc att gtg ctt ggc ggc gta ttt cac          3910
Val Phe Ala Lys Asp Gly Glu Thr Ile Val Leu Gly Gly Val Phe His
        370                 375                 380 gac aca atc acg aaa agc gaa gat aaa gtg cca ttg ctt ggc gat ata          3958
```

```
Asp Thr Ile Thr Lys Ser Glu Asp Lys Val Pro Leu Leu Gly Asp Ile
385                 390                 395                 400 ccc gtt att aaa cga tta ttt agc aaa gaa agt gaa cga cat caa aaa      4006
Pro Val Ile Lys Arg Leu Phe Ser Lys Glu Ser Glu Arg His Gln Lys
                405                 410                 415 cgt gag ctc gtg att ttc gtc acg ccg cat att tta aaa gca gga gaa      4054
Arg Glu Leu Val Ile Phe Val Thr Pro His Ile Leu Lys Ala Gly Glu
            420                 425                 430 acg tta gag gcg ttg aaa caa aaa agt gcg ggg aaa aaa taa              4096
Thr Leu Glu Ala Leu Lys Gln Lys Ser Ala Gly Lys Lys
        435                 440                 445 cttttttaga cgatgaattt ttttaatttt cgctgtatcc actgtcgtgg caatcttcat    4156
attgcaaaaa atgggctatg ttcaggttgc caaaaacaaa ttaaatcttt tccttattgc    4216
ggtcattgtg gtgcggaatt gcaatattat gcgcagcatt gtggtaattg tcttaaacaa    4276
gaaccaagtt gggataagat ggtcattatt gggcattata ttgaacctct ttcgatattg    4336
attcaccgtt ttaaatttca aaatcaattt tggattgacc gcactttagc tcggctttta    4396
tatcttgcgg tgcgtgatgc taaacgaacg catcaactta aattgccaga agcaatcatt    4456
ccagtgcctt tatatcattt tcgtcagtgg cgacggggtt ataatcaggc agatttatta    4516
tctcggcaat taagtcgctg gctggatatt cctaatttga gcaatatcgt aaagcgtgtg    4576
aaacacacct atactcaacg tggtttgagt gcaaagatc gtcgtcagaa tttaaaaaat     4636
gcctttctc ttgttgtttc gaaaaatgaa tttccttatc gccgtgttgc gttggtggat     4696
gatgtgatta ctactggttc tacactcaat gaaatctcaa aattgttgcg aaaattaggt    4756
gtggaggaga ttcaagtgtg ggggctggca cgagcttaat ataaagcact ggaaaaaaaa    4816
gcgcgataag cgtattattc ccgatacttt ctctcaagta tttaggac                 4864
```

<210> SEQ ID NO 18
<211> LENGTH: 445
<212> TYPE: PRT
<213> ORGANISM: H. influenzae

<400> SEQUENCE: 18

```
Met Lys Lys Tyr Phe Leu Lys Cys Gly Tyr Phe Leu Val Cys Phe Cys
1               5                   10                  15

Leu Pro Leu Ile Val Phe Ala Asn Pro Lys Thr Asp Asn Glu Cys Phe
            20                  25                  30

Phe Ile Arg Leu Ser Gln Ala Pro Leu Ala Gln Thr Leu Glu Gln Leu
        35                  40                  45

Ala Phe Gln Gln Asp Val Asn Leu Val Met Gly Glu Arg Leu Glu Gly
    50                  55                  60

Asn Ile Ser Leu Lys Leu Asn Asn Ile Asp Met Pro Arg Leu Leu Lys
65                  70                  75                  80

Ile Ile Ala Lys Ser Lys His Leu Thr Leu Asn Lys Asp Asp Gly Val
                85                  90                  95

Tyr Tyr Leu Asn Gly Ser Gln Ser Gly Lys Gly Gln Val Ala Gly Asn
            100                 105                 110

Leu Thr Thr Asn Glu Pro His Leu Val Ser His Thr Val Lys Leu His
        115                 120                 125

Phe Ala Lys Ala Ser Glu Leu Met Lys Ser Leu Thr Thr Gly Ser Gly
    130                 135                 140

Ser Leu Leu Ser Ser Ala Gly Ser Ile Thr Phe Asp Asp Arg Ser Asn
145                 150                 155                 160
```

```
Leu Leu Val Ile Gln Asp Glu Pro Arg Phe Val Gln Asn Ile Lys Lys
                165                 170                 175

Leu Ile Ala Glu Met Asp Lys Pro Ile Glu Gln Ile Ala Ile Glu Ala
            180                 185                 190

Arg Ile Val Thr Ile Thr Asp Glu Ser Leu Lys Glu Leu Gly Val Arg
        195                 200                 205

Trp Gly Ile Phe Asn Pro Thr Glu Asn Ala Arg Arg Val Ala Gly Ser
    210                 215                 220

Leu Thr Gly Asn Ser Phe Glu Asn Ile Ala Asp Asn Leu Asn Val Asn
225                 230                 235                 240

Phe Ala Thr Thr Thr Thr Pro Ala Gly Ser Ile Ala Leu Gln Val Ala
                245                 250                 255

Lys Ile Asn Gly Arg Leu Leu Asp Leu Glu Leu Ser Ala Leu Glu Arg
            260                 265                 270

Glu Asn Asn Val Glu Ile Ile Ala Ser Pro Arg Leu Leu Thr Thr Asn
        275                 280                 285

Lys Lys Ser Ala Ser Ile Lys Gln Gly Thr Glu Ile Pro Tyr Ile Val
    290                 295                 300

Ser Asn Thr Arg Asn Asp Thr Gln Ser Val Glu Phe Arg Glu Ala Val
305                 310                 315                 320

Leu Gly Leu Glu Val Thr Pro His Ile Ser Lys Asp Asn Asn Ile Leu
                325                 330                 335

Leu Asp Leu Leu Val Ser Gln Asn Ser Pro Gly Ser Arg Val Ala Tyr
            340                 345                 350

Gly Gln Asn Glu Val Val Ser Ile Asp Lys Gln Glu Ile Asn Thr Gln
        355                 360                 365

Val Phe Ala Lys Asp Gly Glu Thr Ile Val Leu Gly Gly Val Phe His
    370                 375                 380

Asp Thr Ile Thr Lys Ser Glu Asp Lys Val Pro Leu Leu Gly Asp Ile
385                 390                 395                 400

Pro Val Ile Lys Arg Leu Phe Ser Lys Glu Ser Glu Arg His Gln Lys
                405                 410                 415

Arg Glu Leu Val Ile Phe Val Thr Pro His Ile Leu Lys Ala Gly Glu
            420                 425                 430

Thr Leu Glu Ala Leu Lys Gln Lys Ser Ala Gly Lys Lys
        435                 440                 445

<210> SEQ ID NO 19
<211> LENGTH: 4864
<212> TYPE: DNA
<213> ORGANISM: H. influenzae
<220> FEATURE:
<221> NAME/KEY: CDS
<222> LOCATION: (4109)..(4795)

<400> SEQUENCE: 19
tacgaataat ggttttttct ggggttaaga aaaagttacg cgctaattgt tgagtaatcg      60
tacttgcacc ttgtgatgca ccgccattac tcactgcgac aaacaatgca cgagcaatgc     120
cgatagggtc taatccgtga tgatcgtaaa acgattgtc ttccgttgct aaaaatgcgt      180
caattaagcg ttgtggcaca tcggctaatt tcactggaat acggcgttgc tcgcccactt     240
cgccaattaa tttaccgtca gccgtataaa tctgcattgg ttgttgtaat tcaacggttc     300
ttaatgtttc tactgagggc aattccgatt ttaggtggaa atacaacatt ccgccagcca     360
ctaaacctaa aatacataaa gttaataggg tgtttaatat taattttgcg atccgcatcg     420
```

```
taaaattctc gcttggttaa tgaatattct tgtcaagaga cctatgattt agttgttaag    480
tataaaagat tcagccttta aagaatagga aagaatatgc aattctccct gaaaaattac    540
cgcactttac aaatcggcat tcatcgtaag cagggttatt ttgattttgt gtggtttgat    600
gatcttgaac agccacaaag ttatcaaatt tttgttaatg atcgtgattt taaaaatcgt    660
tttttacaac agctaaaaac acaatatcaa gggaaaacct ttcctttaca gtttgtggca    720
agcattcccg ctcacttaac ttggtcgaaa gtattaatgt tgccacaagt gttaaatgcg    780
caagaatgtc atcaacaatg taaatttgtg attgaaaaag agctgcctat ttctttaaat    840
gaattatggt ttgattatcg ttctacctcg ttaaagcaag gttttcgatt agacgttact    900
gcaattcgta aaagtactgc tcaaacttat ttgcaagatt ttcagccatt taaaattaat    960
gtattggatg ttgcgtcaaa tgctattttg cgtgcatttc agtatttgtt gaatgaacaa   1020
gtgcggtcag aaaatacctt atttttattt caagaagatg actattgttt ggcgatctgt   1080
gaaagatcgc agcaatcgca aattttacaa tctcacgaaa atttgaccgc actttatgaa   1140
caatttaccg aacgttttga aggacaactt gaacaagttt tgtttatca aattccctca   1200 agtcatacac cattacccga aaactggcag cgagtagaaa cagaactccc ttttattgcg   1260
cttggcaacg cgctatggca aaaagattta catcaacaaa aagtgggtgg ttaaatgtcg   1320
atgaatttat tgccttggcg tacttatcaa catcaaaagc gtttacgtcg tttagctttt   1380
tatatcgctt tatttatctt gcttgctatt aatttaatgt tggcttttag caatttgatt   1440
gaacaacaga acaaaatttt gcaagcgcag caaacatctt ttgaacaact taatcagcaa   1500
cttcacaaaa ctaccatgca aattgatcag ttacgcagtg cggtgaaagt tggtgaagtt   1560
ttgacatcta ttcccaacga gcaagtaaaa aagagtttac aacagctaag tgaattacct   1620
tttcaacaag gagaactgaa taaatttaaa caagatgcca ataacttaag tttggaaggt   1680
aacgcgcaag atcaaacaga atttgaactg attcatcaat ttttaaagaa acattttccc   1740
aatgtgaaat taagtcaggt tcaacctgaa caagatacat tgttttttca ctttgatgtg   1800
gaacaagggg cggaaaaatg aaagcttttt ttaacgatcc ttttactcct tttggaaaat   1860
ggctaagtca gccttttttat gtgcacggtt taacctttttt attgctatta agtgcggtga   1920
tttttcgccc cgttttagat tatatcgagg ggagttcacg tttccatgaa attgaaaatg   1980
agttagcggt gaaacgttca gaattgttgc atcaacagaa aattttaact tctttacagc   2040
agcagtcgga aagtcgaaaa ctttctccag aactggctgc acaaattatt cctttgaata   2100
aacaaattca acgtttagct gcgcgtaacg gtttatctca gcatttacgt tgggaaatgg   2160
ggcaaaagcc tattttgcat ttacagctta caggtcattt tgagaaaacg aagcattttt   2220
taaccgcact tttggctaat tcgtcacagc tttcagtgag tcgcttgcag tttatcaaac   2280
ccgaagacaa cccattgcaa accgagatca ttttcagct agataaggaa acaaaatgaa   2340
acattggttt ttcctgatta tattatttt tatgaattgc agtggggac aagatccttt   2400 cgataaaaca cagcgtaacc gttctcagtt tgataacgca caaacagtaa tggagcagac   2460
agaaataatt tcctcagatg tacctaataa tctatgcgga gcggatgaaa atcgccaagc   2520
ggctgaaatt cctttgaacg ctttaaaatt ggtgggcgta gtgatttcta aagataaagc   2580
ctttgccttg ttgcaagatc aaggtttgca aatttacagc gttttagagg gcgttgatgt   2640
ggctcaagag ggctatattg tagaaaaaat caaccaaaac aatgttcaat ttatgcgtaa   2700
gctcggagag caatgtgata gtagtgaatg gaaaaaatta gttttttaaa ggaagattat   2760
gaagaaatat ttttaaagt gcggttattt ttagtgtgt ttttgtttgc cattaatcgt   2820
```

```
ttttgctaat cctaaaacag ataacgaatg ttttttttatt cgtttatcgc aagcaccttt    2880
agctcaaaca ctggagcaat tagctttttca acaagatgtg aatttagtga tgggtgagag    2940
gttagaaggc aatatttctt tgaaattaaa caatattgat atgccacgtt tgctaaaaat    3000
aatcgcaaaa agtaagcatc ttactttgaa taaagatgat ggggtttatt atttaaacgg    3060
cagtcaatct ggcaaaggtc aagttgcagg aaatcttacg acaaatgaac cgcacttagt    3120
cagccacacg gtaaaacttc attttgctaa agcctctgaa ttaatgaaat ccttaacaac    3180
aggaagtgga tctttgcttt cttctgcggg gagcattacc tttgatgatc gcagtaattt    3240
gctggttatt caggatgaac ctcgttttgt gcaaaatatc aaaaaactga ttgctgaaat    3300
ggataagcct attgaacaga tcgctattga agcgcgaatt gtgacaatta cggatgagag    3360
tttgaaagaa cttggcgttc ggtggggat ttttaatcca actgaaaatg caagacgagt    3420
tgcgggcagc cttacaggca atagctttga aaatattgcg gataatctta atgtaaattt    3480
tgcgacaacg acgacacctg ctggctctat agcattacaa gtcgcgaaaa ttaatgggcg    3540
attgcttgat ttagaattga gtgcgttgga gcgtgaaaat aatgtagaaa ttattgcaag    3600
tcctcgctta ctcactacca ataagaaaag tgcgagcatt aaacagggga cagaaattcc    3660
ttacatcgtg agtaatactc gtaacgatac gcaatctgtg gaatttcgtg aggcagtact    3720
tggtttggaa gtgacgccac atatttctaa agataacaat atcttacttg atttattggt    3780
aagtcaaaat tcccctggtt ctcgtgtcgc ttatggacaa aatgaggtgg tttctattga    3840
taagcaagaa attaatactc aggtttttgc caaagatggg gaaaccattg tgcttggcgg    3900
cgtatttcac gacacaatca cgaaaagcga agataaagtg ccattgcttg gcgatatacc    3960
cgttattaaa cgattattta gcaaagaaag tgaacgacat caaaaacgtg agctcgtgat    4020
tttcgtcacg ccgcatattt taaaagcagg agaaacgtta gaggcgttga aacaaaaaag    4080
tgcggggaaa aaataacttt tttagacg atg aat ttt ttt aat ttt cgc tgt         4132
                              Met Asn Phe Phe Asn Phe Arg Cys
                               1               5 atc cac tgt cgt ggc aat ctt cat att gca aaa aat ggg cta tgt tca        4180
Ile His Cys Arg Gly Asn Leu His Ile Ala Lys Asn Gly Leu Cys Ser
 10              15                  20 ggt tgc caa aaa caa att aaa tct ttt cct tat tgc ggt cat tgt ggt        4228
Gly Cys Gln Lys Gln Ile Lys Ser Phe Pro Tyr Cys Gly His Cys Gly
 25              30                  35                  40 gcg gaa ttg caa tat tat gcg cag cat tgt ggt aat tgt ctt aaa caa        4276
Ala Glu Leu Gln Tyr Tyr Ala Gln His Cys Gly Asn Cys Leu Lys Gln
             45                  50                  55 gaa cca agt tgg gat aag atg gtc att att ggg cat tat att gaa cct        4324
Glu Pro Ser Trp Asp Lys Met Val Ile Ile Gly His Tyr Ile Glu Pro
 60                  65                  70 ctt tcg ata ttg att cac cgt ttt aaa ttt caa aat caa ttt tgg att        4372
Leu Ser Ile Leu Ile His Arg Phe Lys Phe Gln Asn Gln Phe Trp Ile
 75                  80                  85 gac cgc act tta gct cgg ctt tta tat ctt gcg gtg cgt gat gct aaa        4420
Asp Arg Thr Leu Ala Arg Leu Leu Tyr Leu Ala Val Arg Asp Ala Lys
 90                  95                 100 cga acg cat caa ctt aaa ttg cca gaa gca atc att cca gtg cct tta        4468
Arg Thr His Gln Leu Lys Leu Pro Glu Ala Ile Ile Pro Val Pro Leu
105                 110                 115                 120 tat cat ttt cgt cag tgg cga cgg ggt tat aat cag gca gat tta tta        4516
Tyr His Phe Arg Gln Trp Arg Arg Gly Tyr Asn Gln Ala Asp Leu Leu
                125                 130                 135
```

```
tct cgg caa tta agt cgc tgg ctg gat att cct aat ttg agc aat atc    4564
Ser Arg Gln Leu Ser Arg Trp Leu Asp Ile Pro Asn Leu Ser Asn Ile
        140                 145                 150 gta aag cgt gtg aaa cac acc tat act caa cgt ggt ttg agt gca aaa    4612
Val Lys Arg Val Lys His Thr Tyr Thr Gln Arg Gly Leu Ser Ala Lys
        155                 160                 165 gat cgt cgt cag aat tta aaa aat gcc ttt tct ctt gtt gtt tcg aaa    4660
Asp Arg Arg Gln Asn Leu Lys Asn Ala Phe Ser Leu Val Val Ser Lys
170                 175                 180 aat gaa ttt cct tat cgc cgt gtt gcg ttg gtg gat gat gtg att act    4708
Asn Glu Phe Pro Tyr Arg Arg Val Ala Leu Val Asp Asp Val Ile Thr
185                 190                 195                 200 act ggt tct aca ctc aat gaa atc tca aaa ttg ttg cga aaa tta ggt    4756
Thr Gly Ser Thr Leu Asn Glu Ile Ser Lys Leu Leu Arg Lys Leu Gly
            205                 210                 215 gtg gag gag att caa gtg tgg ggg ctg gca cga gct taa tataaagcac    4805
Val Glu Glu Ile Gln Val Trp Gly Leu Ala Arg Ala
        220                 225 tggaaaaaaa agcgcgataa gcgtattatt cccgatactt tctctcaagt atttaggac    4864

<210> SEQ ID NO 20
<211> LENGTH: 228
<212> TYPE: PRT
<213> ORGANISM: H. influenzae

<400> SEQUENCE: 20

Met Asn Phe Phe Asn Phe Arg Cys Ile His Cys Arg Gly Asn Leu His
1               5                   10                  15

Ile Ala Lys Asn Gly Leu Cys Ser Gly Cys Gln Lys Gln Ile Lys Ser
            20                  25                  30

Phe Pro Tyr Cys Gly His Cys Gly Ala Glu Leu Gln Tyr Tyr Ala Gln
        35                  40                  45

His Cys Gly Asn Cys Leu Lys Gln Glu Pro Ser Trp Asp Lys Met Val
    50                  55                  60

Ile Ile Gly His Tyr Ile Glu Pro Leu Ser Ile Leu Ile His Arg Phe
65                  70                  75                  80

Lys Phe Gln Asn Gln Phe Trp Ile Asp Arg Thr Leu Ala Arg Leu Leu
                85                  90                  95

Tyr Leu Ala Val Arg Asp Ala Lys Arg Thr His Gln Leu Lys Leu Pro
            100                 105                 110

Glu Ala Ile Ile Pro Val Pro Leu Tyr His Phe Arg Gln Trp Arg Arg
        115                 120                 125

Gly Tyr Asn Gln Ala Asp Leu Leu Ser Arg Gln Leu Ser Arg Trp Leu
    130                 135                 140

Asp Ile Pro Asn Leu Ser Asn Ile Val Lys Arg Val Lys His Thr Tyr
145                 150                 155                 160

Thr Gln Arg Gly Leu Ser Ala Lys Asp Arg Arg Gln Asn Leu Lys Asn
                165                 170                 175

Ala Phe Ser Leu Val Val Ser Lys Asn Glu Phe Pro Tyr Arg Arg Val
            180                 185                 190

Ala Leu Val Asp Asp Val Ile Thr Thr Gly Ser Thr Leu Asn Glu Ile
        195                 200                 205

Ser Lys Leu Leu Arg Lys Leu Gly Val Glu Glu Ile Gln Val Trp Gly
    210                 215                 220

Leu Ala Arg Ala
225
```

```
<210> SEQ ID NO 21
<211> LENGTH: 677
<212> TYPE: DNA
<213> ORGANISM: H. influenzae
<220> FEATURE:
<221> NAME/KEY: CDS
<222> LOCATION: (73)..(612)

<400> SEQUENCE: 21
tcacatgccc tatgttttca tacaaattaa agcatattaa atatttcgac tgcccctgtt      60
aaaaggagaa aa atg caa aca ata agt aaa caa cta agt gcg gtt att ttc     111
              Met Gln Thr Ile Ser Lys Gln Leu Ser Ala Val Ile Phe
              1               5                  10 cct ttc att ttt tct gcc tgc gtt tca caa tct gcg tct agc tta gat       159
Pro Phe Ile Phe Ser Ala Cys Val Ser Gln Ser Ala Ser Ser Leu Asp
        15                  20                  25 cat caa gct gcc gcc aaa gcg cga gtg gaa ctc gct ttg agc tat ctt       207
His Gln Ala Ala Ala Lys Ala Arg Val Glu Leu Ala Leu Ser Tyr Leu
30                  35                  40                  45 cag caa aat aat cct caa ctg gct aaa atc aat tta gac aaa gca ctt       255
Gln Gln Asn Asn Pro Gln Leu Ala Lys Ile Asn Leu Asp Lys Ala Leu
                50                  55                  60 caa cac gat aaa aat tac tat ctc gta cat tca gca ctt gca cat tat       303
Gln His Asp Lys Asn Tyr Tyr Leu Val His Ser Ala Leu Ala His Tyr
            65                  70                  75 tat caa caa caa ggg caa ata gaa aat gcc ttt cgt gag tat gaa ata       351
Tyr Gln Gln Gln Gly Gln Ile Glu Asn Ala Phe Arg Glu Tyr Glu Ile
        80                  85                  90 gcc gta aaa ctt aat cat aaa caa ggc gat gta cat aat aat ttt ggt       399
Ala Val Lys Leu Asn His Lys Gln Gly Asp Val His Asn Asn Phe Gly
    95                  100                 105 acg ttt cta tgt agt caa aag aaa ttt gag caa gcc cag caa caa ttt       447
Thr Phe Leu Cys Ser Gln Lys Lys Phe Glu Gln Ala Gln Gln Gln Phe
110                 115                 120                 125 gaa tta gcc ctt aat tcg ccg aat tat tat cat caa gca gat aca ttt       495
Glu Leu Ala Leu Asn Ser Pro Asn Tyr Tyr His Gln Ala Asp Thr Phe
                130                 135                 140 gaa aat atc gcg ctt tgt gct tat tcc gcg aaa aaa atg gat att tat       543
Glu Asn Ile Ala Leu Cys Ala Tyr Ser Ala Lys Lys Met Asp Ile Tyr
            145                 150                 155 cag caa aca tta gaa aaa tta cgt caa atc aat gga aaa cgt gcg gaa       591
Gln Gln Thr Leu Glu Lys Leu Arg Gln Ile Asn Gly Lys Arg Ala Glu
        160                 165                 170 aaa ttc aat agt cta aaa taa agcattgcca atcaagtat tggactttaa            642
Lys Phe Asn Ser Leu Lys
    175 aatttagccc ttatttaccg cctaattatt tgatt                                 677

<210> SEQ ID NO 22
<211> LENGTH: 179
<212> TYPE: PRT
<213> ORGANISM: H. influenzae

<400> SEQUENCE: 22

Met Gln Thr Ile Ser Lys Gln Leu Ser Ala Val Ile Phe Pro Phe Ile
1               5                   10                  15

Phe Ser Ala Cys Val Ser Gln Ser Ala Ser Ser Leu Asp His Gln Ala
            20                  25                  30

Ala Ala Lys Ala Arg Val Glu Leu Ala Leu Ser Tyr Leu Gln Gln Asn
        35                  40                  45
```

-continued

```
Asn Pro Gln Leu Ala Lys Ile Asn Leu Asp Lys Ala Leu Gln His Asp
         50                  55                  60

Lys Asn Tyr Tyr Leu Val His Ser Ala Leu Ala His Tyr Tyr Gln Gln
 65                  70                  75                  80

Gln Gly Gln Ile Glu Asn Ala Phe Arg Glu Tyr Glu Ile Ala Val Lys
                 85                  90                  95

Leu Asn His Lys Gln Gly Asp Val His Asn Asn Phe Gly Thr Phe Leu
            100                 105                 110

Cys Ser Gln Lys Lys Phe Glu Gln Ala Gln Gln Gln Phe Glu Leu Ala
            115                 120                 125

Leu Asn Ser Pro Asn Tyr Tyr His Gln Ala Asp Thr Phe Glu Asn Ile
        130                 135                 140

Ala Leu Cys Ala Tyr Ser Ala Lys Lys Met Asp Ile Tyr Gln Gln Thr
145                 150                 155                 160

Leu Glu Lys Leu Arg Gln Ile Asn Gly Lys Arg Ala Glu Lys Phe Asn
                165                 170                 175

Ser Leu Lys

<210> SEQ ID NO 23
<211> LENGTH: 19
<212> TYPE: DNA
<213> ORGANISM: Artificial sequence
<220> FEATURE:
<223> OTHER INFORMATION: Synthetic primer

<400> SEQUENCE: 23
tgtgacactt ccgcaaaaa                                             19

<210> SEQ ID NO 24
<211> LENGTH: 21
<212> TYPE: DNA
<213> ORGANISM: Artificial sequence
<220> FEATURE:
<223> OTHER INFORMATION: Synthetic primer

<400> SEQUENCE: 24
taataaaagg aaaatgaatg a                                          21

<210> SEQ ID NO 25
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 25 atg aaa tta aca aca cag caa acc ttg aaa aaa ggg ttt aca tta ata    48
Met Lys Leu Thr Thr Gln Gln Thr Leu Lys Lys Gly Phe Thr Leu Ile
 1               5                  10                  15 gag cta atg att gtg att gca att att gct att tta gcc act atc gca    96
Glu Leu Met Ile Val Ile Ala Ile Ile Ala Ile Leu Ala Thr Ile Ala
             20                  25                  30 att ccc tct tat caa aat tat act aaa aaa gca gcg gta tct gaa tta   144
Ile Pro Ser Tyr Gln Asn Tyr Thr Lys Lys Ala Ala Val Ser Glu Leu
         35                  40                  45 ctg caa gcg tca gcg cct tat aag gct gat gtg gaa tta tgt gta tat   192
Leu Gln Ala Ser Ala Pro Tyr Lys Ala Asp Val Glu Leu Cys Val Tyr
     50                  55                  60 agc aca aat gaa aca aca aac tgt acg ggt gga aaa aat ggt att gca   240
Ser Thr Asn Glu Thr Thr Asn Cys Thr Gly Gly Lys Asn Gly Ile Ala
```

-continued

```
Ser Thr Asn Glu Thr Thr Asn Cys Thr Gly Gly Lys Asn Gly Ile Ala
 65                  70                  75                  80 gca gat ata acc aca gca aaa ggc tat gta aaa tca gtg aca aca agc      288
Ala Asp Ile Thr Thr Ala Lys Gly Tyr Val Lys Ser Val Thr Thr Ser
                 85                  90                  95 aac ggt gca ata aca gta aaa ggg gat ggc aca ttg gca aat atg gaa      336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca      384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc      432
Thr Thr Cys Lys Gly Thr Asp Ala Ser Leu Phe Pro Ala Asn Phe Cys
    130                 135                 140 gga agt gtc aca caa                                                  447
Gly Ser Val Thr Gln
145
```

```
<210> SEQ ID NO 26
<211> LENGTH: 149
<212> TYPE: PRT
<213> ORGANISM: H. influenzae

<400> SEQUENCE: 26

Met Lys Leu Thr Thr Gln Gln Thr Leu Lys Lys Gly Phe Thr Leu Ile
 1               5                  10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145
```

```
<210> SEQ ID NO 27
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 27 atg aaa tta aca aca cag caa acc ttg aaa aaa ggg ttt aca tta ata       48
Met Lys Leu Thr Thr Gln Gln Thr Leu Lys Lys Gly Phe Thr Leu Ile
 1               5                  10                  15 gag cta atg att gtg att gca att att gct att tta gcc act atc gca       96
Glu Leu Met Ile Val Ile Ala Ile Ile Ala Ile Leu Ala Thr Ile Ala
                20                  25                  30
```

```
att ccc tct tat caa aat tat act aaa aaa gca gcg gta tct gaa tta    144
Ile Pro Ser Tyr Gln Asn Tyr Thr Lys Lys Ala Ala Val Ser Glu Leu
        35                  40                  45 ctg caa gcg tca gcg cct tat aag gct gat gtg gaa tta tgt gta tat    192
Leu Gln Ala Ser Ala Pro Tyr Lys Ala Asp Val Glu Leu Cys Val Tyr
 50                  55                  60 agc aca aat gaa aca aca aac tgt acg ggt gga aaa aat ggt att gca    240
Ser Thr Asn Glu Thr Thr Asn Cys Thr Gly Gly Lys Asn Gly Ile Ala
 65                  70                  75                  80 gca gat ata acc aca gca aaa ggc tat gta aaa tca gtg aca aca agc    288
Ala Asp Ile Thr Thr Ala Lys Gly Tyr Val Lys Ser Val Thr Thr Ser
                 85                  90                  95 aac ggt gca ata aca gta aaa ggg gat ggc aca ttg gca aat atg gaa    336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca    384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc    432
Thr Thr Cys Lys Gly Thr Asp Ala Ser Leu Phe Pro Ala Asn Phe Cys
130                 135                 140 gga agt gtc aca caa                                                447
Gly Ser Val Thr Gln
145

<210> SEQ ID NO 28
<211> LENGTH: 149
<212> TYPE: PRT
<213> ORGANISM: H. influenzae

<400> SEQUENCE: 28

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
 50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
130                 135                 140

Gly Ser Val Thr Gln
145

<210> SEQ ID NO 29
<211> LENGTH: 447
<212> TYPE: DNA
<213> ORGANISM: H. influenzae
<220> FEATURE:
<221> NAME/KEY: CDS
<222> LOCATION: (1)..(447)
```

<400> SEQUENCE: 29

```
atg aaa tta aca aca cag caa acc ttg aaa aaa ggg ttt aca tta ata      48
Met Lys Leu Thr Thr Gln Gln Thr Leu Lys Lys Gly Phe Thr Leu Ile
1               5                   10                  15 gag cta atg att gtg att gca att att gct att tta gcc act atc gca      96
Glu Leu Met Ile Val Ile Ala Ile Ile Ala Ile Leu Ala Thr Ile Ala
                20                  25                  30 att ccc tct tat caa aat tat act aaa aaa gca gcg gta tct gaa tta     144
Ile Pro Ser Tyr Gln Asn Tyr Thr Lys Lys Ala Ala Val Ser Glu Leu
            35                  40                  45 ctg caa gcg tca gcg cct tat aag gct gat gtg gaa tta tgt gta tat     192
Leu Gln Ala Ser Ala Pro Tyr Lys Ala Asp Val Glu Leu Cys Val Tyr
        50                  55                  60 agc aca aat gaa aca aca aac tgt acg ggt gga aaa aat ggt att gca     240
Ser Thr Asn Glu Thr Thr Asn Cys Thr Gly Gly Lys Asn Gly Ile Ala
65                  70                  75                  80 gca gat ata acc aca gca aaa ggc tat gta aaa tca gtg aca aca agc     288
Ala Asp Ile Thr Thr Ala Lys Gly Tyr Val Lys Ser Val Thr Thr Ser
                85                  90                  95 aac ggt gca ata aca gta aaa ggg gat ggc aca ttg gca aat atg gaa     336
Asn Gly Ala Ile Thr Val Lys Gly Asp Gly Thr Leu Ala Asn Met Glu
            100                 105                 110 tat att ttg caa gct aca ggt aat gct gca aca ggt gta act tgg aca     384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc     432
Thr Thr Cys Lys Gly Thr Asp Ala Ser Leu Phe Pro Ala Asn Phe Cys
130                 135                 140 gga agt gtc aca caa                                                 447
Gly Ser Val Thr Gln
145
```

<210> SEQ ID NO 30
<211> LENGTH: 149
<212> TYPE: PRT
<213> ORGANISM: H. influenzae

<400> SEQUENCE: 30

```
Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
                20                  25                  30

Ile Pro Ser Tyr Gln Asn Tyr Thr Lys Lys Ala Ala Val Ser Glu Leu
            35                  40                  45

Leu Gln Ala Ser Ala Pro Tyr Lys Ala Asp Val Glu Leu Cys Val Tyr
        50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
130                 135                 140

Gly Ser Val Thr Gln
145
```

<210> SEQ ID NO 31
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 31

| | | | | | | | | | | | | | | | | |
|---|---|---|---|---|---|---|---|---|---|---|---|---|---|---|---|---|
| atg | aaa | tta | aca | aca | cag | caa | acc | ttg | aaa | aaa | ggg | ttt | aca | tta | ata | 48 |
| Met | Lys | Leu | Thr | Thr | Gln | Gln | Thr | Leu | Lys | Lys | Gly | Phe | Thr | Leu | Ile | |
| 1 | | | | 5 | | | | | 10 | | | | | 15 | | |
| gag | cta | atg | att | gtg | att | gca | att | att | gct | att | tta | gcc | act | atc | gca | 96 |
| Glu | Leu | Met | Ile | Val | Ile | Ala | Ile | Ile | Ala | Ile | Leu | Ala | Thr | Ile | Ala | |
| | | | 20 | | | | | 25 | | | | | 30 | | | |
| att | ccc | tct | tat | caa | aat | tat | act | aaa | aaa | gca | gcg | gta | tct | gaa | tta | 144 |
| Ile | Pro | Ser | Tyr | Gln | Asn | Tyr | Thr | Lys | Lys | Ala | Ala | Val | Ser | Glu | Leu | |
| | | 35 | | | | | 40 | | | | | 45 | | | | |
| ctg | caa | gcg | tca | gcg | cct | tat | aag | gct | gat | gtg | gaa | tta | tgt | gta | tat | 192 |
| Leu | Gln | Ala | Ser | Ala | Pro | Tyr | Lys | Ala | Asp | Val | Glu | Leu | Cys | Val | Tyr | |
| | 50 | | | | | 55 | | | | | 60 | | | | | |
| agc | aca | aat | gaa | aca | aca | aac | tgt | acg | ggt | gga | aaa | aat | ggt | att | gca | 240 |
| Ser | Thr | Asn | Glu | Thr | Thr | Asn | Cys | Thr | Gly | Gly | Lys | Asn | Gly | Ile | Ala | |
| 65 | | | | | 70 | | | | | 75 | | | | | 80 | |
| gca | gat | ata | acc | aca | gca | aaa | ggc | tat | gta | aaa | tca | gtg | aca | aca | agc | 288 |
| Ala | Asp | Ile | Thr | Thr | Ala | Lys | Gly | Tyr | Val | Lys | Ser | Val | Thr | Thr | Ser | |
| | | | | 85 | | | | | 90 | | | | | 95 | | |
| aac | ggt | gca | ata | aca | gta | aaa | ggg | gat | ggc | aca | ttg | gca | aat | atg | gaa | 336 |
| Asn | Gly | Ala | Ile | Thr | Val | Lys | Gly | Asp | Gly | Thr | Leu | Ala | Asn | Met | Glu | |
| | | | 100 | | | | | 105 | | | | | 110 | | | |
| tat | att | ttg | caa | gct | aca | ggt | aat | gct | gca | aca | ggt | gta | act | tgg | aca | 384 |
| Tyr | Ile | Leu | Gln | Ala | Thr | Gly | Asn | Ala | Ala | Thr | Gly | Val | Thr | Trp | Thr | |
| | | | | 115 | | | | | 120 | | | | | 125 | | |
| aca | act | tgc | aaa | gga | acg | gat | gcc | tct | tta | ttt | cca | gca | aat | ttt | tgc | 432 |
| Thr | Thr | Cys | Lys | Gly | Thr | Asp | Ala | Ser | Leu | Phe | Pro | Ala | Asn | Phe | Cys | |
| | 130 | | | | | 135 | | | | | 140 | | | | | |
| gga | agt | gtc | aca | caa | | | | | | | | | | | | 447 |
| Gly | Ser | Val | Thr | Gln | | | | | | | | | | | | |
| 145 | | | | | | | | | | | | | | | | |

<210> SEQ ID NO 32
<211> LENGTH: 149
<212> TYPE: PRT
<213> ORGANISM: H. influenzae

<400> SEQUENCE: 32

| | | | | | | | | | | | | | | |
|---|---|---|---|---|---|---|---|---|---|---|---|---|---|---|
| Met | Lys | Leu | Thr | Thr | Gln | Gln | Thr | Leu | Lys | Lys | Gly | Phe | Thr | Leu | Ile |
| 1 | | | | 5 | | | | | 10 | | | | | 15 | |

| Glu | Leu | Met | Ile | Val | Ile | Ala | Ile | Ile | Ala | Ile | Leu | Ala | Thr | Ile | Ala |
|---|---|---|---|---|---|---|---|---|---|---|---|---|---|---|---|
| | | | 20 | | | | | 25 | | | | | 30 | | |

| Ile | Pro | Ser | Tyr | Gln | Asn | Tyr | Thr | Lys | Lys | Ala | Ala | Val | Ser | Glu | Leu |
|---|---|---|---|---|---|---|---|---|---|---|---|---|---|---|---|
| | | 35 | | | | | 40 | | | | | 45 | | | |

| Leu | Gln | Ala | Ser | Ala | Pro | Tyr | Lys | Ala | Asp | Val | Glu | Leu | Cys | Val | Tyr |
|---|---|---|---|---|---|---|---|---|---|---|---|---|---|---|---|
| | 50 | | | | | 55 | | | | | 60 | | | | |

| Ser | Thr | Asn | Glu | Thr | Thr | Asn | Cys | Thr | Gly | Gly | Lys | Asn | Gly | Ile | Ala |
|---|---|---|---|---|---|---|---|---|---|---|---|---|---|---|---|
| 65 | | | | | 70 | | | | | 75 | | | | | 80 |

| Ala | Asp | Ile | Thr | Thr | Ala | Lys | Gly | Tyr | Val | Lys | Ser | Val | Thr | Thr | Ser |
|---|---|---|---|---|---|---|---|---|---|---|---|---|---|---|---|
| | | | | 85 | | | | | 90 | | | | | 95 | |

```
Asn Gly Ala Ile Thr Val Lys Gly Asp Gly Thr Leu Ala Asn Met Glu
            100                 105                 110
Tyr Ile Leu Gln Ala Thr Gly Asn Ala Ala Thr Gly Val Thr Trp Thr
        115                 120                 125
Thr Thr Cys Lys Gly Thr Asp Ala Ser Leu Phe Pro Ala Asn Phe Cys
    130                 135                 140
Gly Ser Val Thr Gln
145

<210> SEQ ID NO 33
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 33 atg aaa tta aca aca cag caa acc ttg aaa aaa ggt ttt aca tta atc      48
Met Lys Leu Thr Thr Gln Gln Thr Leu Lys Lys Gly Phe Thr Leu Ile
1               5                   10                  15 gag cta atg att gtg att gca att att gct att tta gcc act atc gca      96
Glu Leu Met Ile Val Ile Ala Ile Ile Ala Ile Leu Ala Thr Ile Ala
            20                  25                  30 att cct tct tat caa aat tat acc aaa aaa gct tcg gta tcc gaa tta     144
Ile Pro Ser Tyr Gln Asn Tyr Thr Lys Lys Ala Ser Val Ser Glu Leu
        35                  40                  45 ctg caa gca tct gca cct tat aag gct gat gtg gaa tta tgt gta tat     192
Leu Gln Ala Ser Ala Pro Tyr Lys Ala Asp Val Glu Leu Cys Val Tyr
    50                  55                  60 agc aca aat gaa aca aca aac tgt acg ggt gga aaa aat ggt att gca     240
Ser Thr Asn Glu Thr Thr Asn Cys Thr Gly Gly Lys Asn Gly Ile Ala
65                  70                  75                  80 gct gat att aca aca gca aaa ggc tat gta gcc tca gtg aaa act caa     288
Ala Asp Ile Thr Thr Ala Lys Gly Tyr Val Ala Ser Val Lys Thr Gln
                85                  90                  95 tcg ggt ggc att aca gta aaa ggg aat ggc aca ttg gca aat atg gaa     336
Ser Gly Gly Ile Thr Val Lys Gly Asn Gly Thr Leu Ala Asn Met Glu
            100                 105                 110 tat att ttg caa gct aaa ggt aat gct aca gca ggt gta act tgg aca     384
Tyr Ile Leu Gln Ala Lys Gly Asn Ala Thr Ala Gly Val Thr Trp Thr
        115                 120                 125 aca acc tgc aaa gga acg gat gcc tct tta ttt cca gca aat ttt tgc     432
Thr Thr Cys Lys Gly Thr Asp Ala Ser Leu Phe Pro Ala Asn Phe Cys
    130                 135                 140 aga agt gtc aca aaa                                                 447
Arg Ser Val Thr Lys
145

<210> SEQ ID NO 34
<211> LENGTH: 149
<212> TYPE: PRT
<213> ORGANISM: H. influenzae

<400> SEQUENCE: 34

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ser Val Ser Glu Leu
        35                  40                  45
```

```
Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
 65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
            115                 120                 125

Thr Thr Cys Lys Gly Thr Asp Ala Ser Leu Phe Pro Ala Asn Phe Cys
        130                 135                 140

Arg Ser Val Thr Lys
145

<210> SEQ ID NO 35
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 35 atg aaa tta aca aca cag caa acc ttg aaa aaa ggg ttt aca tta ata      48
Met Lys Leu Thr Thr Gln Gln Thr Leu Lys Lys Gly Phe Thr Leu Ile
 1               5                  10                  15 gag cta atg att gtg att gca att att gct att tta gcc acc atc gca      96
Glu Leu Met Ile Val Ile Ala Ile Ile Ala Ile Leu Ala Thr Ile Ala
             20                  25                  30 att cct tct tat aaa aat tat act aaa aaa gca gcg gta tct gaa tta     144
Ile Pro Ser Tyr Lys Asn Tyr Thr Lys Lys Ala Ala Val Ser Glu Leu
         35                  40                  45 ctg caa gct tct gcg cct tat aag gct gat gtg gaa tta tgt gta tat     192
Leu Gln Ala Ser Ala Pro Tyr Lys Ala Asp Val Glu Leu Cys Val Tyr
     50                  55                  60 agc aca aat gaa ata aca aat tgt atg ggt gga aaa aat ggt att gca     240
Ser Thr Asn Glu Ile Thr Asn Cys Met Gly Gly Lys Asn Gly Ile Ala
 65                  70                  75                  80 gct gat att aca aca gca aaa ggc tat gta gcc tca gtg aaa act caa     288
Ala Asp Ile Thr Thr Ala Lys Gly Tyr Val Ala Ser Val Lys Thr Gln
                 85                  90                  95 tcg ggt ggc att acc gta aaa ggg gat ggc aca ttg gca aat atg gaa     336
Ser Gly Gly Ile Thr Val Lys Gly Asp Gly Thr Leu Ala Asn Met Glu
            100                 105                 110 tat att ttg caa gct aca ggt aat gct gca gca ggt gta act tgg aca     384
Tyr Ile Leu Gln Ala Thr Gly Asn Ala Ala Ala Gly Val Thr Trp Thr
            115                 120                 125 aca acc tgc aaa gga acg gat gcc tct tta ttt cca gca aat ttt tgc     432
Thr Thr Cys Lys Gly Thr Asp Ala Ser Leu Phe Pro Ala Asn Phe Cys
        130                 135                 140 gga agt atc aca caa                                                  447
Gly Ser Ile Thr Gln
145

<210> SEQ ID NO 36
<211> LENGTH: 149
<212> TYPE: PRT
<213> ORGANISM: H. influenzae
```

```
<400> SEQUENCE: 36

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Lys Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Ile Thr Asn Cys Met Gly Gly Lys Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asp Gly Thr Leu Ala Asn Met Glu
            100                 105                 110

Tyr Ile Leu Gln Ala Thr Gly Asn Ala Ala Gly Val Thr Trp Thr
        115                 120                 125

Thr Thr Cys Lys Gly Thr Asp Ala Ser Leu Phe Pro Ala Asn Phe Cys
130                 135                 140

Gly Ser Ile Thr Gln
145

<210> SEQ ID NO 37
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 37 atg aaa tta aca aca ctg caa acc ttg aaa aaa ggg ttt aca tta atc        48
Met Lys Leu Thr Thr Leu Gln Thr Leu Lys Lys Gly Phe Thr Leu Ile
1               5                   10                  15 gag cta atg att gtg att gca att att gct att tta gcc act atc gca        96
Glu Leu Met Ile Val Ile Ala Ile Ile Ala Ile Leu Ala Thr Ile Ala
            20                  25                  30 att cct tct tat caa aat tat acc aaa aaa gct gcg gta tcc gaa tta       144
Ile Pro Ser Tyr Gln Asn Tyr Thr Lys Lys Ala Ala Val Ser Glu Leu
        35                  40                  45 ctg caa gct tct gcg cct tat aag gct gat gtg gaa tta tgc gtt tat       192
Leu Gln Ala Ser Ala Pro Tyr Lys Ala Asp Val Glu Leu Cys Val Tyr
    50                  55                  60 agc aca ggc aaa cct tct act tgc tca gga gga agc aat gga att gca       240
Ser Thr Gly Lys Pro Ser Thr Cys Ser Gly Gly Ser Asn Gly Ile Ala
65                  70                  75                  80 gct gat att acg aca gca aaa ggc tat gta gcc tca gtg aaa act caa       288
Ala Asp Ile Thr Thr Ala Lys Gly Tyr Val Ala Ser Val Lys Thr Gln
                85                  90                  95 tca ggt ggt att aca gta aaa ggg aat ggc aca ttg gca aat atg gaa       336
Ser Gly Gly Ile Thr Val Lys Gly Asn Gly Thr Leu Ala Asn Met Glu
            100                 105                 110 tat att ttg caa gct aca ggt aat gct gca aca ggt gta act tgg aca       384
Tyr Ile Leu Gln Ala Thr Gly Asn Ala Ala Thr Gly Val Thr Trp Thr
        115                 120                 125 aca act tgc aaa gga acg gat gcc tct tta ttt cca gca aat ttt tgc       432
Thr Thr Cys Lys Gly Thr Asp Ala Ser Leu Phe Pro Ala Asn Phe Cys
130                 135                 140
```

```
gga agt gtc aca caa                                                     447
Gly Ser Val Thr Gln
145

<210> SEQ ID NO 38
<211> LENGTH: 149
<212> TYPE: PRT
<213> ORGANISM: H. influenzae

<400> SEQUENCE: 38

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Pro Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Thr Gly Asn Ala Ala Thr Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Gln
145

<210> SEQ ID NO 39
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 39 atg aaa tta aca aca ctg caa acc ttg aaa aaa ggg ttt aca tta atc    48
Met Lys Leu Thr Thr Leu Gln Thr Leu Lys Lys Gly Phe Thr Leu Ile
1               5                   10                  15 gag cta atg att gtg att gca att att gct att tta gcc act atc gca    96
Glu Leu Met Ile Val Ile Ala Ile Ile Ala Ile Leu Ala Thr Ile Ala
            20                  25                  30 att cct tct tat caa aat tat acc aaa aaa gct gcg gta tcc gaa tta    144
Ile Pro Ser Tyr Gln Asn Tyr Thr Lys Lys Ala Ala Val Ser Glu Leu
        35                  40                  45 ctg caa gct tct gcg cct tat aag gct gat gtg gaa tta tgc gtt tat    192
Leu Gln Ala Ser Ala Pro Tyr Lys Ala Asp Val Glu Leu Cys Val Tyr
    50                  55                  60 agc aca ggc aaa ctt tct act tgc tca gga gga agc aat gga att gca    240
Ser Thr Gly Lys Leu Ser Thr Cys Ser Gly Gly Ser Asn Gly Ile Ala
65                  70                  75                  80 gct gat att aca aca gca aaa ggc tat gta gcc tca gtg aaa act caa    288
Ala Asp Ile Thr Thr Ala Lys Gly Tyr Val Ala Ser Val Lys Thr Gln
                85                  90                  95 tca ggt ggt att aca gta aaa ggg aat ggc aca ttg gca aat atg gaa    336
Ser Gly Gly Ile Thr Val Lys Gly Asn Gly Thr Leu Ala Asn Met Glu
```

```
tat att ttg caa gct aaa ggt aat gct aca gca ggt gta act tgg aca        384
Tyr Ile Leu Gln Ala Lys Gly Asn Ala Thr Ala Gly Val Thr Trp Thr
            115                 120                 125 aca acc tgc aaa gga acg gat gcc tct tta ttt cca gca aat ttt tgc        432
Thr Thr Cys Lys Gly Thr Asp Ala Ser Leu Phe Pro Ala Asn Phe Cys
    130                 135                 140 gga agt gtc aca aaa                                                    447
Gly Ser Val Thr Lys
145

<210> SEQ ID NO 40
<211> LENGTH: 149
<212> TYPE: PRT
<213> ORGANISM: H. influenzae

<400> SEQUENCE: 40

Met Lys Leu Thr Thr Leu Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Gly Lys Leu Ser Thr Cys Ser Gly Gly Ser Asn Gly Ile Ala
65                  70                  75                  80

Ala Asp Ile Thr Thr Ala Lys Gly Tyr Val Ala Ser Val Lys Thr Gln
                85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Gly Ser Val Thr Lys
145

<210> SEQ ID NO 41
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 41 atg aaa tta aca aca cag caa acc ttg aaa aaa ggt ttt aca tta atc        48
Met Lys Leu Thr Thr Gln Gln Thr Leu Lys Lys Gly Phe Thr Leu Ile
1               5                   10                  15 gag cta atg att gtg att gca att att gct att tta gcc act atc gca        96
Glu Leu Met Ile Val Ile Ala Ile Ile Ala Ile Leu Ala Thr Ile Ala
            20                  25                  30 att cct tct tat caa aat tat acc aaa aaa gct tcg gta tcc gaa tta       144
Ile Pro Ser Tyr Gln Asn Tyr Thr Lys Lys Ala Ser Val Ser Glu Leu
        35                  40                  45 ctg caa gct tcc gca cct tat aag tca gat gtg gaa tta tgc gtt tat       192
Leu Gln Ala Ser Ala Pro Tyr Lys Ser Asp Val Glu Leu Cys Val Tyr
    50                  55                  60
```

```
agc aca ggc aaa cct tct act tgc tca gga gga agc aat gga att gca       240
Ser Thr Gly Lys Pro Ser Thr Cys Ser Gly Gly Ser Asn Gly Ile Ala
 65                  70                  75                  80 gct gat att aca aca gca aaa ggc tat gta gcc tca gtg aaa act caa       288
Ala Asp Ile Thr Thr Ala Lys Gly Tyr Val Ala Ser Val Lys Thr Gln
                 85                  90                  95 tca ggt ggt att aca gta aaa ggg aat ggc aca ttg gca aat atg gaa       336
Ser Gly Gly Ile Thr Val Lys Gly Asn Gly Thr Leu Ala Asn Met Glu
            100                 105                 110 tat att ttg caa gct aaa ggt aat gct aca gca ggt gta act tgg aca       384
Tyr Ile Leu Gln Ala Lys Gly Asn Ala Thr Ala Gly Val Thr Trp Thr
        115                 120                 125 aca acc tgc aaa gga acg gat gcc tct tta ttt cca gca aat ttt tgc       432
Thr Thr Cys Lys Gly Thr Asp Ala Ser Leu Phe Pro Ala Asn Phe Cys
    130                 135                 140 aga agt gtc aca aaa                                                   447
Arg Ser Val Thr Lys
145

<210> SEQ ID NO 42
<211> LENGTH: 149
<212> TYPE: PRT
<213> ORGANISM: H. influenzae

<400> SEQUENCE: 42

Met Lys Leu Thr Thr Gln Gln Thr Leu Lys Lys Gly Phe Thr Leu Ile
  1               5                  10                  15

Glu Leu Met Ile Val Ile Ala Ile Ile Ala Ile Leu Ala Thr Ile Ala
             20                  25                  30

Ile Pro Ser Tyr Gln Asn Tyr Thr Lys Lys Ala Ser Val Ser Glu Leu
         35                  40                  45

Leu Gln Ala Ser Ala Pro Tyr Lys Ser Asp Val Glu Leu Cys Val Tyr
     50                  55                  60

Ser Thr Gly Lys Pro Ser Thr Cys Ser Gly Gly Ser Asn Gly Ile Ala
 65                  70                  75                  80

Ala Asp Ile Thr Thr Ala Lys Gly Tyr Val Ala Ser Val Lys Thr Gln
                 85                  90                  95

Ser Gly Gly Ile Thr Val Lys Gly Asn Gly Thr Leu Ala Asn Met Glu
            100                 105                 110

Tyr Ile Leu Gln Ala Lys Gly Asn Ala Thr Ala Gly Val Thr Trp Thr
        115                 120                 125

Thr Thr Cys Lys Gly Thr Asp Ala Ser Leu Phe Pro Ala Asn Phe Cys
    130                 135                 140

Arg Ser Val Thr Lys
145

<210> SEQ ID NO 43
<211> LENGTH: 447
<212> TYPE: DNA
<213> ORGANISM: H. influenzae
<220> FEATURE:
<221> NAME/KEY: CDS
<222> LOCATION: (1)..(447)

<400> SEQUENCE: 43 atg aaa tta aca aca cag caa acc ttg aaa aaa ggg ttt aca tta ata        48
Met Lys Leu Thr Thr Gln Gln Thr Leu Lys Lys Gly Phe Thr Leu Ile
  1               5                  10                  15 gag cta atg att gtg att gca att att gct att tta gcc act atc gca        96
Glu Leu Met Ile Val Ile Ala Ile Ile Ala Ile Leu Ala Thr Ile Ala
```

```
                          20                  25                  30
att ccc tct tat caa aat tat act aaa aaa gcg gcg gta tct gaa tta         144
Ile Pro Ser Tyr Gln Asn Tyr Thr Lys Lys Ala Ala Val Ser Glu Leu
         35                  40                  45 ctg caa gcg tca gcg cct tat aag gct gat gtg gaa tta tgt gta tat         192
Leu Gln Ala Ser Ala Pro Tyr Lys Ala Asp Val Glu Leu Cys Val Tyr
 50                  55                  60 agt aca ggt aaa cct tcc agt tgc tcg gga gga agc aat gga att gcg         240
Ser Thr Gly Lys Pro Ser Ser Cys Ser Gly Gly Ser Asn Gly Ile Ala
 65                  70                  75                  80 gct gat att aca aca gca aaa ggc tat gta aaa tca gtg aca aca agc         288
Ala Asp Ile Thr Thr Ala Lys Gly Tyr Val Lys Ser Val Thr Thr Ser
                 85                  90                  95 aac ggt gca ata aca gta aaa ggg gat ggc aca ttg gca aat atg gaa         336
Asn Gly Ala Ile Thr Val Lys Gly Asp Gly Thr Leu Ala Asn Met Glu
             100                 105                 110 tat att ttg caa gcc agt ggt aat gct gca aca ggt gta act tgg aca         384
Tyr Ile Leu Gln Ala Ser Gly Asn Ala Ala Thr Gly Val Thr Trp Thr
         115                 120                 125 aca act tgc aaa gga acg gat gcc tct tta ttt cca gca aat ttt tgc         432
Thr Thr Cys Lys Gly Thr Asp Ala Ser Leu Phe Pro Ala Asn Phe Cys
 130                 135                 140 gga agt gtc aca caa                                                     447
Gly Ser Val Thr Gln
145

<210> SEQ ID NO 44
<211> LENGTH: 149
<212> TYPE: PRT
<213> ORGANISM: H. influenzae

<400> SEQUENCE: 44

Met Lys Leu Thr Thr Gln Gln Thr Leu Lys Lys Gly Phe Thr Leu Ile
1               5                   10                  15

Glu Leu Met Ile Val Ile Ala Ile Ala Ile Leu Ala Thr Ile Ala
            20                  25                  30

Ile Pro Ser Tyr Gln Asn Tyr Thr Lys Lys Ala Ala Val Ser Glu Leu
         35                  40                  45

Leu Gln Ala Ser Ala Pro Tyr Lys Ala Asp Val Glu Leu Cys Val Tyr
 50                  55                  60

Ser Thr Gly Lys Pro Ser Ser Cys Ser Gly Gly Ser Asn Gly Ile Ala
 65                  70                  75                  80

Ala Asp Ile Thr Thr Ala Lys Gly Tyr Val Lys Ser Val Thr Thr Ser
                 85                  90                  95

Asn Gly Ala Ile Thr Val Lys Gly Asp Gly Thr Leu Ala Asn Met Glu
             100                 105                 110

Tyr Ile Leu Gln Ala Ser Gly Asn Ala Ala Thr Gly Val Thr Trp Thr
         115                 120                 125

Thr Thr Cys Lys Gly Thr Asp Ala Ser Leu Phe Pro Ala Asn Phe Cys
 130                 135                 140

Gly Ser Val Thr Gln
145
```